(12) United States Patent
Suzuki et al.

(10) Patent No.: US 7,875,879 B2
(45) Date of Patent: Jan. 25, 2011

(54) LIGHT-EMITTING ELEMENT, LIGHT-EMITTING DEVICE, ELECTRONIC DEVICE AND QUINOXALINE DERIVATIVE

(75) Inventors: Tsunenori Suzuki, Kanagawa (JP); Satoshi Seo, Kanagawa (JP); Sachiko Kawakami, Kanagawa (JP)

(73) Assignee: Semiconductor Energy laboratory Co., Ltd. (JP)

( * ) Notice: Subject to any disclaimer, the term of this patent is extended or adjusted under 35 U.S.C. 154(b) by 312 days.

(21) Appl. No.: 12/033,245

(22) Filed: Feb. 19, 2008

(65) Prior Publication Data

US 2008/0217608 A1 Sep. 11, 2008

(30) Foreign Application Priority Data

Feb. 21, 2007 (JP) .............................. 2007-040379

(51) Int. Cl.
*H01L 35/24* (2006.01)
*H01L 51/00* (2006.01)

(52) U.S. Cl. .................. 257/40; 257/79; 257/E51.001; 544/353

(58) Field of Classification Search .................. 257/40, 257/79; 544/353
See application file for complete search history.

(56) References Cited

U.S. PATENT DOCUMENTS

| | | | | |
|---|---|---|---|---|
| 4,760,006 | A * | 7/1988 | Pawlowski | .................... 430/78 |
| 6,509,109 | B1 * | 1/2003 | Nakamura et al. | .......... 428/690 |
| 6,734,457 | B2 | 5/2004 | Yamazaki et al. | |
| 7,239,081 | B2 | 7/2007 | Tsutsui | |
| 2003/0027016 | A1 * | 2/2003 | Ara et al. | .................... 428/690 |
| 2005/0065342 | A1 * | 3/2005 | Shitagaki et al. | ............ 544/353 |
| 2006/0029828 | A1 | 2/2006 | Kanno et al. | |
| 2006/0051615 | A1 | 3/2006 | Kanno et al. | |
| 2008/0006821 | A1 | 1/2008 | Suzuki et al. | |
| 2008/0007164 | A1 | 1/2008 | Suzuki et al. | |
| 2008/0241586 | A1 * | 10/2008 | Kumaki et al. | ............... 428/690 |

FOREIGN PATENT DOCUMENTS

JP 6-207169 7/1994

(Continued)

OTHER PUBLICATIONS

Tsutsui, T. et al, "High Quantum Efficiency in Organic Light-Emitting Devices with Iridium-Complex as a Triplet Emissive Center," Japanese Journal of Applied Physics, vol. 38, part 2, No. 12B, Dec. 15, 1999, pp. L-1502-L-1504.

(Continued)

*Primary Examiner*—Kenneth A Parker
*Assistant Examiner*—Anthony Ho
(74) *Attorney, Agent, or Firm*—Husch Blackwell LLP Welsh Katz

(57) ABSTRACT

A substrate including a semiconductor layer, where characteristics of an element can be evaluated with high reliability, and an evaluating method thereof are provided. A substrate including a semiconductor layer of the invention has a closed-loop circuit in which an antenna coil and a semiconductor element are connected in series, and a surface of an area over which the circuit is formed is covered with an insulating film. By using such a circuit, a contactless inspection can be carried out. Further, a ring oscillator can be substituted for the closed-loop circuit.

20 Claims, 37 Drawing Sheets

FOREIGN PATENT DOCUMENTS

| | | |
|---|---|---|
| JP | 7-26255 | 1/1995 |
| JP | 2006-66872 | 3/2006 |
| JP | 2006-253444 | 9/2006 |
| WO | WO 2006049334 A1 * | 5/2006 |
| WO | WO 2007/069741 A1 | 6/2007 |

OTHER PUBLICATIONS

Goldsmith, C.R. et al, "C-H Bond Activation by a Ferric Methoxide Complex: Modeling the Rate-Determining Step in the Mechanism of Lipoxygenase," Journal of the American Chemical Society, vol. 124, No. 1, 2002, pp. 83-96.

Ohnishi, T. et al, *High Molecular EL Material*, Kyoritsu Shuppan, publisher, Japan, 2004, pp. 64-67 (in Japanese).

International Search Report re application No. PCT/JP2008/052593, dated Apr. 1, 2008.

Written Opinion re application No. PCT/JP2008/052593, dated Apr. 1, 2008.

* cited by examiner

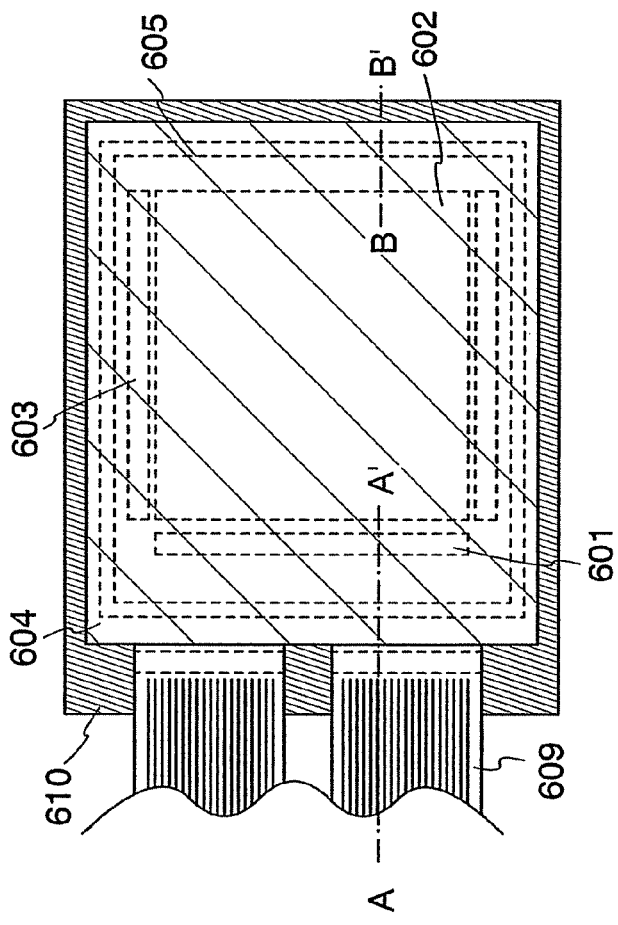
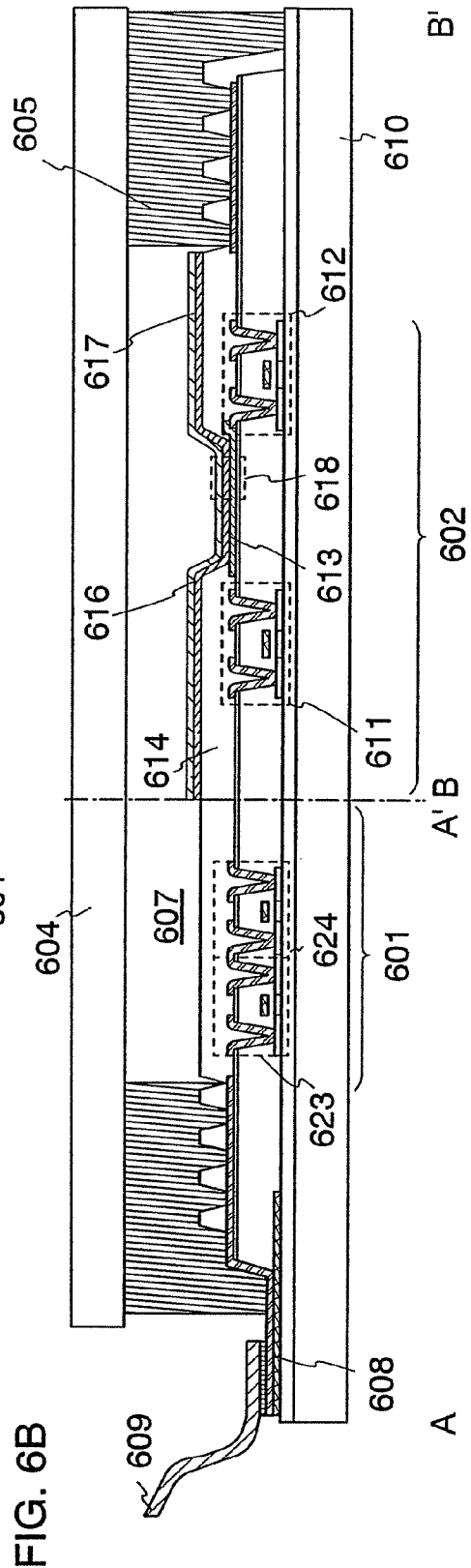
FIG. 6A
FIG. 6B

LIGHT-EMITTING ELEMENT, LIGHT-EMITTING DEVICE, ELECTRONIC DEVICE AND QUINOXALINE DERIVATIVE

TECHNICAL FIELD

The present invention relates to current excitation type light-emitting elements. Further, the present invention relates to light-emitting devices and electronic devices having the light-emitting element.

BACKGROUND ART

In recent years, research and development have been actively conducted on light-emitting elements using electroluminescence. In a basic structure of such a light-emitting element, a layer including a substance having a light-emitting property is interposed between a pair of electrodes. By voltage application to this element, light emission can be obtained from the substance having a light-emitting property.

Since such light-emitting elements is of self-light-emitting type, it is considered that the light-emitting elements have advantages over liquid crystal display devices in that visibility of pixels is high, backlight is not required, and so on and is therefore suitable as flat panel display elements. In addition, other advantages of such light-emitting elements are that the elements can be manufactured to be thin and lightweight and the response speed is very high.

Since such light-emitting elements can be formed into a film shape, plane light emission can be easily obtained by forming a large-area element. This is a feature which is difficult to be obtained by point light sources typified by an incandescent lamp and an LED or linear light sources typified by a fluorescent lamp. Accordingly, the light-emitting element is extremely effective for use as a planar light source applicable to illumination and the like.

Light-emitting elements using electroluminescence are classified broadly according to whether they use an organic compound or an inorganic compound as a substance having a light-emitting property.

When an organic compound is used as a light-emitting substance, electrons and holes are injected into a layer including a light-emitting organic compound from a pair of electrodes by voltage application to a light-emitting element, so that current flows therethrough. The electrons and holes (i.e., carriers) are recombined, and thus the light-emitting organic compound is excited. The light-emitting organic compound returns to a ground state from the excited state, thereby emitting light. Based on this mechanism, such a light-emitting element is called current excitation type light-emitting element.

It is to be noted that the excited state generated by an organic compound can be a singlet excited state or a triplet excited state, and luminescence from the singlet excited state is referred to as fluorescence, and luminescence from the triplet excited state is referred to as phosphorescence.

In improving element characteristics of such a light-emitting element, there are a lot of problems which depend on a material used, and in order to solve the problems, improvement of an element structure, development of a material, and the like have been carried out.

For example, in Reference 1, a hole-blocking layer is formed in a light-emitting element, so that the light-emitting element using a phosphorescent material can emit light efficiently. However, such a hole blocking layer has poor durability as described in Reference 1 and the light-emitting element has short lifetime (Reference 1: Tetsuo Tsutsui and eight others, Japanese Journal of Applied Physics, vol. 38, L1502-L1504 (1999)). Thus, a light-emitting element having longer lifetime is desired.

DISCLOSURE OF INVENTION

The present invention has been made in view of the above problem. It is an object of the present invention to provide light-emitting elements having long lifetime. Further, it is another object of the present invention to provide light-emitting devices and electronic devices having long lifetime.

The present inventors have studied earnestly, and found that a substance having an electron-trapping property is added to an electron-transporting layer to control electron transfer, so that the change over time of carrier balance can be suppressed. Further, we have found that light-emitting elements having long lifetime can be obtained, as a result. Furthermore, we have found that an energy gap of the substance having an electron-trapping property is made larger than an energy gap of a light-emitting substance, so that light emission from the substance having an electron-trapping property can be prevented and the light-emitting element can have excellent color purity.

Thus, an aspect of the present invention is a light-emitting element including a first layer and a second layer including a light-emitting substance between a first electrode and a second electrode. The first layer includes a first organic compound and a second organic compound, and is formed between the second layer and the second electrode. In the first layer, the first organic compound is included more than the second organic compound, and the first organic compound is an organic compound having an electron-transporting property, while the second organic compound is an organic compound having an electron-trapping property. An energy gap of the second organic compound is larger than an energy gap of the light-emitting substance. When a voltage is applied such that a potential of the first electrode is higher than a potential of the second electrode, the light-emitting layer can emit light.

In addition, a specific value which exhibits an electron trapping property is preferably a depth for trapping of 0.3 eV or higher. Therefore, an aspect of the present invention is a light-emitting element including a first layer and a second layer including a light-emitting substance between a first electrode and a second electrode. The first layer includes a first organic compound and a second organic compound, and is formed between the second layer and the second electrode. In the first layer, the first organic compound that is an organic compound having an electron-transporting property is included more than the second organic compound. The lowest unoccupied molecular orbital (LUMO) level of the second organic compound is lower than the lowest unoccupied molecular orbital (LUMO) level of the first organic compound by 0.3 eV or more, and an energy gap of the second organic compound is larger than an energy gap of the light-emitting substance. When a voltage is applied such that a potential of the first electrode is higher than a potential of the second electrode, the light-emitting layer can emit light.

Further, light-emitting elements emitting visible light of blue to red are effective for wide variety of applications, such as display devices. Since the second organic compound has a higher energy gap than that of visible light, light-emission from the second organic compound can be prevented, so that the light-emitting element can have excellent color purity. Accordingly, in the above light-emitting element, the energy gap of the second organic compound is preferably 3.0 eV or higher. In addition, when light emission of the second organic compound is in a region of ultraviolet to purple, energy can transfer to the light-emitting substance even if the second organic compound is excited; accordingly, a light-emitting element with excellent color purity can be obtained. Therefore, in the above light-emitting element, the emission peak of the second organic compound is preferably within the range of 350 nm to 450 nm. Therefore, it is more preferable that the energy gap of the second organic compound is 3.0 eV or higher and the emission peak wavelength is within the range of 350 nm to 450 nm, inclusive.

In the above light-emitting element, when the second layer has an electron-transporting property, an effect of long lifetime is remarkable in particular. Therefore, according to an aspect of the present invention, in the light-emitting element, the second layer has an electron-transporting property, more preferably, the second layer includes a light-emitting substance and a third organic compound, the third organic compound is included more than the light-emitting substance, and the third organic compound has an electron-transporting property. Also at this time, in order to avoid rise of driving voltage, the third organic compound preferably has not only an electron-transporting property but also a hole-accepting property. In view of this, the third organic compound is preferably an anthracene derivative.

In addition, the effect of excellent color purity is remarkable when the first layer and the second layer are contact with each other. Therefore, according to an aspect of the present invention, in the light-emitting element, the first layer and the light-emitting layer are arranged to be in contact with each other.

Further, since the first layer has an electron-trapping property, a driving voltage is increased if the thickness is too large, on the other hand, if the thickness is too small, the effect of the present invention is not secured so well. Therefore, in the above light-emitting element, the thickness of the first layer is preferably within 5 nm to 20 nm, inclusive.

Note that the first organic compound has an electro-transporting property, but the first organic compound is preferably a metal complex in terms of electric stability and appropriate electron-transporting property.

In addition, the present inventors have found that a quinoxaline derivative is particularly preferable as a substance which satisfies the condition of the second organic compound. Therefore, according to an aspect of the present invention, in the light-emitting element, the second organic compound is a quinoxaline derivative. The quinoxaline derivative is preferably 2,3-diphenylquinoxaline derivative, in terms of chemical stability. Further, among 2,3-diphenylquinoxaline derivatives, in particular, 2,3,2',3'-tetraphenyl-6,6'-biquinoxaline derivative, which has a relatively high molecular weight and high heat resistance, is preferable.

As for the 2,3,2',3'-tetraphenyl-6,6'-biquinoxaline derivative, the present inventors have found that a 2,3,2',3'-tetraphenyl-6,6'-biquinoxaline derivative whose phenyl group is substituted by an electron-withdrawing group (a fluoro group, a cyano group, a trifluoromethyl group, a nitro group, an acyl group, an acyloxy group or the like) has a relatively high electron-trapping property and molecular weight. Therefore, according to an aspect of the present invention, in the light-emitting element, the second organic compound is a quinoxaline derivative represented by a general formula (1). The quinoxaline derivative represented by the general formula (1) is a novel material that the present inventors have developed and is included in the present invention.

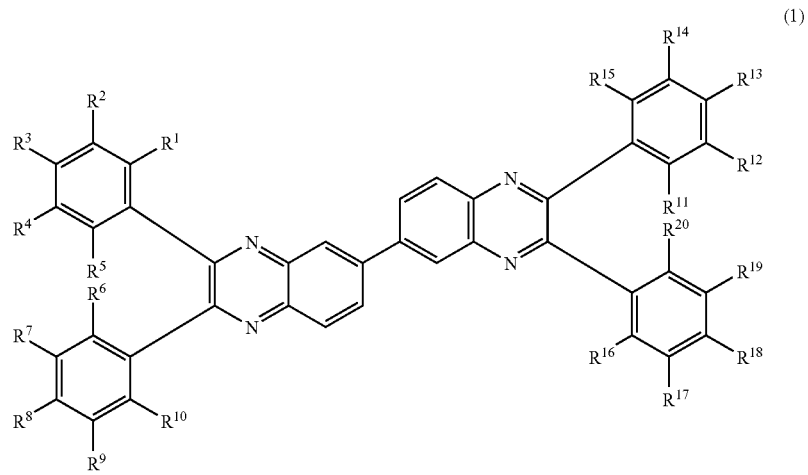

(1)

In the formula, at least one of $R^1$ to $R^{20}$ is any of a fluoro group, a cyano group, a trifluoromethyl group, a nitro group, an acyl group and an acyloxy group, and the others are hydrogen.

In particular, among quinoxaline derivatives represented by the general formula (1), a quinoxaline derivative represented by a general formula (2) is preferable. Therefore, according to an aspect of the present invention, in the light-emitting element, the second organic compound is a quinoxaline derivative represented by the general formula (2). The quinoxaline derivative represented by the general formula (2) is a novel substance that the present inventors have developed and is included in the present invention.

(2)

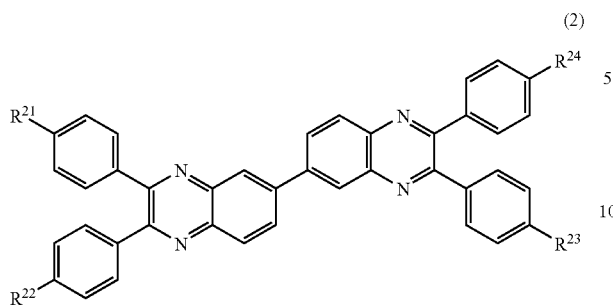

In the formula, at least one of R21 to R24 is any of a fluoro group, a cyano group, a trifluoromethyl group, a nitro group, an acyl group and an acyloxy group, and the others are hydrogen.

In the general formula (2), a case is preferable in which $R^{21}$ to $R^{24}$ are all substituted, since a high electron-trapping property is obtained. In other words, preferably, $R^{21}$ to $R^{24}$ independently represent at least one of a fluoro group, a cyano group, a trifluoromethyl group, a nitro group, an acyl group and an acyloxy group. Furthermore, a case is more preferable in which $R^{21}$ to $R^{24}$ independently represent at least one of a fluoro group, a cyano group, a trifluoromethyl group, a nitro group, an acyl group and an acyloxy group, and $R^{21}$ to $R^{24}$ are all the same substituent.

Note that a light-emitting element as described above can be applied to diverse types of light-emitting devices. Therefore, light-emitting devices including a light-emitting element of the present invention as described above and a control means to control light emission of the light-emitting element are included in the present invention. The "light-emitting device" in this specification includes image display devices, light-emitting devices and light sources (including illumination devices and lighting devices). In addition, a module in which a connector, for example, an FPC (Flexible Printed Circuit), TAB (Tape Automated Bonding) tape, or a TCP (Tape Carrier Package), is attached to a panel where a light-emitting element is formed; a module in which a printed circuit board is provided ahead of a module in which one or some of this TAB tape or one of these TCPs is attached; and a module in which an IC (integrated circuit) is directly mounted in a light-emitting element by a COG (Chip On Glass) method; are all included in the "light-emitting device".

A light-emitting element of the present invention is effective, in particular, for display portions of electronic devices, since the light-emitting element has high visibility and long lifetime. Therefore, the present invention includes electronic devices having a display portion, and in which the display portion includes a light-emitting element of the present invention as described above and a control means to control light emission of the light-emitting element.

A light-emitting element of the present invention includes a layer to control electron transfer and suppress change over time of carrier balance. Thus, a light-emitting element with long lifetime can be obtained.

By applying a light-emitting element of the present invention to a light-emitting device, the light-emitting device can have long lifetime. Further, by applying a light-emitting element of the present invention to a display portion of an electronic device, the display portion of the electronic device can have long lifetime.

BRIEF DESCRIPTION OF DRAWINGS

In the accompanying drawings:
FIGS. 6A and 6B show a light-emitting device according to an aspect of the present invention.

BEST MODE FOR CARRYING OUT THE INVENTION

Embodiment Modes

First, a factor of luminance decay in a light-emitting element will now be described. In general, many light-emitting elements are driven by a constant amount of current, and in such a case, luminance decay indicates decrease of current efficiency. The current efficiency is light output with respect to flowing current, and thus is greatly dependent on how many carriers of flowing carriers contribute to recombination (carrier balance) or how many carriers of the carriers recombined (i.e., exciton) in a light-emitting layer contribute to light emission (quantum yield).

Therefore, as the factor of luminance decay, change over time of carrier balance or deterioration over time of quantum yield is thought to be a major factor. The present invention focuses on change over time of carrier balance.

Hereinafter, Embodiment Modes will be explained in detail below with reference to the accompanied drawings. It is easily understood by those skilled in the art that modes and details disclosed herein can be modified in various ways without departing from the spirit and scope of the present invention. Therefore, the present invention should not be interpreted as being limited to the description of the embodiment modes to be given below.

Note that in this specification, the term "composition" indicates not only a state in which two materials are simply mixed, but also a state in which a plurality of materials are mixed and thus electron transfer is conducted between the plurality of materials.

Embodiment Mode 1

Figure 1:
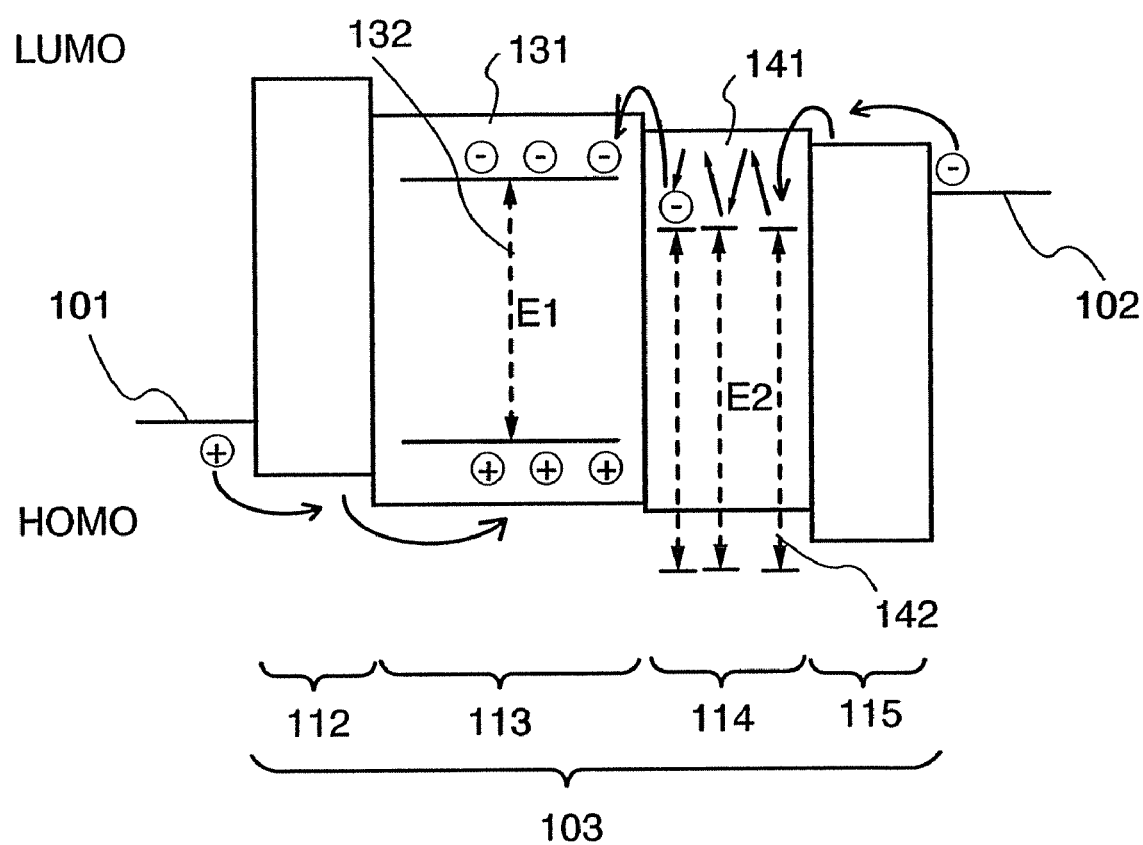
FIG. 1 is a band diagram of a light-emitting element according to an aspect of the present invention.

A principle of a light-emitting element of the present invention will be described first. FIG. 1 is a band diagram of the light-emitting element as an example. The light-emitting element of the present invention includes a first layer 114 and a second layer 113 including a light-emitting substance between a first electrode 101 and a second electrode 102. The first layer 114 is formed between the second layer 113 and the second electrode 102. The first layer 114 includes a first organic compound 141 and a second organic compound 142 each having an electron-transporting property, and includes the first organic compound 141 more than the second organic compound 142. In addition, as shown in FIG. 1, the LUMO level of the second organic compound 142 is lower than the LUMO level of the first organic compound 141, and thus the second organic compound 142 has an electron-trapping property. In addition, the second layer 113 shown in FIG. 1 has a structure in which a light-emitting substance 132 is added to a third organic compound 131, but may include only a light-emitting substance. In addition, reference numerals 112 and 115 represent a hole-transporting layer and an electron-transporting layer respectively, but these layers are not necessarily provided and may be provided as appropriate.

To a light-emitting element having such an energy band structure, a voltage is applied such that a potential of the second electrode 102 is higher than that of the first electrode 101. At this time, holes injected from a Fermi level of the first electrode 101 pass through a HOMO level of the hole-transporting layer 112 and are injected into the second layer 113. On the other hand, electrons injected from a Fermi level of the second electrode 202 pass through a LUMO level of the electron-transporting layer 115 and are injected into the first layer 114. The electrons injected from the first layer 114 moves more slowly due to the second organic compound 142 having an electron-trapping property. The slow electrons are injected into the second layer 113 which includes the light-emitting substance 132, and are recombined with holes to emit light.

For example, when the second layer 113 has an electron-transporting property, i.e., when the third organic compound 131 in FIG. 1 has an electron-transporting property, holes injected to the second layer 113 from the hole-transporting layer 112 moves slowly. Therefore, if in a conventional light-emitting element without having the first layer 114, electrons are injected to the second layer 113 without slowing down and reach the vicinity of the interface of the hole-transporting layer 112. Therefore, a light-emitting region is formed in the vicinity of the interface between the hole-transporting layer 112 and the second layer 113. At this time, electrons may reach the hole-transporting layer 112 and thereby the hole-transporting layer 112 may deteriorate, unfortunately. Further, the increase over time of the amount of the electrons that may reach the hole-transporting layer leads to decrease the probability of recombination in the light-emitting layer over time, and thus decrease of lifetime of the light-emitting element (luminance decay over time) is caused.

On the other hand, in the light-emitting element of the present invention, the first layer 114 is formed, and in the first layer 114, the second organic compound having an electron-trapping function is added to the first organic compound having an electron-transporting property. Therefore, electrons injected into the first layer 114 move more slowly and electron-injecting to the second layer 113 is controlled. As a result, in the present invention, a light-emitting region, which conventionally tends to be formed in the vicinity of the interface between the hole-transporting layer 112 and the second layer 113, is formed in a portion of within the second layer 113 to the vicinity of the interface between the second layer 113 and the first layer 114. Accordingly, there is less possibility that electrons may reach the hole-transporting layer 112 and thereby the hole-transporting layer 212 may deteriorate. In addition, there is almost no possibility that holes may reach the electron-transporting layer 115 and thereby the electron-transporting layer 115 may deteriorate, since the first layer 114 includes the first organic compound having an electron-transporting property.

Further, it is an important point of the present invention not that merely a compound with low electron mobility is applied to the first layer 114 but that an organic compound having a function of trapping electrons is added to an organic compound having an electron-transporting property. With such a structure, it becomes possible not only to control electron injection to the second layer 213 but also to suppress changes over time in the controlled amount of electron injection. Therefore, the light-emitting element of the present invention can prevent a phenomenon that carrier balance is lost over time, which could otherwise lower the recombination probability. Thus, the lifetime of the element can be improved (luminance decay over time can be suppressed).

In the light-emitting element of the present invention, the light-emitting region is not formed at the interface between the light-emitting layer and the hole-transporting layer or the interface between the light-emitting layer and the electron-transporting layer. Therefore, there is no adverse effect of deterioration which would otherwise be caused if the light-emitting region is positioned close to the hole-transporting layer or the electron-transporting layer. Further, changes over time in carrier balance (in particular, changes over time in amount of electron injection) can be suppressed. Therefore, a long-lifetime light-emitting element which does not easily deteriorate can be obtained.

Further, it is important for the light-emitting element of the present invention that an energy gap E2 of the second organic compound included in the first layer 114 is higher than an energy gap E1 of the light-emitting substance 132 included in the second layer 113. The reason is that by making E2 larger than E1 (E2>E1), formation of exciton in the second organic compound 142 can be suppressed, although the second organic compound 142 has high electron-trapping property and may be excited in the element. Therefore, light emission from the light-emitting substance 132 can be obtained without being mixed with a color of emission of the second organic compound 142; accordingly, a light-emitting element having excellent color purity can be obtained.

Next, one mode of a light-emitting element of the present invention will now be described with reference to FIG. 2A. The light-emitting element of the present invention has a plurality of layers between a pair of electrodes. The plurality of layers are stacked by combining layers made of a compound with a high carrier injection property and a compound with a high carrier transporting property so that a light-emitting region is formed at a position away from the electrodes, i.e., so that carriers are recombined at a position away from the electrodes.

In this embodiment mode, the light-emitting element includes a first electrode 201, a second electrode 202, and an EL layer 203 formed between the first electrode 201 and the second electrode 202. The EL layer 203 includes a first layer 214 and a second layer 213 including a light-emitting substance, and the first layer 214 is formed between the second layer 213 and the second electrode 202. The first layer 214 includes a first organic compound and a second organic compound each having an electron-transporting property, and in the first layer 214, the first organic compound 141 is included more than the second organic compound. In addition, the second organic compound has an electron-trapping property. In this embodiment mode, description is made below, in which the first electrode 201 serves as an anode and the second electrode 202 serves as a cathode. In other words, when a voltage is applied to the first electrode 201 and the second electrode 202 such that a potential of the first electrode 201 is higher than that of the second electrode 202, light is emitted. Such a case is described.

A substrate 200 is used as a support of the light-emitting element. As the substrate 200, for example, glass, plastic or the like can be used. Any material that can serve as a support in the manufacturing process of the light-emitting element can be used, in addition to the above materials.

The first electrode 201 is preferably formed using a material with a high work function (i.e., 4.0 eV or higher) such as metals, alloys, electrically conductive compounds, or a mixture of them. Specifically, indium tin oxide (ITO), ITO including silicon or silicon oxide, indium zinc oxide (IZO), indium oxide including tungsten oxide and zinc oxide, and the like can be given. Such conductive metal oxide films are generally formed by sputtering, but may also be formed by an inkjet method, a spin coating method, or the like by application of a sol-gel method or the like. For example, indium zinc oxide (IZO) can be deposited by a sputtering method using a target in which 1 to 20 wt % of zinc oxide is added to indium oxide. In addition, indium oxide including tungsten oxide and zinc oxide can be deposited by a sputtering method using a target in which 0.5 to 5 wt % of tungsten oxide and 0.1 to 1 wt % of zinc oxide are added to indium oxide. Further, gold (Au), platinum (Pt), nickel (Ni), tungsten (W), chromium (Cr), molybdenum (Mo), iron (Fe), cobalt (Co), copper (Cu), palladium (Pd), titanium (Ti), nitride of metal materials (e.g., titanium nitride), or the like can be used.

When a layer including a composite material which will be described later is used as a layer in contact with the first electrode 201, the first electrode 201 can be formed using a wide variety of metals, alloys, electrically conductive compound, a mixture of them, or the like regardless of their work functions. For example, aluminum (Al), silver (Ag), an aluminum alloy (AlSi), or the like can be used. Besides, an element belonging to Group 1 or 2 of the periodic table which has a low work function, i.e., alkali metals such a lithium (Li) and cesium (Cs) and alkaline earth metals such as magnesium (Mg), calcium (Ca), and strontium (Sr); alloys of them (e.g., MgAg and AlLi); rare earth metals such as europium (Eu) and ytterbium (Yb); alloys of them; and the like can also be used. A film made of an alkali metal, an alkaline earth metal, or an alloy of them can be formed by a vacuum evaporation method. Further, a film made of an alloy of an alkali metal or an alkaline earth metal can be formed by a sputtering method. It is also possible to deposit a silver paste or the like by an inkjet method or the like.

The EL layer 203 includes a hole-injecting layer 211, a hole-transporting layer 212, an electron-transporting layer 215, and an electron-injecting layer 216, as well as the first layer 214 and the second layer 213 including a light-emitting substance. Note that the EL layer 203 should include at least the first layer 214 and the second layer including a light-emitting substance, which are described specifically in this embodiment mode, but there are no particular limitations on the other layers. For example, the hole-injecting layer, the hole-transporting layer, the electron-transporting layer, the electron-injecting layer and/or the like may be combined as appropriate.

The hole-injecting layer 211 is a layer including a substance with a high hole injection property. As such a substance with a high hole injection property, molybdenum oxide, vanadium oxide, ruthenium oxide, tungsten oxide, manganese oxide, or the like can be used. Besides, phthalocyanine compounds such as phthalocyanine (abbreviation: $H_2PC$), copper(II) phthalocyanine (abbreviation: CuPc), and vanadyl phthalocyanine (VOPc) can also be given as low molecular organic compounds. Further, the following low molecular organic compounds can be used: aromatic amine compounds such as 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1).

Alternatively, the hole-injecting layer 211 can be formed using a composite material in which a substance with an acceptor property is mixed into a substance with a high hole-transporting property. Note that when a composite material in which a substance with an acceptor property is mixed into a substance with a high hole-transporting property is used, a material for forming the electrode can be selected regardless of its work function. That is, not only a material with a high work function, but also a material with a low work function can be used for the first electrode 201. Such a composite material can be formed by co-depositing a substance with a high hole-transporting property and a substance with an acceptor property.

As such a substance with a high hole-transporting property used for the composite material, a wide variety of compounds such as aromatic amine compounds, carbazole derivatives, aromatic hydrocarbons, and high molecular compounds (e.g., oligomer, dendrimer, or polymer) can be used. Specifically, a substance having a hole mobility of $10^{-6}$ cm$^2$/Vs or higher is preferably used. However, other substances than the above substances may also be used, as long as the hole-transporting properties thereof are higher than the electron-transporting properties thereof. Specific substances with a high hole-transporting property that can be used for the composite material are described below.

For example, the following organic compounds can be used for such a substance with a high hole-transporting property: in addition to MTDATA, TDATA, DPAB, DNTPD, DPA3B, PCzPCA1, PCzPCA2, PCzPCN1, aromatic amine compounds such as 4,4'-bis[N-(1-naphthyl)-N-phenylamino]biphenyl (abbreviation: NPB or α-NPD), and N,N'-bis(3-methylphenyl)-N,N'-dipheny-[1,1'-biphenyl]-4,4'-diamine (abbreviation: TPD); and carbazole derivatives such as 4,4'-di(N-carbazolyl)biphenyl (abbreviation: CBP), 1,3,5-tris[4-(N-carbazolyl)phenyl]benzene (abbreviation: TCPB), and 1,4-bis[4-(N-carbazolyl)phenyl-2,3,5,6-tetraphenylbenzene. Alternatively, the following aromatic hydrocarbon compounds can also be used: 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butyl-anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

As a substance with an acceptor property, organic compounds such as 7,7,8,8-tetracyano-2,3,5,6-tetrafluoroquinodimethane (abbreviation: $F_4$-TCNQ) and chloranil, and transition metal oxide can be given. In addition, oxide of metals belonging to Groups 4 to 8 in the periodic table can also be given. Specifically, it is preferable to use vanadium oxide, niobium oxide, tantalum oxide, chromium oxide, molybdenum oxide, tungsten oxide, manganese oxide, and rhenium oxide which have high electron accepting properties. Above all, molybdenum oxide is particularly preferable because it is stable even in atmospheric air, has a low hygroscopic property, and is easy to handle.

For the hole-injecting layer 211, high molecular compounds (e.g., oligomer, dendrimer, or polymer) can be used. For example, the following high molecular compounds can be used: poly(N-vinylcarbazole) (abbreviation: PVK), poly(4-vinyl triphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine (abbreviation: Poly-TPD). Further, high molecular compounds mixed with acid, such as poly (3,4-ethylenedioxythiophene)/poly(styrenesulfonate) (PEDOT/PSS) and polyaniline/poly(styrenesulfonate) (PAni/PSS) can also be used.

Note that it is also possible to form the hole-injecting layer 211 using a composite material which is formed from the above-described high molecular compound such as PVK, PVTAP, PTPDMA, or Poly-TPD and the above-described substance having an acceptor property.

The hole-transporting layer 212 is a layer including a substance with a high hole-transporting property. As such a substance with a high hole-transporting property, the following low molecular organic compounds can be used in addition to the above-described NPB (or α-NPD) and TPD: aromatic amine compounds such as 4,4'-bis[N-(9,9-dimethylfluoren-2-yl)-N-phenylamino]biphenyl (abbreviation: DFLDPBi), and 4,4'-bis[N-(spiro-9,9'-bifluoren-2-yl)-N-phenylamino]biphenyl (abbreviation: BSPB). The substances described here are mainly substances having a hole mobility of $10^{-6}$ cm$^2$/Vs or higher. Further, other substances than the above substances may also be used, as long as the hole-transporting properties thereof are higher than the electron-transporting properties thereof. Note that the layer including a substance with a high hole-transporting property is not limited to a single layer but may have a stacked structure of two or more layers made of the above-described substances.

Further, the hole-transporting layer 212 may also be formed with a high molecular compound such as PVK, PVTPA, PTPDMA, or Poly-TPD.

The second layer 213 is a layer including a light-emitting substance, i.e., a light-emitting layer. The second layer 213 can be formed using a wide variety of materials Specifically, as a light-emitting material which exhibits bluish light, the following can be used: N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl) triphenylamine (abbreviation: YGAPA), and the like. As a light-emitting material which exhibits greenish light emission, the following can be used: N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-a mine (abbreviation: 2YGABPhA), N,N,9-triphenylanthracen-9-amine (abbreviation: DPhAPhA), and the like. As a light-emitting material which exhibits yellowish light emission, rubrene, 5,12-bis(1,1'-biphenyl-4-yl)-6,11-diphenyltetracene (abbreviation: BPT), and the like can be used. Further, as a light-emitting material which exhibits reddish light emission, N,N,N',N'-tetrakis(4-methylphenyl)tetracene-5,11-diamine (abbreviation: p-mPhTD); 7,13-diphenyl-N,N,N',N-tetrakis(4-methylphenyl)acenaphtho[1,2-α]fluoranthene-3,10-dia mine (abbreviation: p-mPhAFD), and the like can be used. Alternatively, a phosphorescent material such as bis[2-(2'-benzo[4,5-α]thienyl)pyridinato-N,C$^{3'}$]iridium(III)acetylacetonate (abbreviation: Ir(btp)$_2$(acac)) can also be used.

Note that in the light-emitting element of the present invention, the second layer 213, i.e., the light-emitting layer preferably has an electron-transporting property. Conventionally, when a light-emitting layer has an electron-transporting property, an electron-blocking layer has been provided between the light-emitting layer and an anode in order to prevent electrons from penetrating the light-emitting layer. However, when the electron-blocking layer has deteriorated over time, a recombination region expands to the inside of the electron-blocking layer (or inside of the hold-transporting layer), which could result in a significant decrease in current efficiency (i.e., luminance decay). Meanwhile, in the present invention, the movement of electrons is controlled before the electrons reach the light-emitting layer (between the light-emitting layer and the cathode). Therefore, even when the balance of electrons is somewhat lost, the proportion of recombination in the light-emitting layer hardly changes, which is advantageous in that luminance does not easily decay. As described above, when the second layer 213, i.e., the light-emitting layer has an electron-transporting property, the effect of long lifetime is remarkable.

Note that the second layer 213 may also have a structure in which the above-described light-emitting substance is dispersed in another substance. For example, as illustrated in FIG. 1, a light-emitting substance may be dispersed in the third organic compound. Various types of substances can be used for the third organic compound, and it is preferable to use a substance whose lowest unoccupied molecular orbital (LUMO) level is higher than that of the light-emitting substance and whose highest occupied molecular orbital (HOMO) level is lower than that of the light-emitting substance.

Note that in the light-emitting element of the present invention, the light-emitting layer preferably has an electron-transporting property as described above. That is, the electron-transporting property of the light-emitting layer is preferably higher than the hole-transporting property thereof. Therefore, as the third organic compound, an organic compound having an electron-transporting property is preferably used. Specifically, the following metal complexes can be used: tris(8-quinolinolato)aluminum(III) (abbreviation: Alq); tris(4-methyl-8-quinolinolato)aluminum(III) (abbreviation: Almq$_3$), bis(10-hydroxybenzo[h]-quinolinato)beryllium(II) (abbreviation: BeBq$_2$), bis(2-methyl-8-quinolinolato)(4-phenylphenolato)aluminum(III) (BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: Zn(BTZ)$_2$). Further, the following heterocyclic compounds can also be used: 2-(4-biphenylyl)-5-(4-tert-butylphenyl)-1,3,4-oxadiazole (abbreviation: PBD), 1,3-bis[5-(4-tert-buthylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)tris(1-phenyl-1H-benzimidazole) (abbreviation: TPBI), bathophenanthroline (abbreviation: BPhen), and bathocuproine (abbreviation: BCP). Alternatively, the following condensed aromatic compounds can also be used: 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)

diphenanthrene (abbreviation: DPNS), 9,9'-(stilbene-4,4'-diyl)diphenanthrene (abbreviation: DPNS2), and 3,3',3''-(benzene-1,3,5-triyl)tripyrene (abbreviation: TPB3).

In particular, the third organic compound preferably also has a hole-accepting property, although it has an electron-transporting property, in order to prevent increase of a driving voltage. In view of this, the third organic compound is preferably an anthracene derivative such as CzPA, DPCzPA, DNA, or t-BuDNA described above.

As a material in which the light-emitting substance is dispersed, a plurality of kinds of materials can be used as well as the third organic compound. For example, a compound for controlling the crystallization, such as rubrene or the like can be further added in order to control the crystallization. In addition, NPB, Alq, or the like can be further added in order to efficiently transfer energy to the light-emitting substance.

When a structure in which such a light-emitting substance is dispersed in another compound is employed, the crystallization of the second layer 213 can be suppressed. Further, concentration quenching which results from the high concentration of the light-emitting substance can also be suppressed.

Further, high molecular compounds can be used for the third layer 213 Specifically, as a light-emitting material which exhibits bluish light emission, the following can be used: poly(9,9-dioctylfluorene-2,7-diyl) (abbreviation: PFO), poly[(9,9-dioctylfluorene-2,7-diyl-co-(2,5-dimethoxybenzene-1,4-diyl)] (abbreviation: RF-DMOP), poly{(9,9-dioctylfluorene-2,7-diyl)-co-[N,N'-di-(p-butylphenyl)-1,4-diaminobenzene]} (abbreviation: TAB-PFH), and the like. As a light-emitting material which exhibits greenish light emission, the following can be used: poly(p-phenylenevinylene) (abbreviation: PPV), poly[(9,9-dihexylfluorene-2,7-diyl)-alt-co-(benzo[2,1,3]thiadiazol-4,7-diyl)] (abbreviation: PFBT), poly[(9,9-dioctylfluorene-2,7-divinylenefluorenylene)-alt-co-(2-methoxy-5-(2-ethylhexyl oxy)-1,4-phenylene)], and the like. As a light-emitting material which exhibits orangish to reddish light emission, the following can be used: poly[2-methoxy-5-(2'-ethylhexoxy)-1,4-phenylenevinylene] (abbreviation: MEH-PPV), poly(3-butylthiophene-2,5-diyl), poly{[9,9-diexyl-2,7-bis(1-cyanovinylene)fluorenylene]-alt-co-[2,5-bis(N,N'-diphenylamino)-1,4-phenylene]}, poly{[2-methoxy-5-(2-ethylhexyloxy)-1,4-bis(1-cyanovinylenephenylene)]-alt-co-[2,5-bis(N,N'-diphenylamino)-1,4-phenylene]} (abbreviation: CN-PPV-DPD), and the like.

The first layer 214 is a layer to control electron transfer. The first layer 214 includes two or more types of substances. The first layer 214 includes the first organic compound and the second organic compound, and the first organic compound is included more than the second organic compound in the first layer 214.

The first layer 214 is formed closer to the second electrode 202 serving as a cathode than the second layer 213 serving as the light-emitting layer, and thus the first organic compound is a compound having an electron-transporting property. In other words, the first organic compound is preferably a substance whose electron-transporting property is higher than its hole-transporting property. Typically, the following can be used: metal complexes such as Alq, Almq$_3$, BeBq$_2$, BAlq, Znq, BAlq, ZnPBO, and ZnBTZ; heterocyclic compounds such as PBD, OXD-7, TAZ, TPBI, BPhen, and BCP; and condensed aromatic compounds such as CzPA, DPCzPA, DPPA, DNA, t-BuDNA, BANT, DPNS, DPNS2, and TPB3. Further, the following high molecular compounds can also be used: poly[(9,9-dihexylfluorene-2,7-diyl)-co-(pyridin-3,5-diyl)] (abbreviation: PF-Py) and poly[(9,9-dioctylfluorene-2,7-diyl)-co-(2,2'-pyridin-6,6'-diyl)] (abbreviation: PF-BPy). Above all, metal complexes are preferably used in terms of electric stability (in particular, stability against electrons) and appropriate electron-transporting property.

The second organic compound is a compound having a function of trapping electrons. Specifically, the second organic compound is preferably an organic compound having a LUMO level which is lower than a LUMO level of the first organic compound by 0.3 eV or more. Since the second organic compound is included, the electron transfer speed of the whole layer is smaller than that of a layer including only the first organic compound. In other words, by addition of the second organic compound, the electron transfer can be controlled. Further, the concentration of the second organic compound is controlled so that the electron transfer speed can be controlled.

Further, as a feature of the light-emitting element of the present invention, an energy gap of the second organic compound is larger than an energy gap of the light-emitting substance included in the second layer 213. As a result, light emission from the light-emitting substance can be obtained without being mixed with a color of emission of the second organic compound; accordingly, a light-emitting element having excellent color purity can be obtained.

An energy gap which is larger than that of visible light, blue to red, which is suitable for practical use is preferable. Thus, the energy gap of the second organic compound is preferably 3.0 eV or larger. In addition, when emission of the second organic compound is light in ultraviolet to purple, energy can transfer to the light-emitting substance included in the second layer 213 even if the second organic compound is excited; accordingly, a light-emitting element with excellent color purity can be obtained. Therefore, the emission peak of the second organic compound is preferably within the range of 350 nm to 450 nm, inclusive.

As the second organic compound having such an energy gap described above, the present inventors have found that a quinoxaline derivative is preferable in particular. The quinoxaline derivative is preferably 2,3-diphenylquinoxaline derivative, in terms of chemical stability. For example, 2,3-diphenylquinoxaline (abbreviation: DPQ), 2,3-bis(4-fluorophenyl)quinoxaline (abbreviation: FDPQ), 2,3-bis (4-trifluoromethylphenyl)quinoxaline (abbreviation: CF$_3$-DPQ), 2,3,5,8-tetraphenylquinoxaline (abbreviation: TPQ), 2,3-bis[4-(10-phenyl-9-anthryl)phenyl]quinoxaline (abbreviation: PAPQ) and the like are given.

Further, among 2,3-diphenylquinoxaline derivatives, in particular, 2,3,2',3'-tetraphenyl-6,6'-biquinoxaline derivative, which has a relatively high molecular weight and high heat resistance, is preferable. As specific examples, in addition to 2,3,2',3'-tetraphenyl-6,6'-biquinoxaline (abbreviation: DPQ2), a quinoxaline derivative represented by the general formula (1) is given.

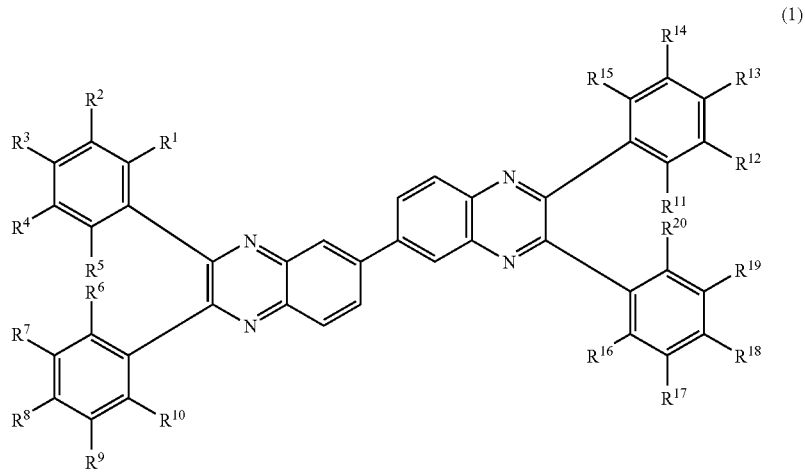

(1)

In the formula, at least one of $R^1$ to $R^{20}$ is any of a fluoro group, a cyano group, a trifluoromethyl group, a nitro group, an acyl group and an acyloxy group, and the others are hydrogen.

In the quinoxaline derivative represented by the general formula (1), a phenyl group of 2,3,2',3'-tetraphenyl-6,6'-biquinoxaline is substituted by an electron-withdrawing group (such as a fluoro group, a cyano group, a trifluoromethyl group, a nitro group, an acyl group, an acyloxy group or the like). The quinoxaline derivative represented by the general formula (1) has relatively high electron-trapping property and molecular weight. Note that the quinoxaline derivative represented by the general formula (1) is a novel substance that the present inventors have developed and is included in the present invention.

In particular, among quinoxaline derivatives represented by the general formula (1), a quinoxaline derivative represented by a general formula (2) is preferable. The quinoxaline derivative represented by the general formula (2) is a novel substance that the present inventors have developed and is included in the present invention.

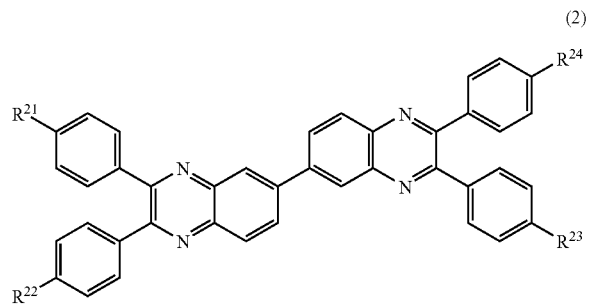

(2)

In the formula, at least one of $R^{21}$ to $R^{24}$ is any of a fluoro group, a cyano group, a trifluoromethyl group, a nitro group, an acyl group and an acyloxy group, and the others are hydrogen.

In the general formula (2), a case is preferable in which $R^{21}$ to $R^{24}$ are all substituted, since a high electron-trapping property is obtained. In other words, preferably, $R^{21}$ to $R^{24}$ independently represent at least one of a fluoro group, a cyano group, a trifluoromethyl group, a nitro group, an acyl group and an acyloxy group. Furthermore, a case is preferable for synthesis, in which $R^{21}$ to $R^{24}$ are at least one of a fluoro group, a cyano group, a trifluoromethyl group, a nitro group, an acyl group and an acyloxy group, and $R^{21}$ to $R^{24}$ are all the same substituent.

Note that the acyl group is preferably an acyl group having 1 to 4 carbon atoms, such as acetyl group. However, a case where a light-emitting element is formed by a wet method is not limited to this. In addition, the acyloxy group is an acyloxy group having 1 to 4 carbon atoms such as acetoxy group. However, a case where a light-emitting element is formed by a wet method is not limited to this.

As specific structures of the quinoxaline derivative represented by the above general formula (1) or (2), the following structural formulae (101) to (211) are given. However, the quinoxaline derivative of the present invention is not limited to those formulae.

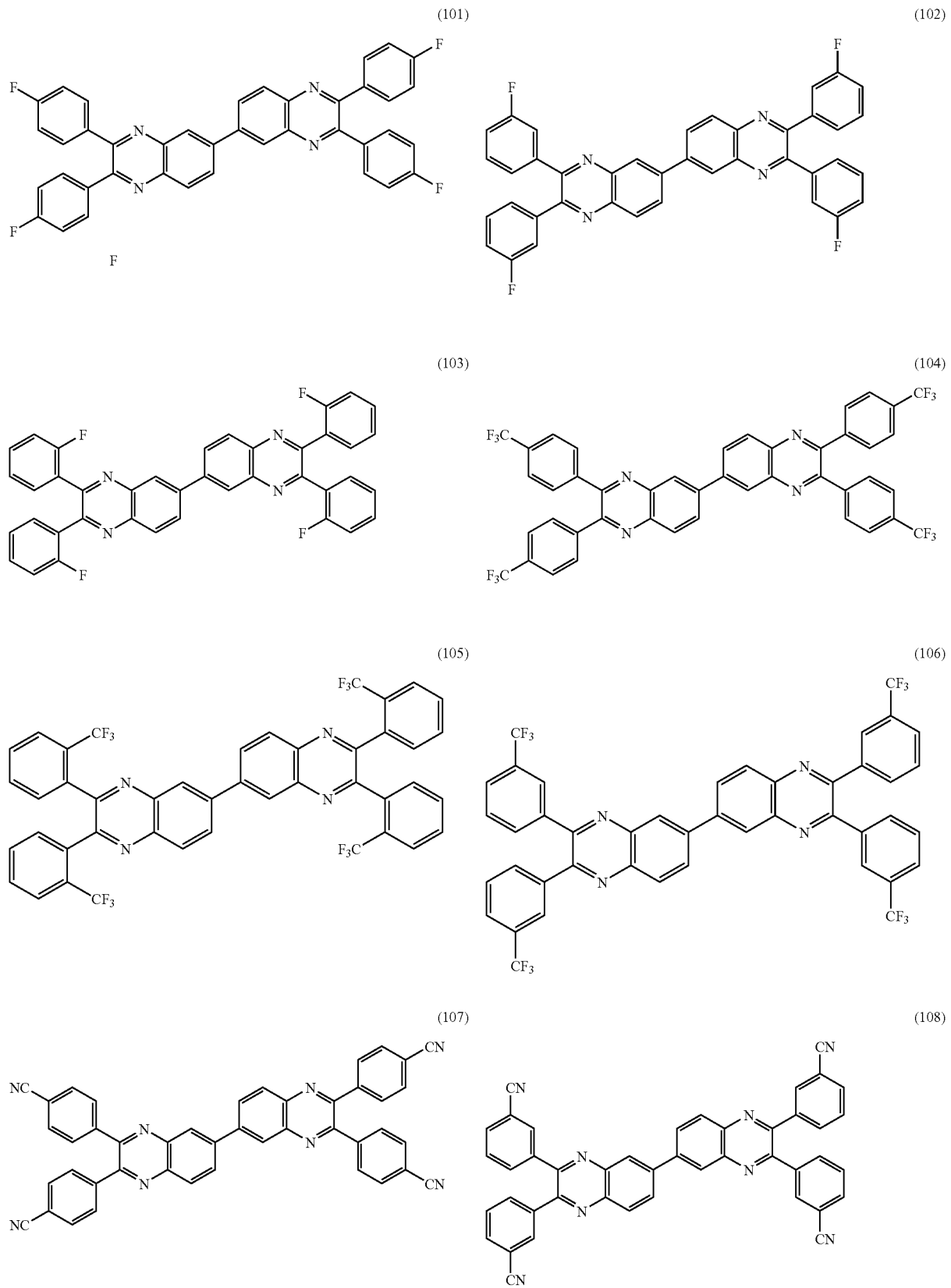

-continued
(109)
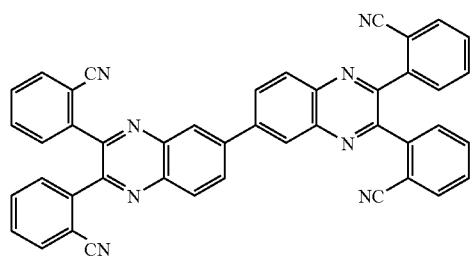
(110)
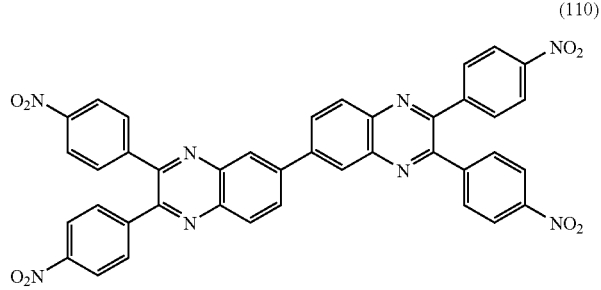
(111)
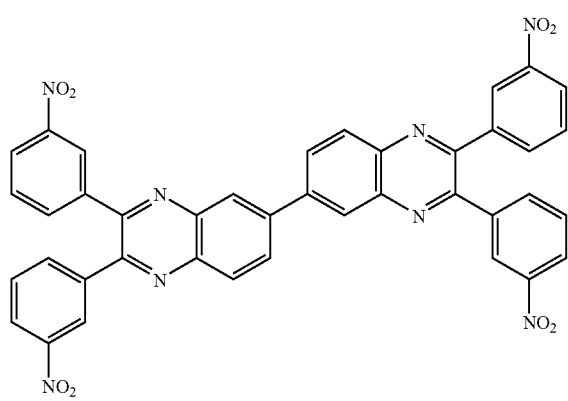
(112)
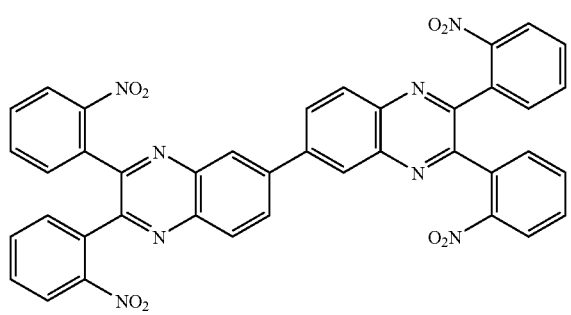
(113)
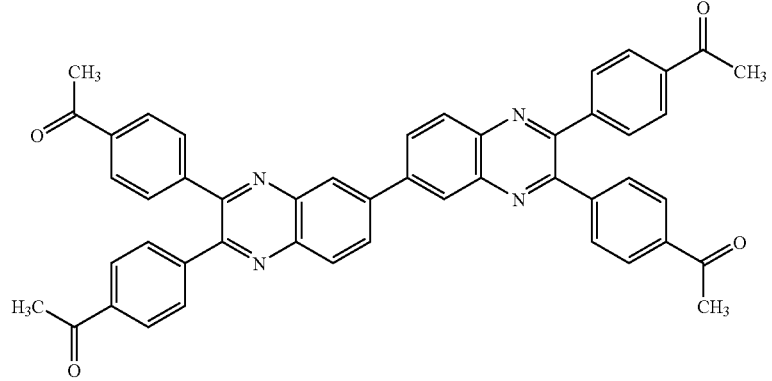
(114)
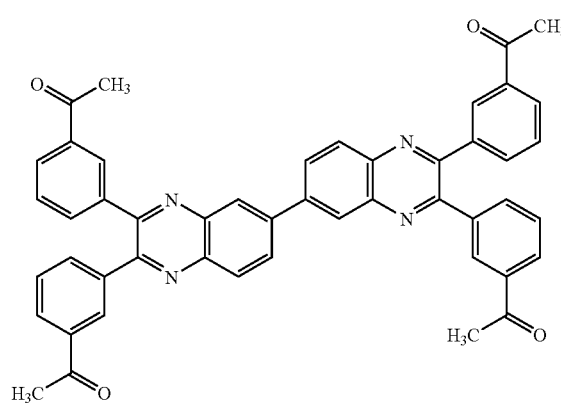
(115)
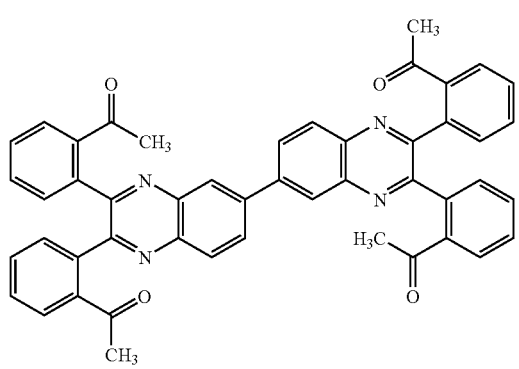

-continued
(116)
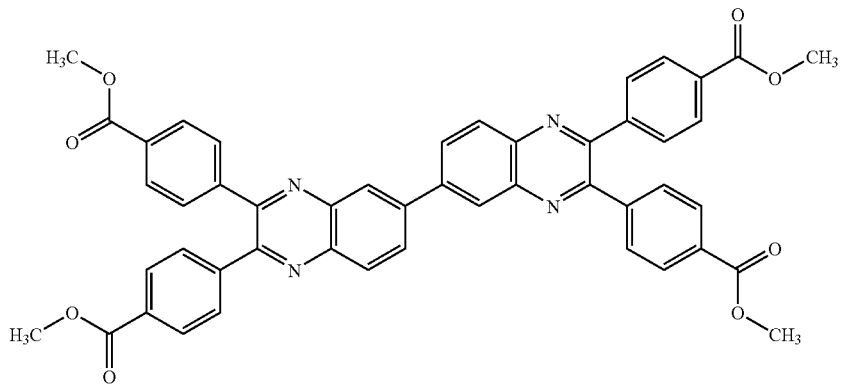
(117)
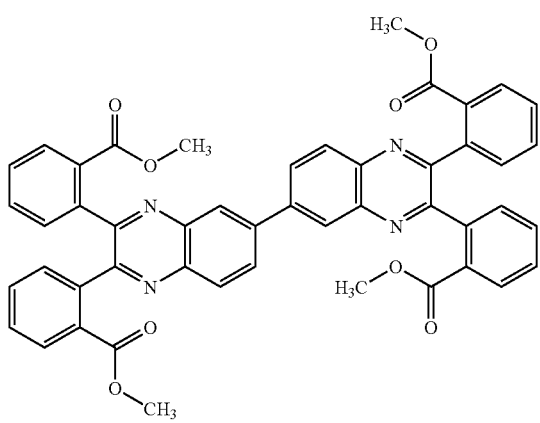
(118)
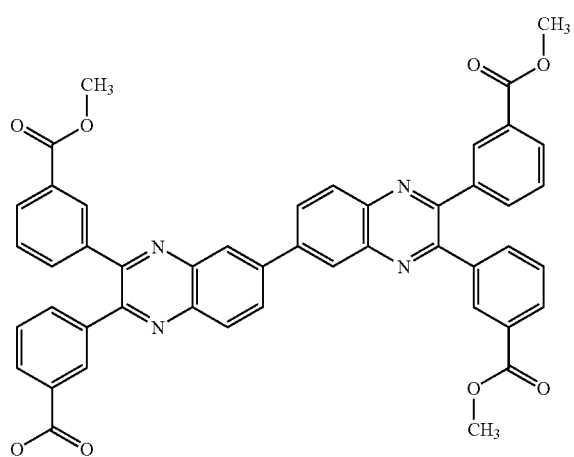
(119)
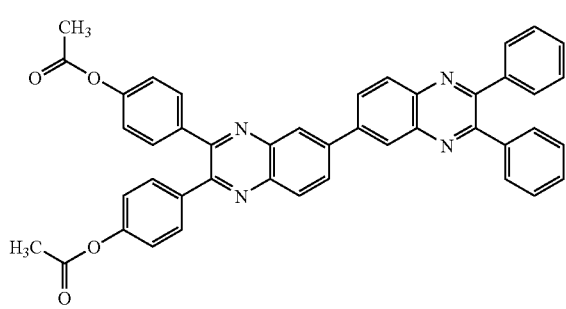
(120)
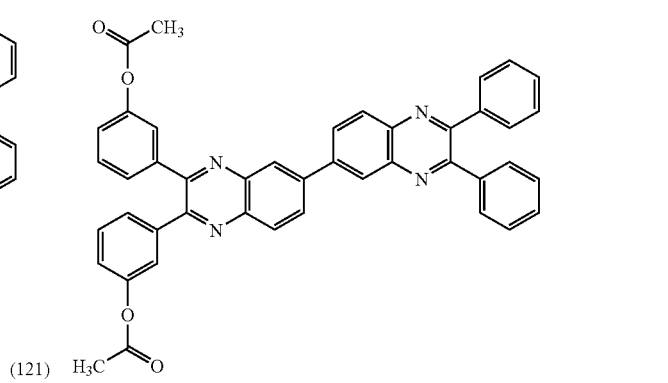
(121)
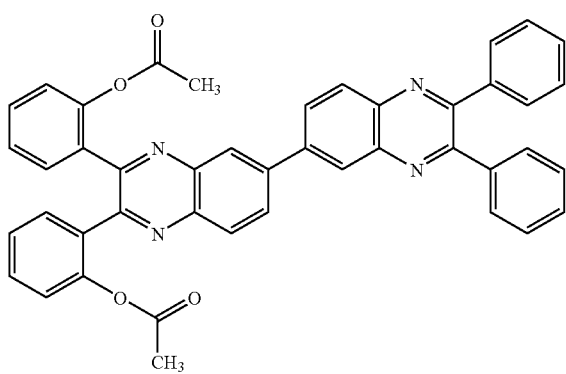

-continued
(122)
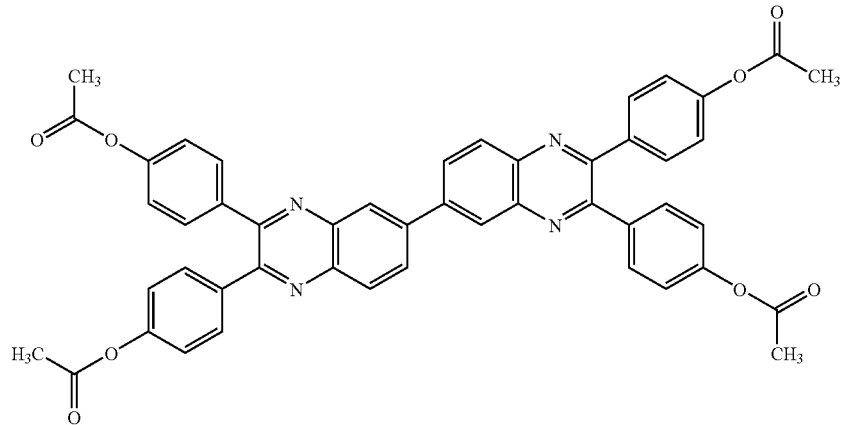
(123)
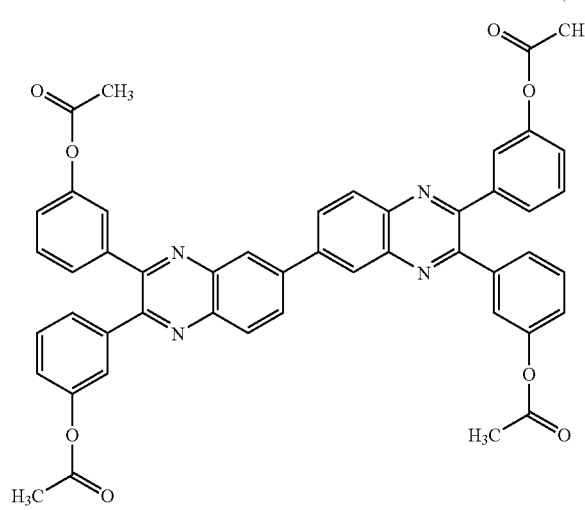
(124)
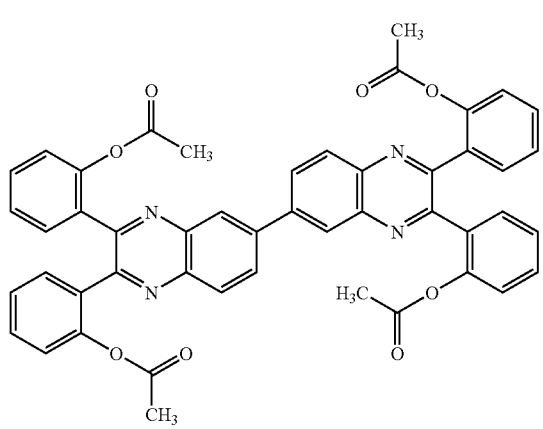
(125)
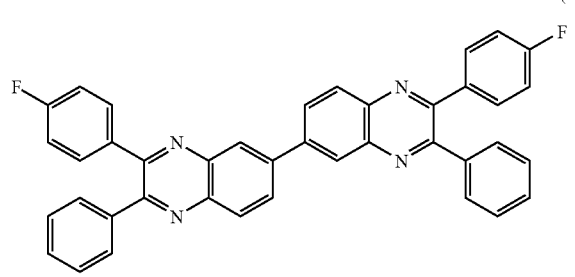
(126)
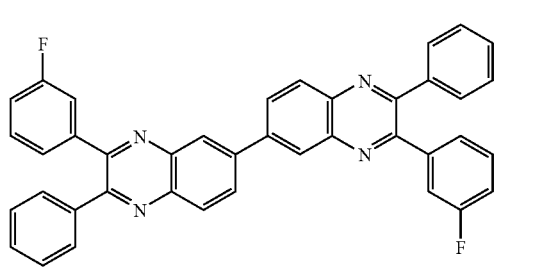
(127)
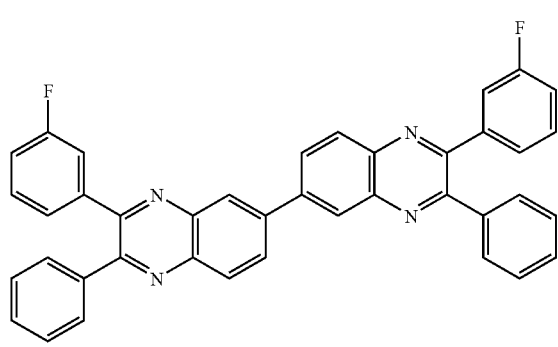
(128)
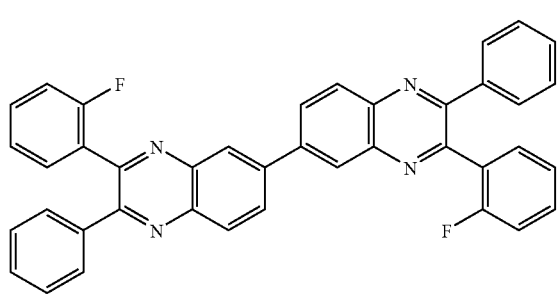

-continued
(129)
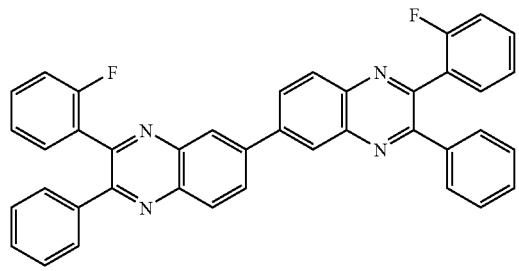
(130)
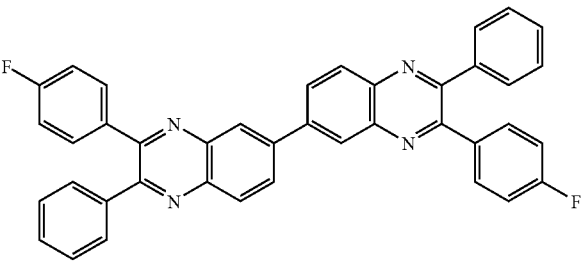
(131)
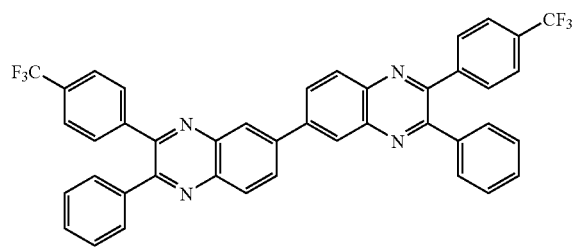
(132)
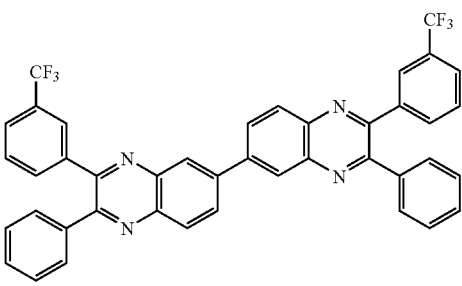
(133)
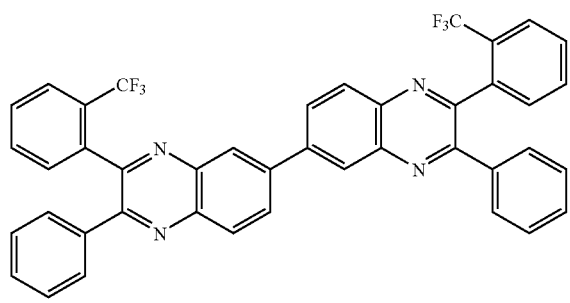
(134)
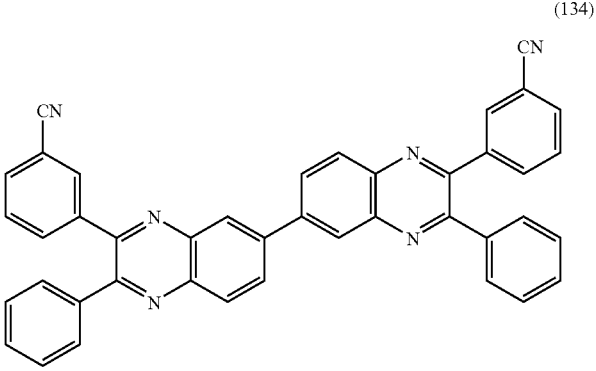
(135)
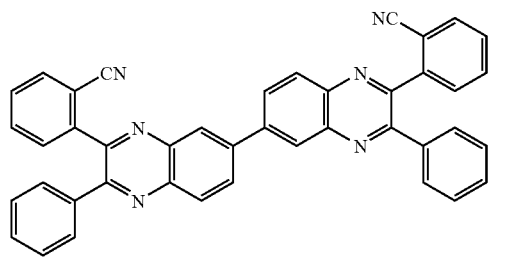
(136)
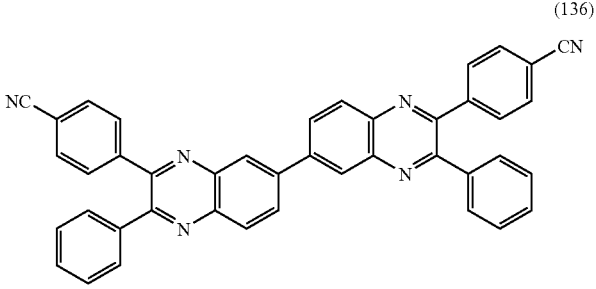
(137)
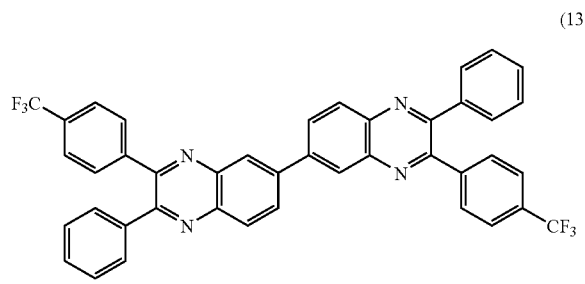
(138)
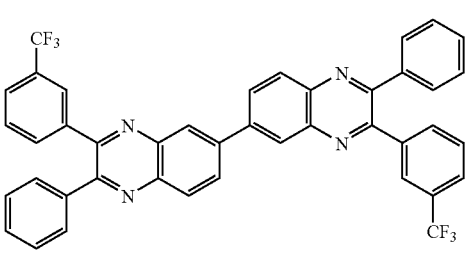

-continued
(139)
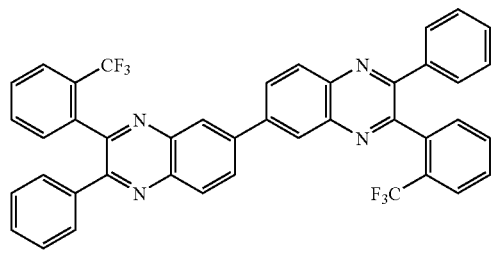
(140)
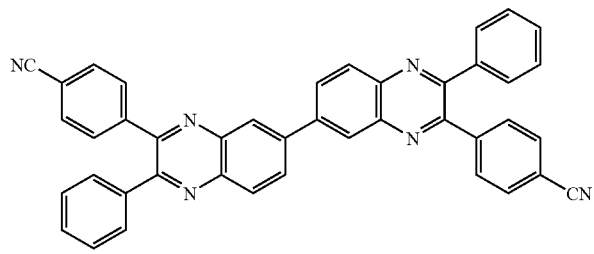
(141)
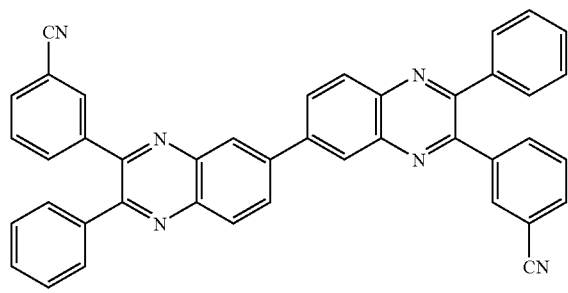
(142)
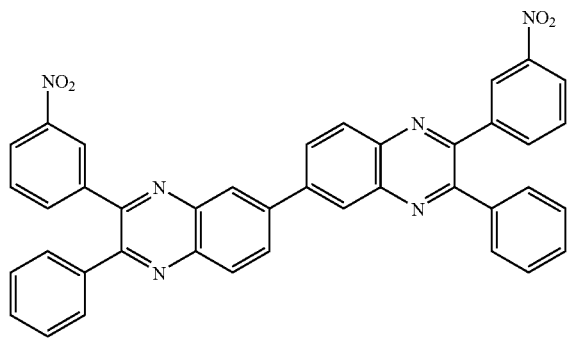
(143)
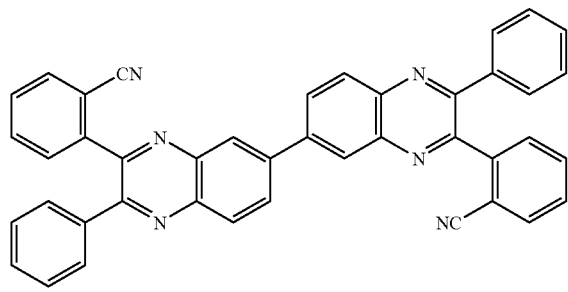
(144)
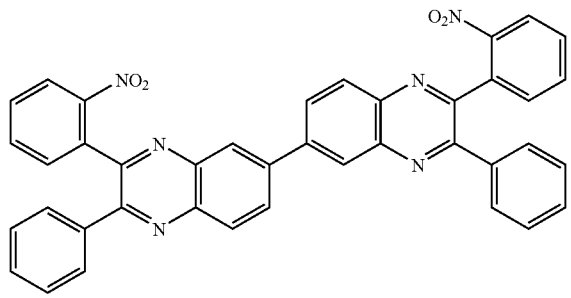
(145)
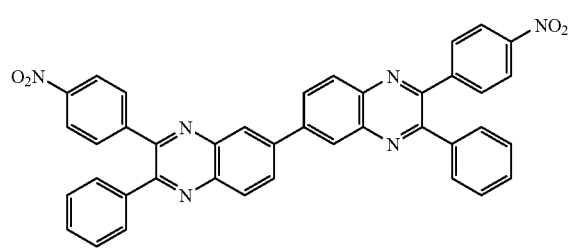
(146)
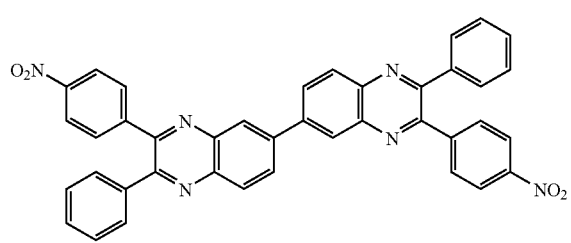
(147)
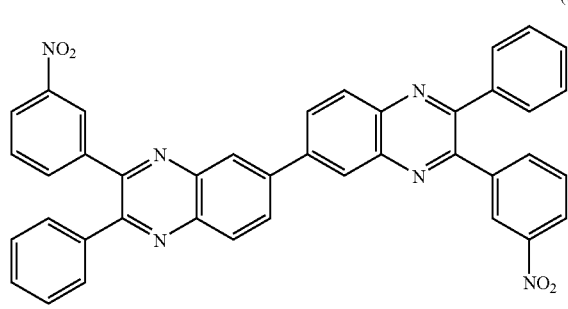
(148)
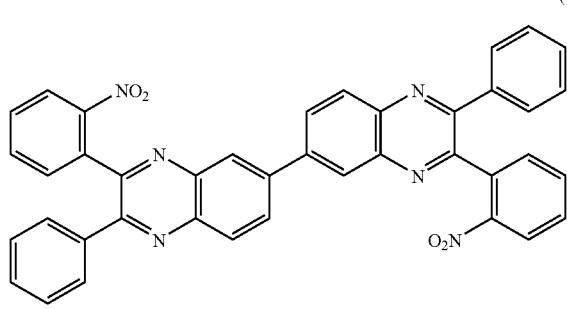

-continued
(149)
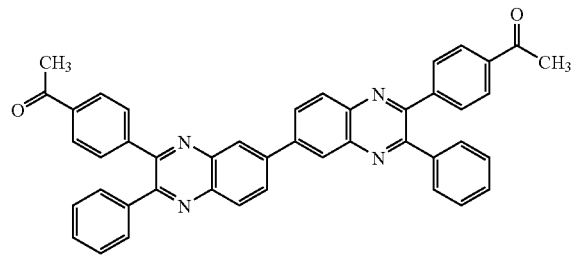
(150)
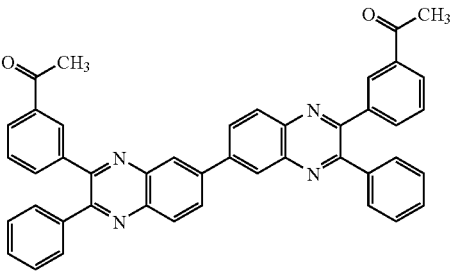
(151)
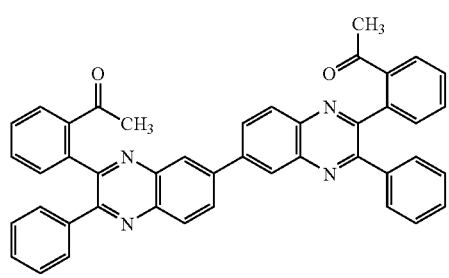
(152)
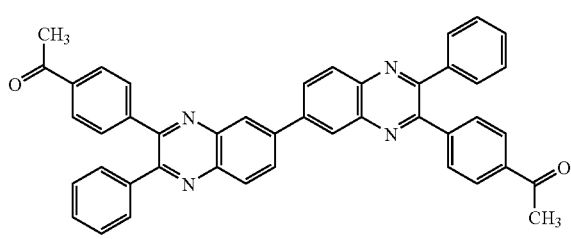
(153)
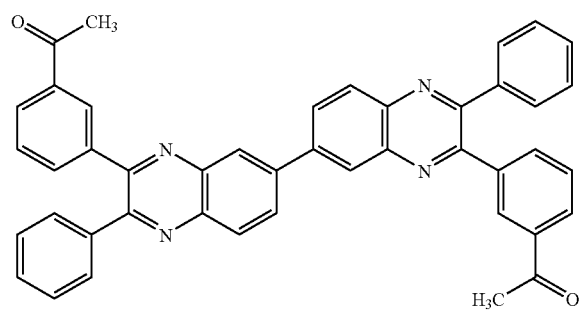
(154)
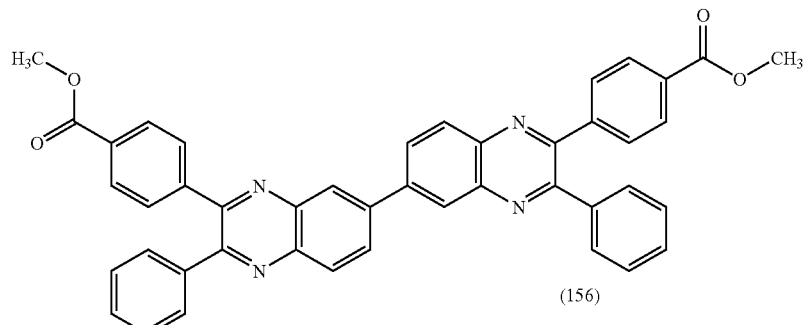
(155)
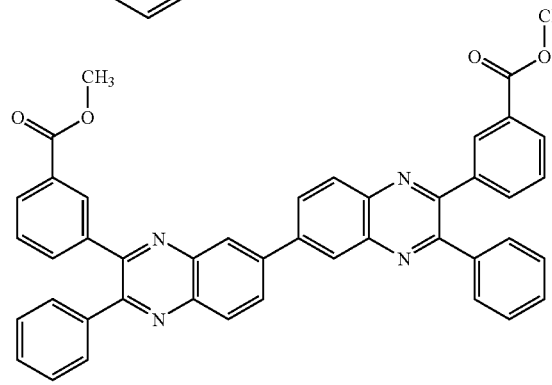
(156)
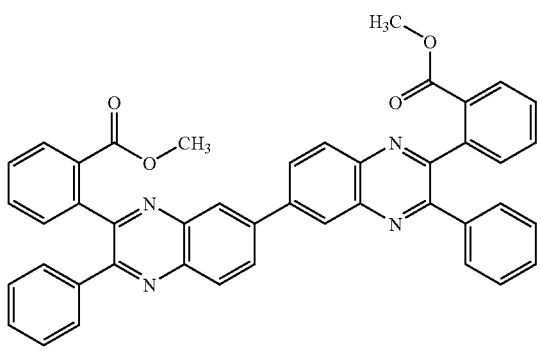
(157)

-continued
(158) 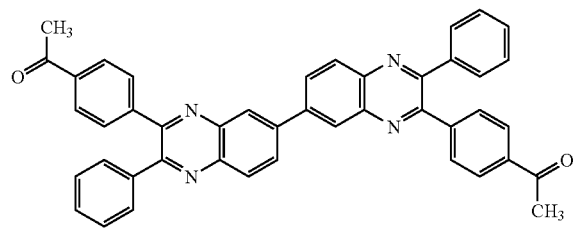
(159) 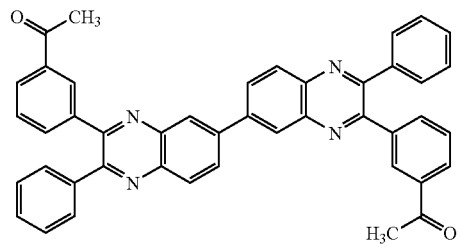
(160) 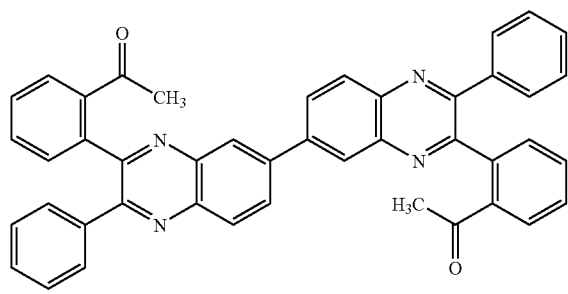
(161) 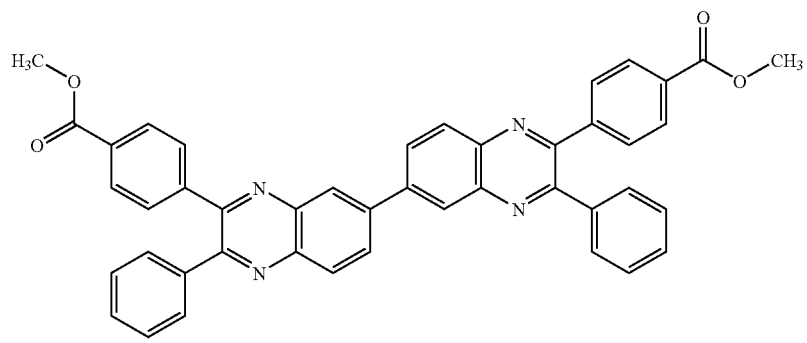
(162) 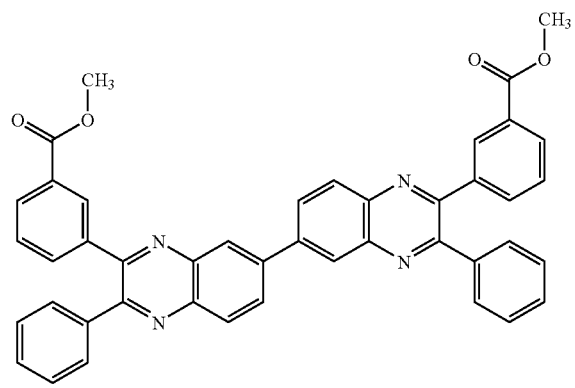
(163) 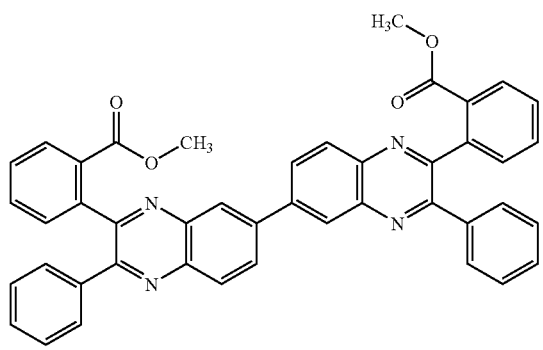

-continued
(164)
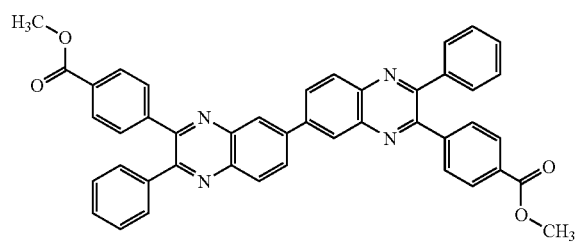
(165)
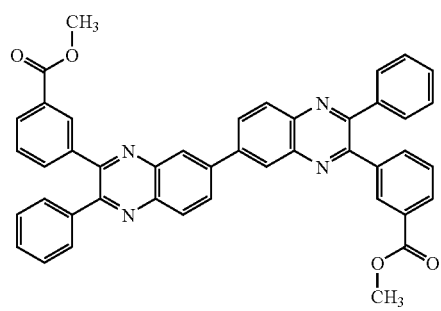
(166)
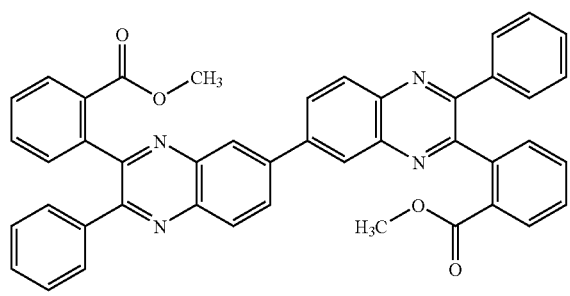
(167)
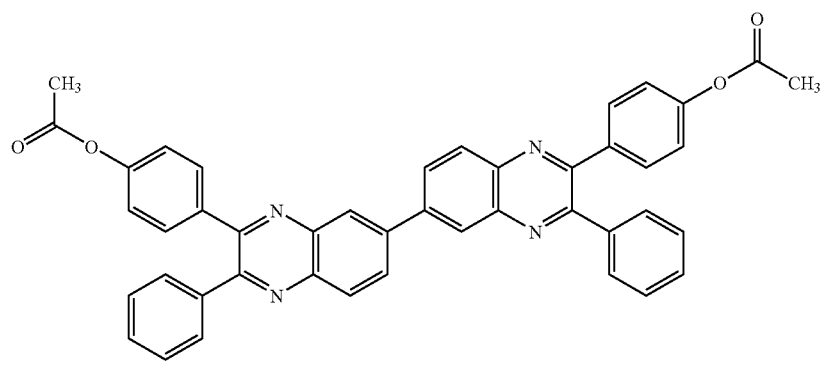
(168)
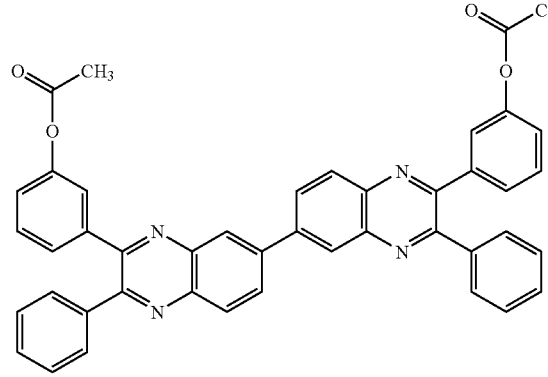
(169)
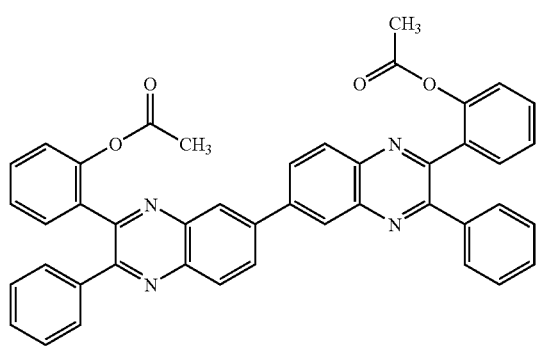

-continued
(170)
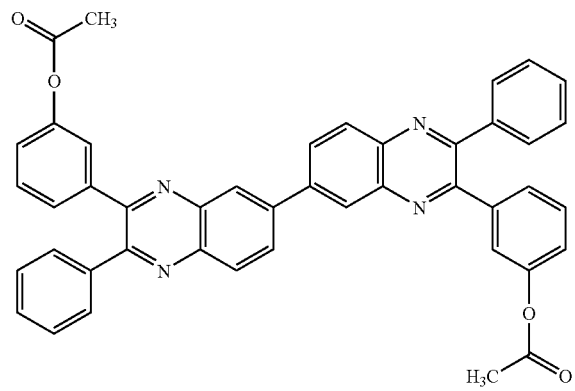
(171)
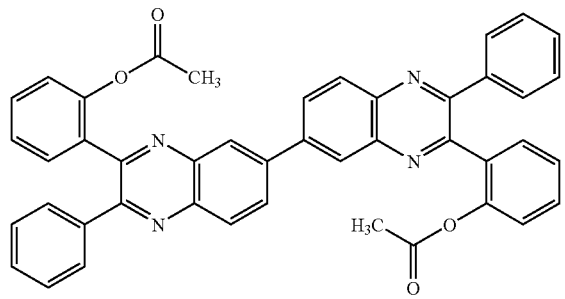
(172)
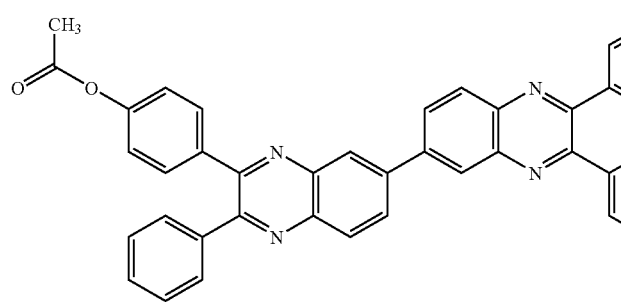
(173)
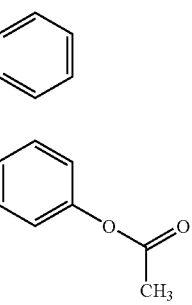
(174)
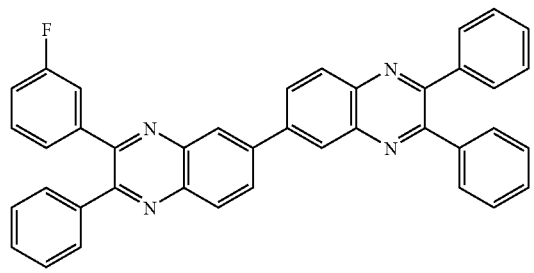
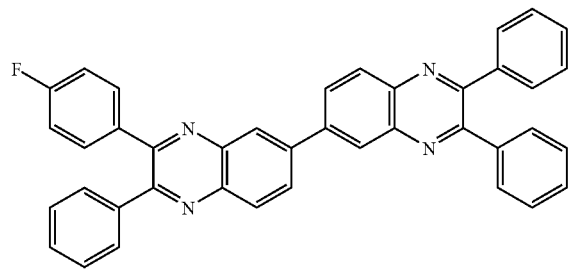
(175)
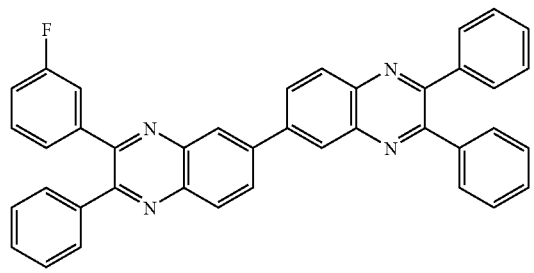
(176)
(177)
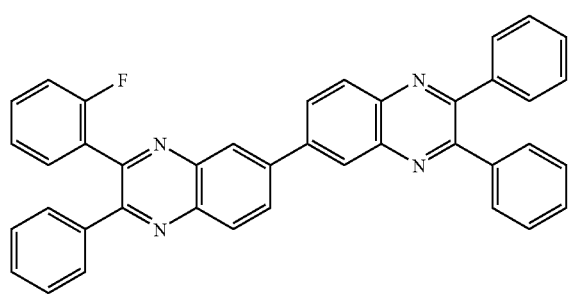
(178)
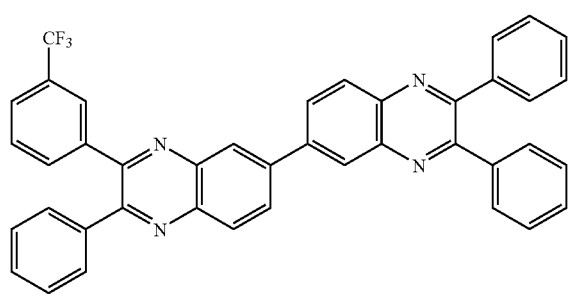
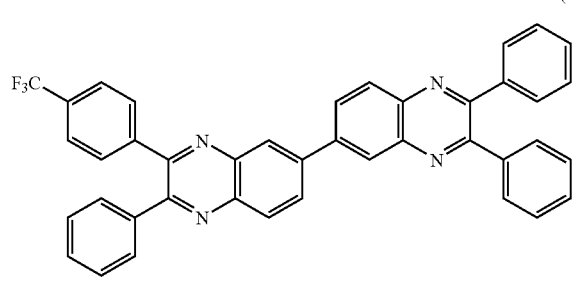
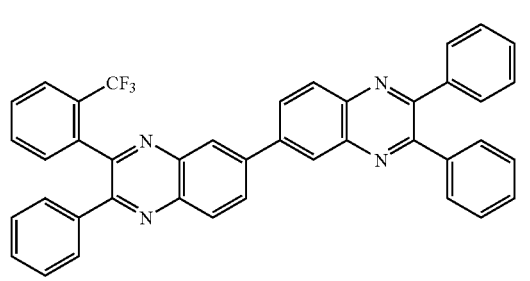

-continued
(179) 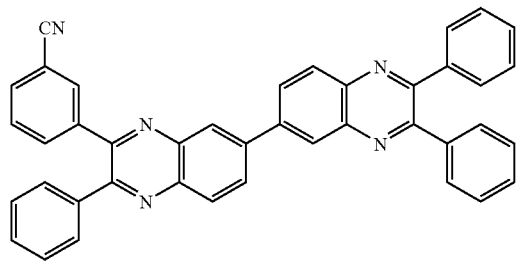
(180) 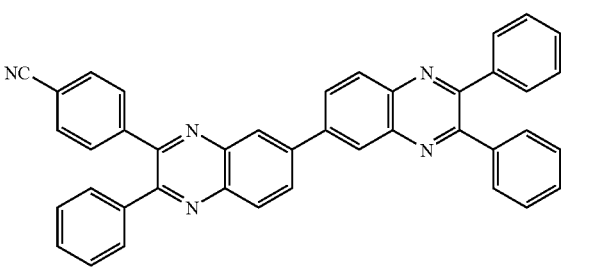
(181) 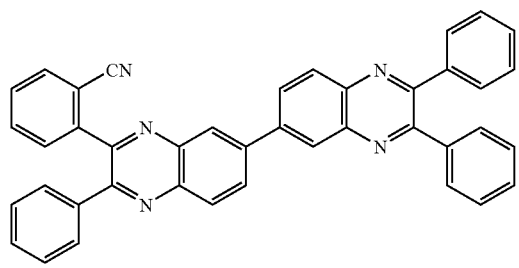
(182) 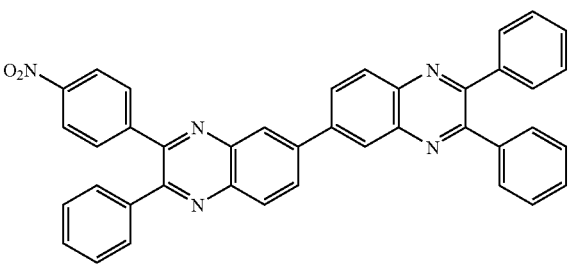
(183) 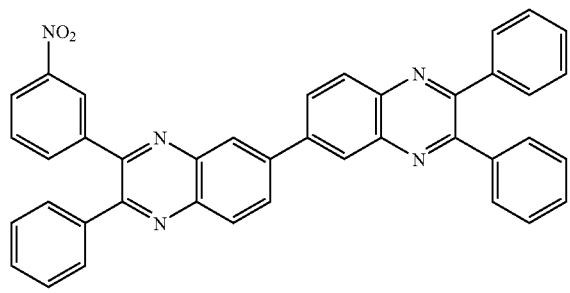
(184) 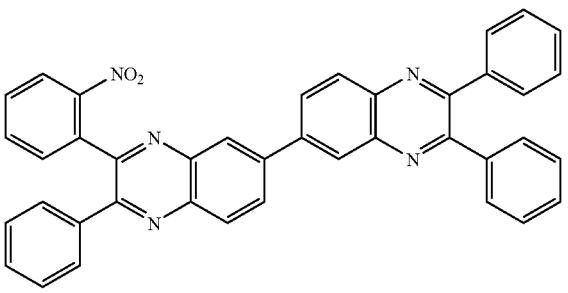
(185) 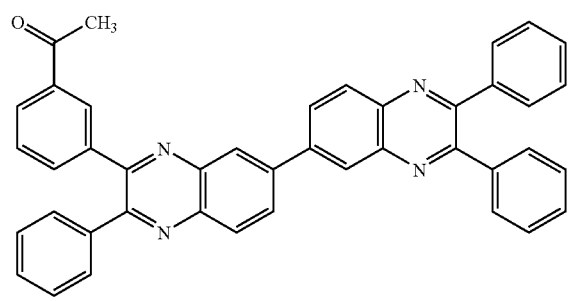
(186) 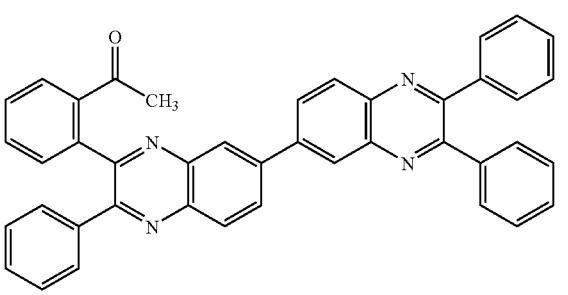
(187) 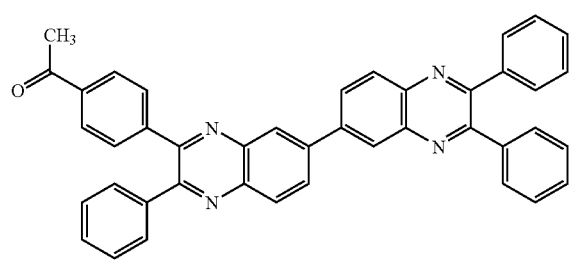
(188) 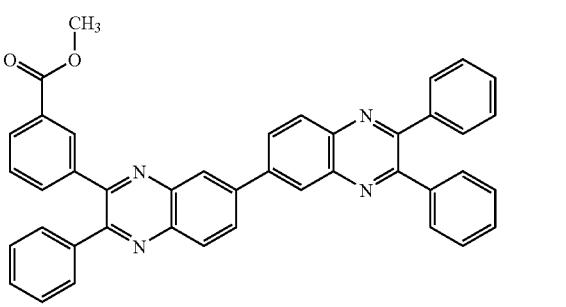

-continued
(189)
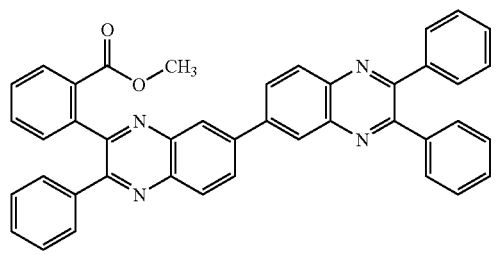
(190)
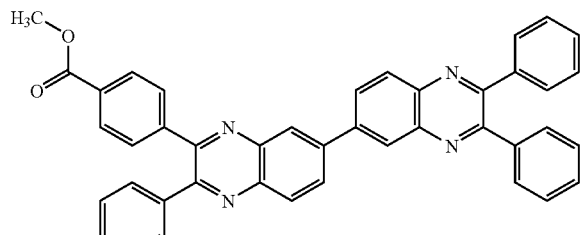
(191)
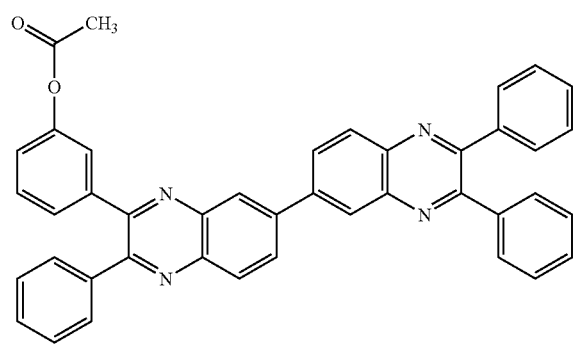
(192)
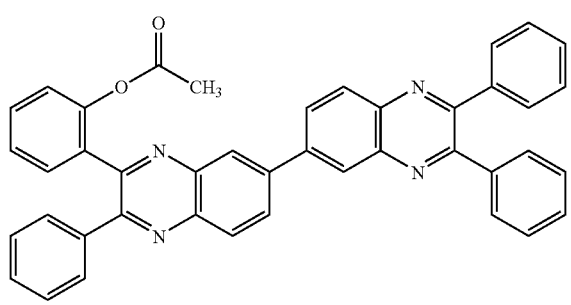
(193)
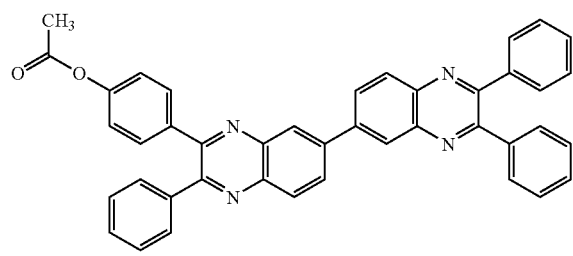
(194)
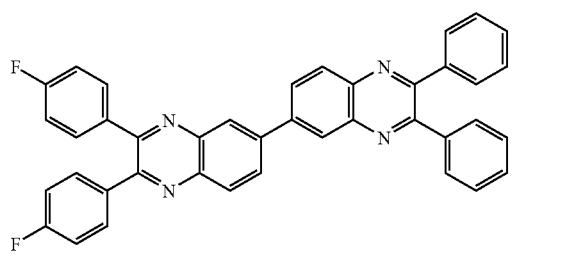
(195)
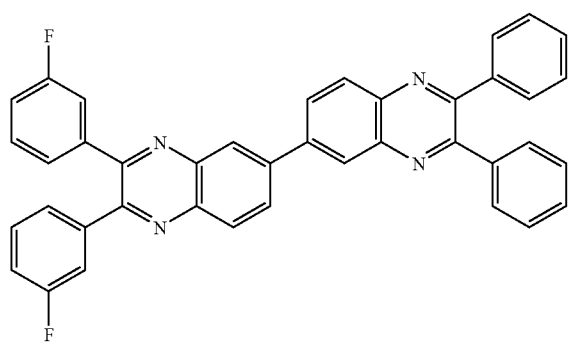
(196)
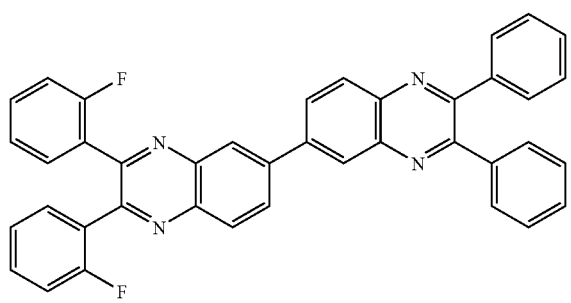
(197)
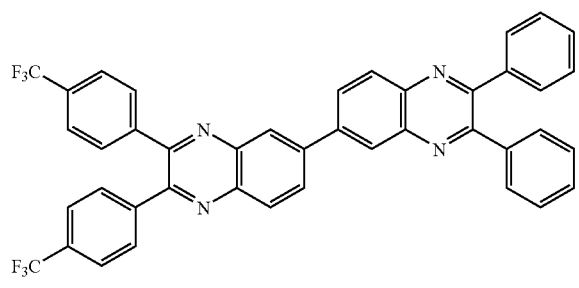
(198)
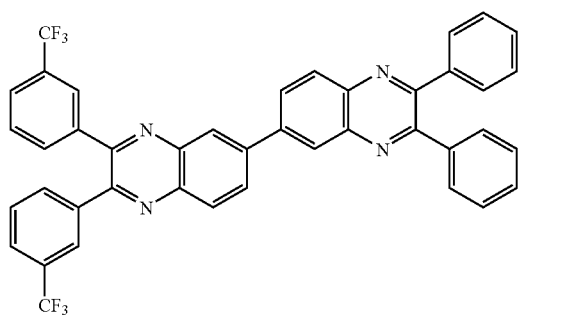

-continued
(199)
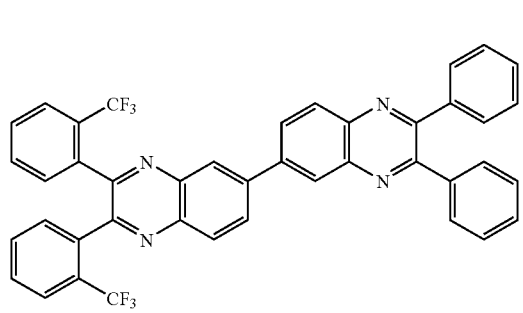
(200)
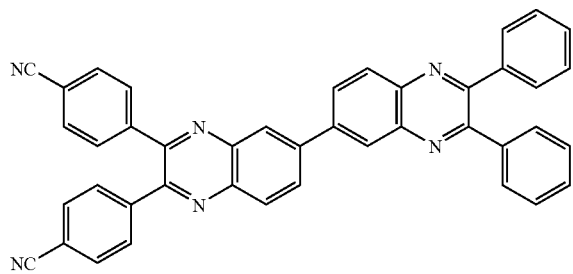
(201)
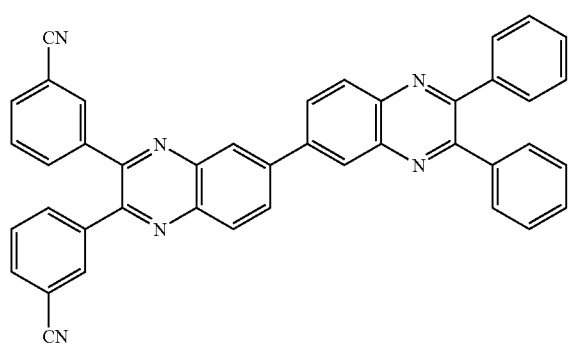
(202)
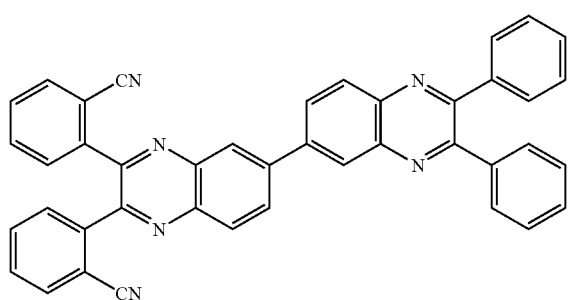
(203)
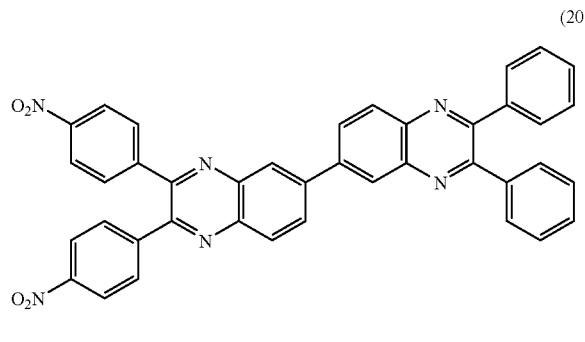
(204)
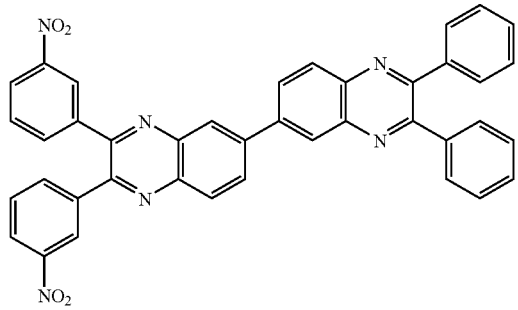
(205)
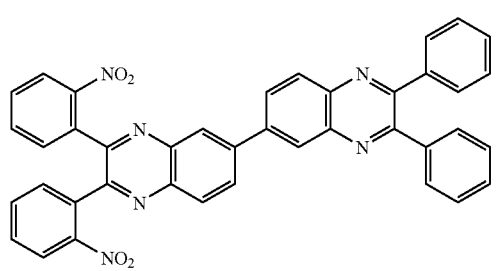
(206)
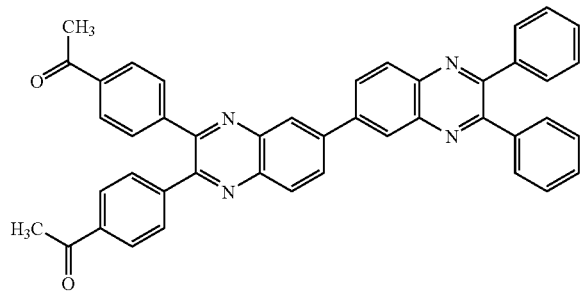

-continued (207) 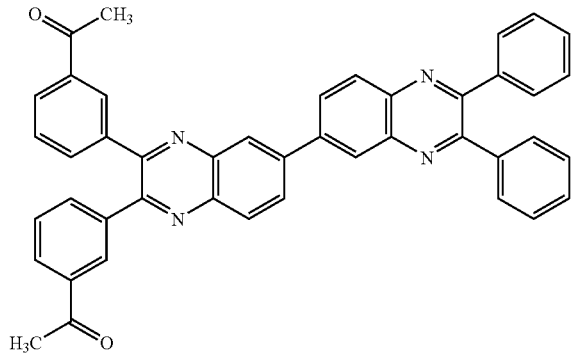

(208) 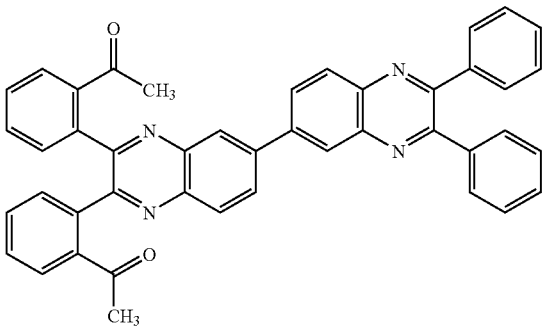

(209) 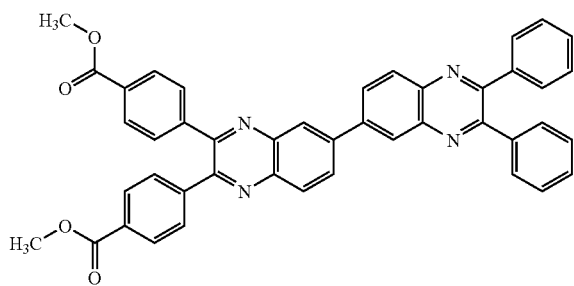

(210) 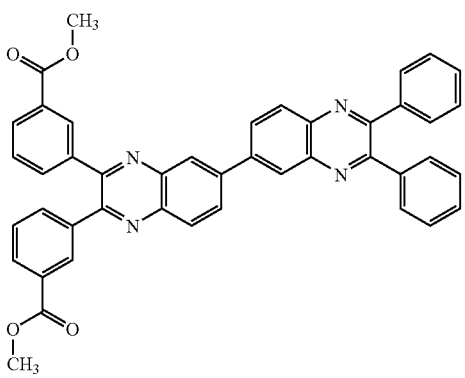

(211) 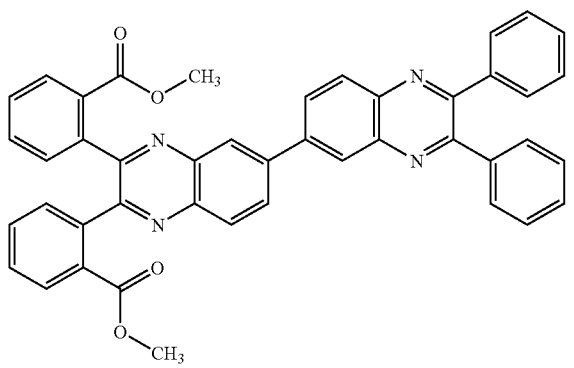

As described above, the LUMO level of the second organic compound is preferably lower than that of the first organic compound by 0.3 eV or more. Thus, depending on the type of the second organic compound to be used, a substance may be selected so as to satisfy the condition as the first organic compound as appropriate. For example, as described below in Examples, the condition can be satisfied by using 2,3,2',3'-tetrakis(4-fluorophenyl)-6,6'-biquinoxaline (abbreviation: FDPQ2) represented by the structural formula (101) or 2,3-bis(4-fluorophenyl)quinoxaline (abbreviation FDPQ) as the second organic compound and using Alq as the first organic compound.

In addition, the thickness of the first layer 214 is preferably within the range of 5 nm to 20 nm, inclusive. If the thickness is too large, electron transfer speed may become too slow, which leads to increase of driving voltage. On the other hand, if the thickness is too small, the electron transfer speed may not be controlled. For this reason, the thickness of the first layer 214 is preferably within the range of 5 nm to 20 nm, inclusive.

The electron-transporting layer 215 is a layer including a high electron-transporting property. For example, as a low molecular organic compound, a metal complex such as Alq, Almq$_3$, BeBq$_2$, BAlq, ZnPBO or ZnBTZ can be used. Further, in addition to such metal complexes, a heterocyclic compound such as PBD, OXD-7, TAZ, TPBI, BPhen or BCP can be used. The above-described substances are mainly substances having an electron mobility of $10^{-6}$ cm$^2$/Vs or higher. Note that any substance which has an electron-transporting property higher than a hole-transporting property can be used as the electron-transporting substance, as well as the above-described substances. In addition, the electron-transporting layer may be a multilayer including two or more layers formed of the above-substances, instead of a single layer.

As the electron-transporting layer 215, a high-molecular compound can be used. For example, poly[(9,9-dihexylfluorene-2,7-diyl)-co-(pyridin-3,5-diyl)] (abbreviation: PF-Py) or poly[(9,9-dioctylfluorene-2,7-diyl)-co-(2,2'-pyridin-6,6'-diyl)] (abbreviation: PF-BPy) can be used.

The electron-injecting layer 216 is a layer including a substance having a high electron-injecting property. As such a substance having a high electron-injecting property, an alkali metal or an alkali earth metal such as lithium fluoride (LiF), cesium fluoride (CsF), calcium fluoride ($CaF_2$) or a compound thereof can be used. An alkali metal or an alkali earth metal or a compound thereof may be contained in a layer made of an electron-transporting substance, for example, a layer in which magnesium (Mg) is contained in Alq, or the like can be used as the electron-injecting layer. When an alkali metal or an alkali earth metal is contained in a layer made of an electron-transporting substance, electrons are injected from the second electrode 202 efficiently, which is preferable.

The second electrode 202 is preferably formed using a material with a low work function (i.e., 3.8 eV or lower) such as metals, alloys, electrically conductive compounds, or a mixture of them. Specific examples of such a cathode material include an element belonging to Group 1 or 2 of the periodic table, i.e., alkali metals such a lithium (Li) and cesium (Cs) and alkaline earth metals such as magnesium (Mg), calcium (Ca), and strontium (Sr); alloys of them (e.g., MgAg and AlLi); rare earth metals such as europium (Eu) and ytterbium (Yb); alloys of them; and the like. A film made of an alkali metal, an alkaline earth metal, or an alloy of them can be formed by a vacuum evaporation method. Further, a film made of an alloy of an alkali metal or an alkaline earth metal can be formed by a sputtering method. It is also possible to deposit a silver paste or the like by an inkjet method or the like.

As the electron-injecting layer 216, a layer in which a donor substance such as an alkali metal, an alkali earth metal, or a rare earth metal is contained in a layer formed of an electron-transporting substance is used. In this case, regardless of work function, various electrically conductive compounds such as Al, Ag, ITO, or indium tin oxide including silicon or silicon oxide can be used as the second electrode 202. Such electrically conductive compounds can be formed by a sputtering method, an inkjet method, a spin coating method or the like. Note that an organic compound such as tetrathiafulvalene (abbreviation: TTF) can be used as a donor substance.

Figure 2A:
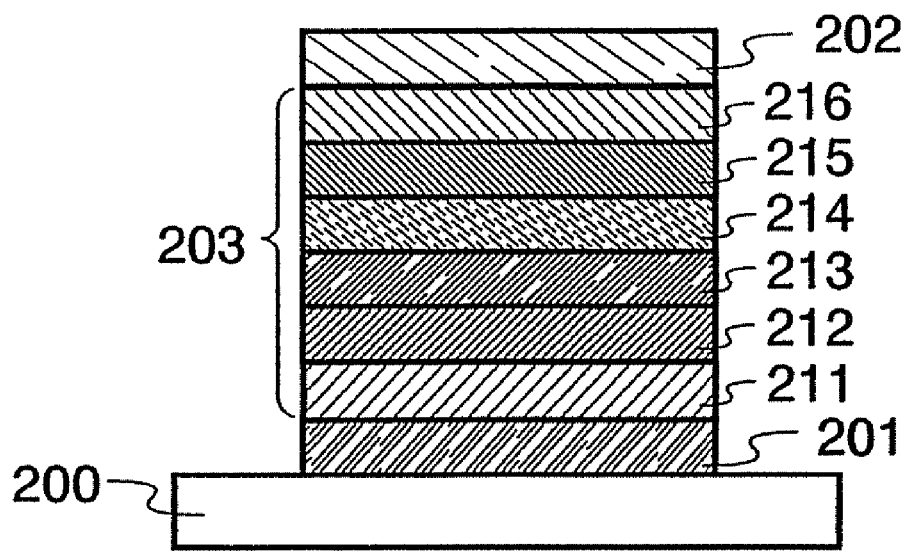
FIGS. 2A and 2B each show a light-emitting element according to an aspect of the present invention.
Figure 2B:
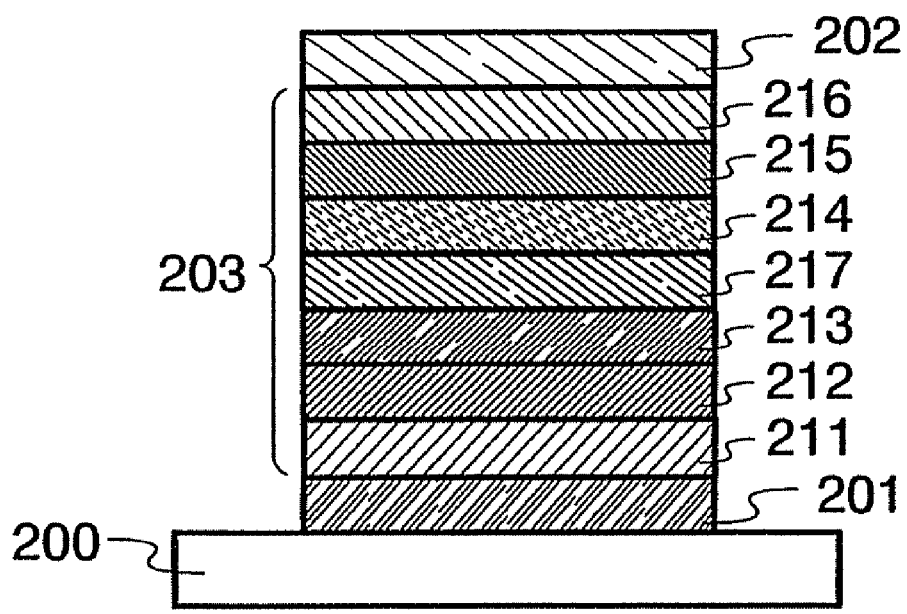

For example, as shown in FIG. 2B, a layer 217 including a substance having a high electron-transporting property may be formed between the second layer 213 serving as a light-emitting layer and the first layer 214 as a layer to control electron transfer.

Note that more preferably, as shown in FIG. 2A, the first layer 214 is preferably formed so as to be in contact with the second layer 213. In this case, the effect of emission with excellent color purity is remarkable. In addition, by making the first layer 214 and the second layer 213 in contact with each other, electron-injecting to the second layer 213 serving as a light-emitting layer can be directly controlled, and change over time of carrier balance in the light-emitting layer can be suppressed, which resulting in large increase of lifetime of the element. In addition, since the layer 217 including a high electron-transporting property is not formed, process is simplified.

Note that when the first layer 214 and the second layer 213 are in contact with each other, the first organic compound included in the first layer 214 and an organic compound a large amount of which is included in the second layer 213 are preferably different from each other. In particular, when the second layer 213 includes a substance (a third organic compound) to disperse a substance having a high light-emitting property and a light-emitting substance, the third organic compound and the first organic compound are preferably organic compounds. In such a structure, electron transfer from the first layer 214 to the second layer 213 is suppressed also between the first organic compound and the third organic compound, and thus an effect of providing a layer to control electron transfer becomes stronger.

A manufacturing method of a light-emitting element will now be described. As a method forming the EL layer 203, various methods can be used regardless of a dry process or a wet process. For example, a vacuum evaporation method, an inkjet method, a spin coating method, or the like can be used. Further, different deposition methods may be used for different electrodes or different layers.

For example, among the above-described materials, a high molecular compound may be selected to form the EL layer by a wet process. Alternatively, a low molecular organic compound may be selected to form the EL layer by a wet process. Further, it is also possible to form the EL layer by selecting a low molecular organic compound and using a dry process such as a vacuum evaporation method.

Similarly, the electrodes can be formed by a wet process such as a sol-gel process or by a wet process with a paste of a metal material. Alternatively, the electrodes can be formed by a dry process such as a sputtering method or a vacuum evaporation method.

A specific method for forming the light-emitting element will now be described. In the case where the light-emitting element of the present invention is applied to a display device and its light-emitting layer is selectively deposited according to each color, each light-emitting layer is preferably formed by a wet process. When the light-emitting layer is formed by an inkjet method, selective deposition of the light-emitting layer for each color can be easily performed even when a large substrate is used.

For example, the structure shown in FIG. 2A can be obtained by the steps of: forming the first electrode 201 by a sputtering method which is a dry process; forming the hole-injecting layer 211 by an inkjet method or a spin coating method which is a wet process; forming the hole-transporting layer 212 by a vacuum evaporation method which is a dry process; forming the second layer 213 by an inkjet method which is a wet process; forming the first layer 214 by a co-deposition method which is a dry process; forming the electron-transporting layer 215 and the electron-injecting layer 216 by a vacuum evaporation method which is a dry process; and forming the second electrode 202 by an inkjet method or a spin coating method which is a wet process. Alternatively, the structure may be obtained by the steps of: forming the first electrode 201 by an inkjet method which is a wet process; forming the hole-injecting layer 211 by a vacuum evaporation method which is a dry process; forming the hole-transporting layer 212 by an inkjet method or a spin coating method which is a wet process; forming the second layer 213 by an inkjet method which is a wet process; forming the first layer 214 by an inkjet method or a spin coating method which is a wet process, forming the electron-transporting layer 215 and the electron-injecting layer 216 by an inkjet method or a spin coating method which is a wet process; and forming the second electrode 202 by an inkjet method or a spin coating method which is a wet process. Note that the deposition methods are not limited to the above methods, and a wet process and a dry process may be combined as appropriate.

For example, preferably, the structure shown in FIG. 2A can be obtained by the steps of: forming the first electrode 201 by a sputtering method which is a dry process; forming the hole-injecting layer 211 and the hole-transporting layer 212 by an inkjet method or a spin coating method which is a wet process; forming the second layer 213 which is a light-emitting layer by an inkjet method which is a wet process; forming the first layer 214 by a co-deposition method which is a dry process; forming the electron-transporting layer 215 and the electron-injecting layer 216 by a vacuum evaporation method which is a dry process; and forming the second electrode 202 by a vacuum evaporation method which is a dry process. That is, it is possible to form the hole-injecting layer 211 to the second layer 213 by wet processes on the substrate having the first electrode 201 which is formed in advance in a desired shape, and form the first layer 214 to the second electrode 202 thereon by dry processes. By this method, the hole-injecting layer 211 to the second layer 213 can be formed at atmospheric pressure and the second layer 213 can be selectively deposited according to each color with ease. In addition, the first layer 214 to the second electrode 202 can be consecutively formed in vacuum. Therefore, the process can be simplified and productivity can be improved. The process will be exemplarily described below. First, PEDOT/PSS is deposited as the hole-injecting layer 211 on the first electrode 201. Since PEDOT/PSS is soluble in water, it can be deposited as an aqueous solution by a spin coating method, an inkjet method, or the like. The hole-transporting layer 212 is not provided but the second layer 213 is provided as the light-emitting layer on the hole-injecting layer 211. The second layer can be formed by an inkjet method, using a solution in which a light-emitting substance is dissolved in a solvent (e.g., toluene, dodecylbenzene, or a mixed solvent of dodecylbenzene and tetralin) in which the hole-injecting layer 211 (PEDOT/PSS) that is already formed will not be dissolved. Next, the first layer 214 is formed over the second layer 213. When the first layer 214 is formed by a wet process, the first layer should be formed using a solvent in which the hole-injecting layer 211 and the second layer 213 that are already formed will not be dissolved. In that case, the selection range of solvents is limited. Therefore, using a dry process is easier to form the first layer 214. Thus, by consecutively forming the first layer 214 to the second electrode 202 in vacuum by a vacuum evaporation method which is a dry process, the process can be simplified.

In the light-emitting element of the present invention having the above structure, current flows due to a potential difference generated between the first electrode 201 and the second electrode 202, and thereby holes and electrons are recombined in the EL layer 203 so that light is emitted.

Figure 4A:
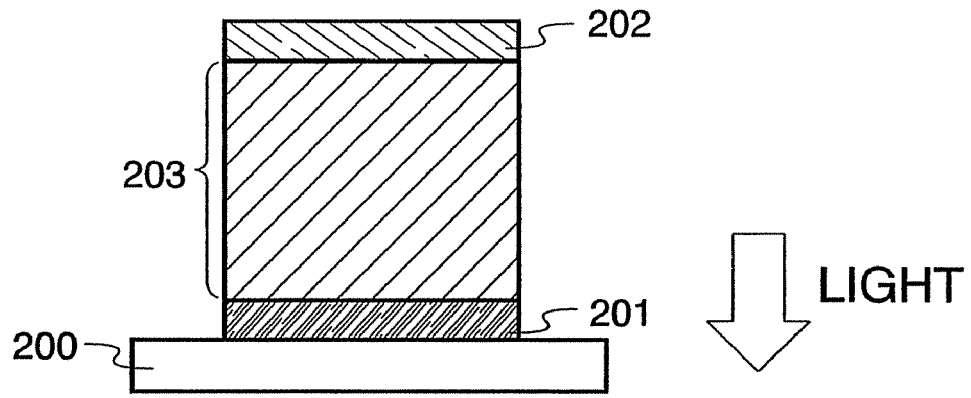
FIGS. 4A to 4C each show a light-emitting element according to an aspect of the present invention.
Figure 4B:
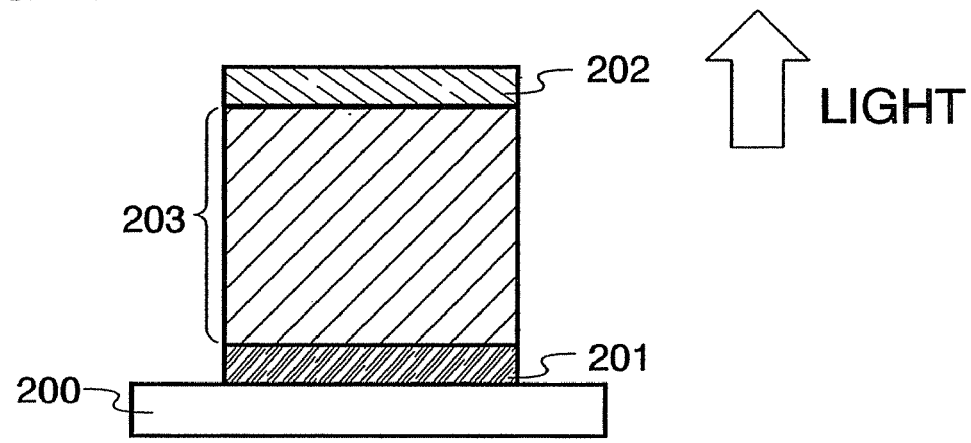
Figure 4C:
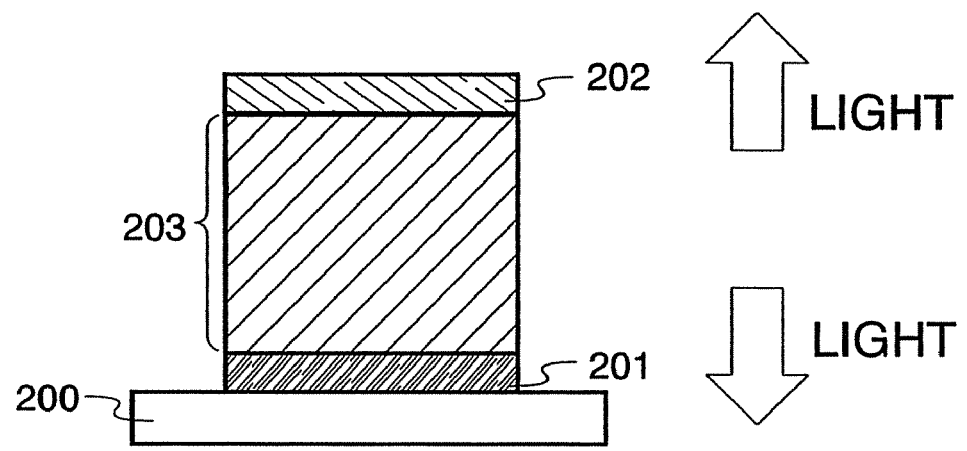

Light is extracted outside through one or both of the first electrode 201 and the second electrode 202. Therefore, one or both of the first electrode 201 and the second electrode 202 is a light-transmitting electrode. When only the first electrode 201 is a light-transmitting electrode, light is extracted from the substrate 200 side through the first electrode 201 as shown in FIG. 4A. Meanwhile, when only the second electrode 202 is a light-transmitting electrode, light is extracted from a side opposite to the substrate 200 side through the second electrode 202 as shown in FIG. 4B. When both of the first electrode 201 and the second electrode 202 are light-transmitting electrodes, light is extracted from both the substrate 200 side and the side opposite to the substrate 200 side through the first electrode 201 and the second electrode 202 as shown in FIG. 4C.

Figure 3A:
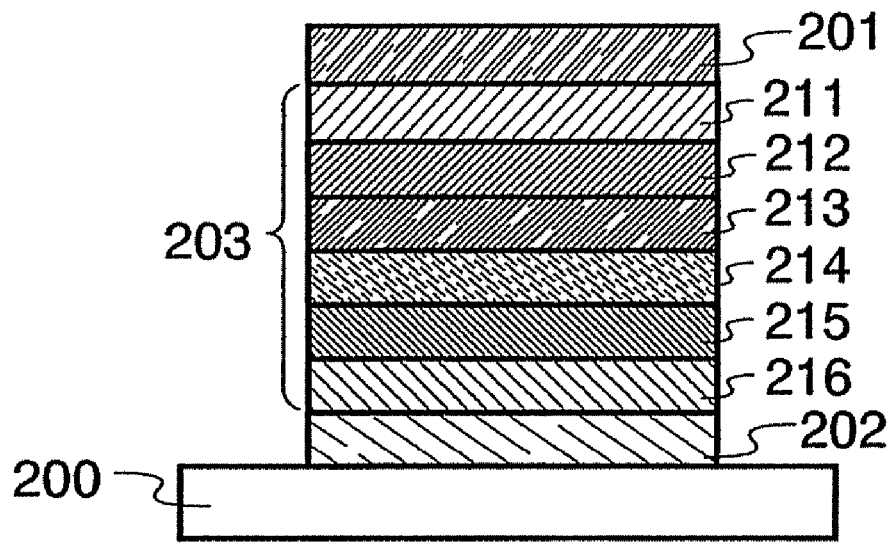
FIGS. 3A and 3B each show a light-emitting element according to an aspect of the present invention.

FIGS. 2A and 2B show structures in which the first electrode 201 is formed over the substrate 200, but the second electrode 202 may be formed over the substrate 200. In other words, as shown in FIG. 3A, over the substrate 200, the second electrode 202 serving as a cathode, the EL layer 203, and the first electrode 201 serving as an anode are stacked sequentially. The EL layer 203, similarly in FIGS. 2A and 2B, includes the electron-injecting layer 216, the electron-transporting layer 215, the first layer 214, the second layer 213, the hole-transporting layer 212 and the hole-injecting layer 211. In addition, as shown in FIG. 3B, a layer 217 including a substance having high electron-transporting property may be provided, which is similar to that in FIG. 2B.

Figure 3B:
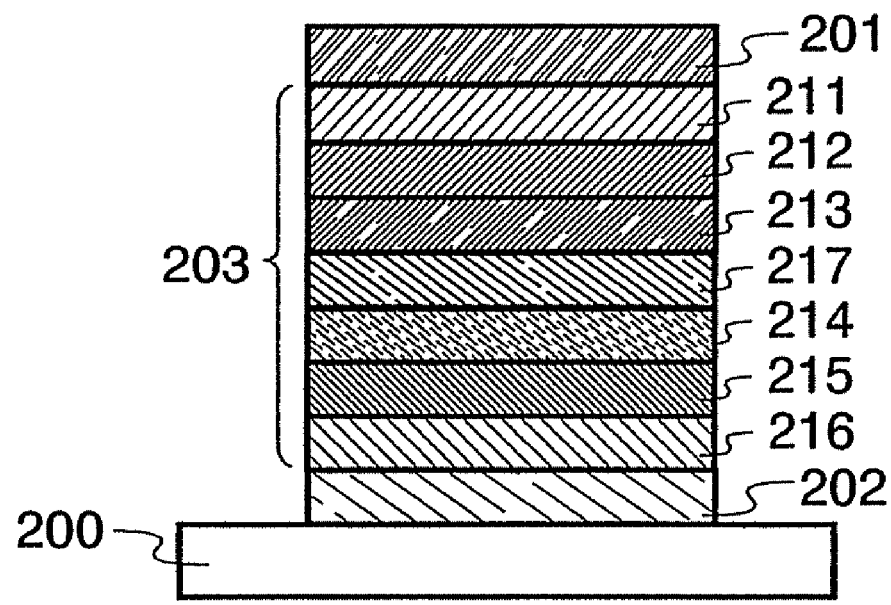

Meanwhile, structures shown in FIGS. 3A and 3B can be formed by the following steps: forming the second electrode 202 by a sputtering method or a vacuum evaporation method which is a dry process; forming the electron-injecting layer 216 and the electron-transporting layer 215 by a vacuum evaporation method which is a dry process; forming the first layer 214 by a co-deposition method which is a dry process; forming the second layer 213 by an inkjet method which is a wet process; forming the hole-transporting layer 212 and the hole-injecting layer 211 by an inkjet method or a spin coating method which is a wet process; and forming the first electrode 201 by an inkjet method or a spin coating method which is a wet process. By this method, the second electrode 202 to the first layer 214 can be consecutively formed in vacuum by dry processes, and the second layer 213 to the first electrode 201 can be formed at atmospheric pressure. Therefore, the process can be simplified and productivity can be improved.

In this embodiment mode, the light-emitting element is formed over a substrate made of glass, plastic, or the like. When a plurality of such light-emitting elements are formed over one substrate, a passive matrix light-emitting device can be formed. In addition, it is possible to form, for example, thin film transistors (TFTs) over a substrate made of glass, plastic, or the like and form light-emitting elements on electrodes that are electrically connected to the TFTs. Accordingly, an active matrix light-emitting device in which drive of the light-emitting elements is controlled with the TFTs can be formed. Note that the structure of the TFTs is not particularly limited. Either staggered TFTs or inversely staggered TFTs may be employed. In addition, a driver circuit formed on a TFT substrate may be constructed from both n-channel and p-channel TFTs or from either n-channel TFTs or p-channel TFTs. Further, the crystallinity of a semiconductor film used for forming the TFTs is not specifically limited. Either an amorphous semiconductor film or a crystalline semiconductor film may be used.

A light-emitting element of the present invention as described above includes a layer for controlling the movement of electrons (the first layer as described above). The first layer contains at least two kinds of substances. Therefore, by controlling the combination of substances, the mixture ratio thereof, the thickness of the layer, or the like, carrier balance can be precisely controlled.

Further, since the carrier balance can be controlled by controlling the combination of compounds, the mixture ratio thereof, the thickness of the layer, or the like, carrier balance can be more easily controlled than in a conventional light-emitting element. That is, the movement of carriers can be controlled not by changing the physical properties of the material but by controlling the mixture ratio, the thickness of the layer, and the like.

Thus, it becomes possible to prevent excessive electrons from being injected and also prevent electrons from penetrating the light-emitting layer and reaching the hole-transporting layer or the hole-injecting layer. Therefore, a decrease in luminous efficiency over time can be suppressed. That is, a long-lifetime light-emitting element can be obtained.

Among two or more kinds of compounds contained in the first layer, the second organic compound included in less weight percent than the first organic compound is used for controlling the movement of electrons. Therefore, the movement of electrons can be controlled with the component that has the lowest weight percent among the components contained in the first layer. Thus, a long-lifetime light-emitting element which does not easily deteriorate over time can be obtained. In the present invention, the change of carrier balance hardly occurs, as compared with the case where the movement of carriers is controlled by a single substance. For example, when the movement of carriers is controlled by a layer made of a single substance, the balance of the whole layer is changed by a partial change in morphology or by partial crystallization. Therefore, such a light-emitting element will easily deteriorate over time. However, as shown in this embodiment mode, when the movement of carriers is controlled with the component that has the lowest weight percent of all the components contained in the first layer, it is possible to reduce the effects of morphological change, crystallization, aggregation, or the like, and thereby deterioration over time can be suppressed. Therefore, a long-lifetime light-emitting element whose luminous efficiency will not easily decrease over time can be obtained.

Embodiment Mode 2

Embodiment Mode 2 will describe a synthesis method of the above quinoxaline derivative of the present invention. A synthesis method is described below, using the quinoxaline derivative represented by the general formula (1) as an example.

The quinoxaline derivative represented by the general formula (1) can be synthesized from 3,3'-diaminobenzidine, α-diketone A represented by a general formula (3) and α-diketone B represented by a general formula (4).

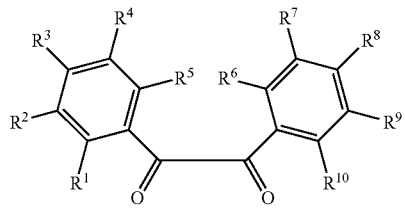

(3)

Note that at least one of $R^1$ to $R^{10}$ is any of a fluoro group, a cyano group, a trifluoromethyl group, a nitro group, an acyl group and an acyloxy group, and the others are hydrogen.

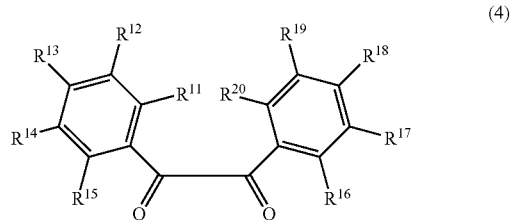

(4)

Note that at least one of $R^{11}$ to $R^{20}$ is any of a fluoro group, a cyano group, a trifluoromethyl group, a nitro group, an acyl group and an acyloxy group, and the others are hydrogen.

In other words, as represented in a synthesis scheme (a), 3,3'-diaminobenzidine, α-diketone A represented by the general formula (3) and α-diketone B are stirred while being heated in an appropriate solvent (e.g., chloroform), so that the quinoxaline derivative represented by the general formula (1) can be obtained. Note that if α-diketone A and α-diketone B are the same compound, one step reaction is enough for synthesis, not two-step reaction as shown in the synthesis scheme (a).

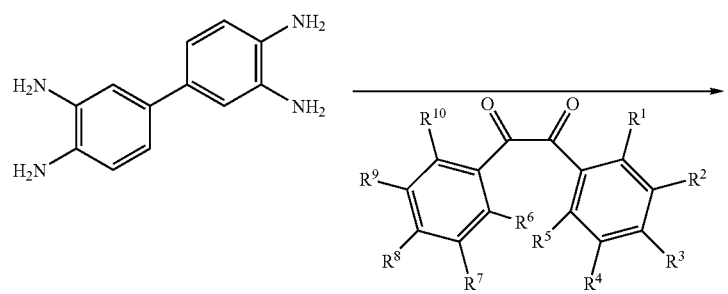

-continued

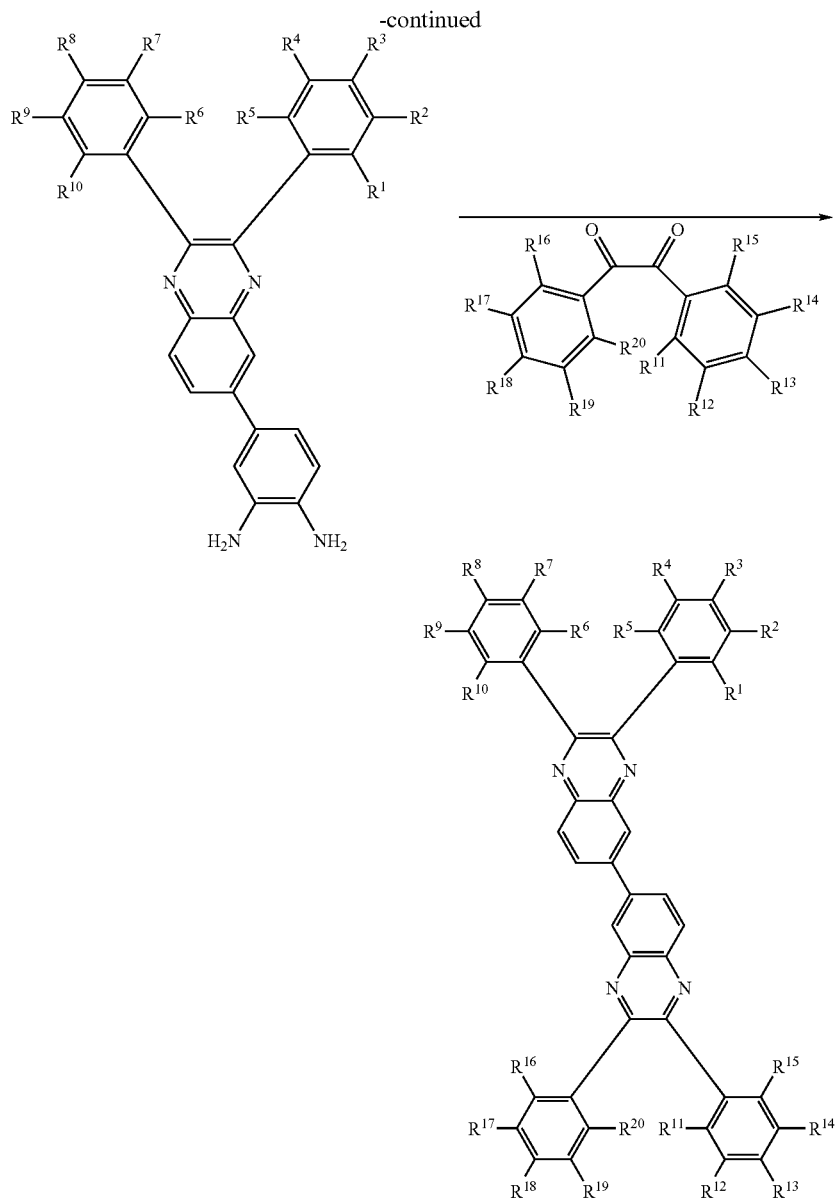

Note that at least one of $R^1$ to $R^{20}$ is any of a fluoro group, a cyano group, a trifluoromethyl group, a nitro group, an acyl group and an acyloxy group, and the others are hydrogen.

Embodiment Mode 3

This embodiment mode will describe a light-emitting element in which a plurality of light-emitting units in accordance with the present invention are stacked (hereinafter referred to as a stack element) with reference to FIG. 5. The light-emitting element is a stacked-type light-emitting element which has a plurality of light-emitting units between a first electrode and a second electrode. A structure similar to that of the EL layer 203 shown in Embodiment Mode 1 can be used for each light-emitting unit. In other words, the light-emitting element described in each of Embodiment Modes 1 and 2 is a light-emitting element having a single light-emitting unit. However, in this embodiment mode, a light-emitting element having a plurality of light-emitting units will be described.

Figure 5:
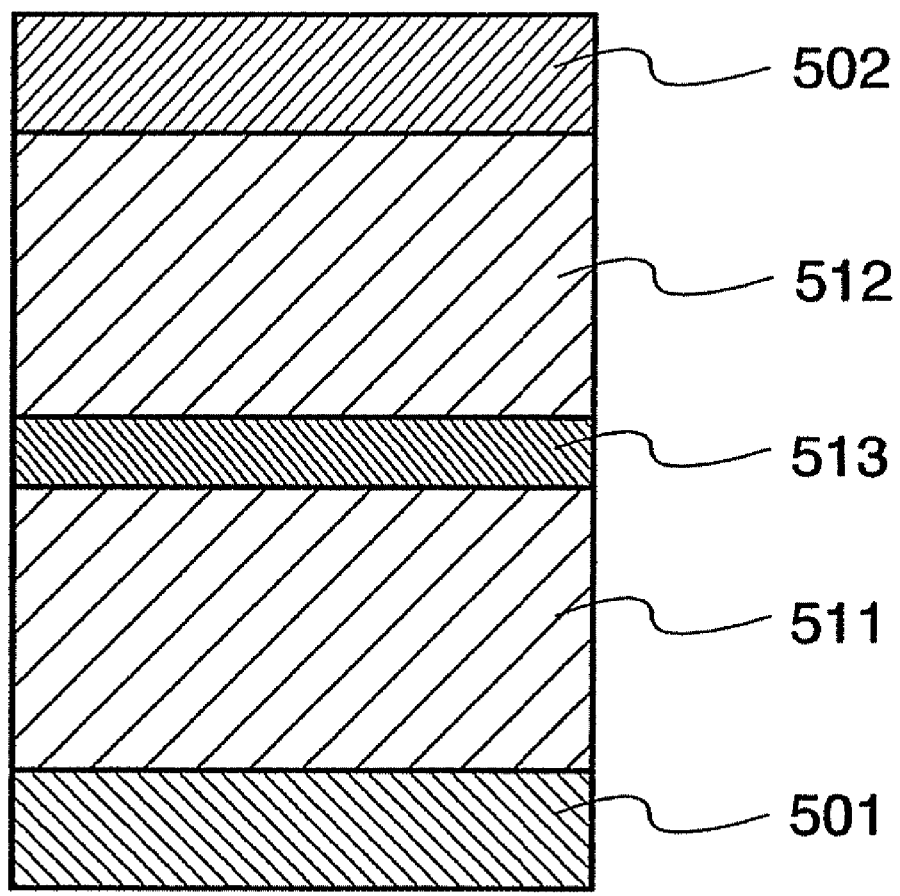
FIG. 5 shows a light-emitting element according to an aspect of the present invention.

In FIG. 5, a first light-emitting unit 511 and a second light-emitting unit 512 are stacked between a first electrode 501 and a second electrode 502. A charge generation layer 513 is provided between the first light-emitting unit 511 and the second light-emitting unit 512. An electrode similar to that shown in Embodiment Mode 1 can be applied to the first electrode 501 and the second electrode 502. The first light-emitting unit 511 and the second light-emitting unit 512 may have either the same structure or different structures, and a structure similar to that shown in Embodiment Modes 1 can be applied.

The charge generation layer 513 contains a composite material of an organic compound and metal oxide. The composite material of an organic compound and metal oxide is described in Embodiment Mode 1, and includes an organic compound and metal oxide such as vanadium oxide, molybdenum oxide, or tungsten oxide. As the organic compound, a wide variety of compounds such as aromatic amine compounds, carbazole derivatives, aromatic hydrocarbons, and high molecular compounds (e.g., oligomer, dendrimer, or polymer) can be used. It is preferable to use an organic compound having a hole mobility of greater than or equal to $10^{-6}$ cm$^2$/Vs as the organic compound having a hole-transporting property. However, other substances than these substances may also be used as long as the hole-transporting properties thereof are higher than the electron-transporting properties thereof. The composite material of an organic compound and metal oxide is superior in carrier injection property and carrier transporting property, and therefore, low-voltage driving and low-current driving can be realized.

Note that the charge generation layer 513 may be formed by combining a composite material of an organic compound and metal oxide, with another material. For example, the charge generation layer 513 may be formed with a combination of a layer including the composite material of an organic compound and metal oxide, and a layer including one compound selected from electron donating substances and a compound having a high electron-transporting property. Further, the charge generation layer 513 may be formed with a combination of a layer including the composite material of an organic compound and metal oxide, with a transparent conductive film.

In any case, as the charge generation layer 513 sandwiched between the first light-emitting unit 511 and the second light-emitting unit 512, such a material that can inject electrons to one light-emitting unit and holes to the other light-emitting unit when a voltage is applied between the first electrode 501 and the second electrode 502, may be used. For example, in FIG. 5, when a voltage is applied so that a potential of the first electrode is higher than a potential of the second electrode, any structure may be used for the charge generation layer 513, as long as the charge generation layer 513 injects electrons and holes into the first light-emitting unit 511 and the second light-emitting unit 512, respectively.

Although this embodiment mode illustrates the light-emitting element having two light-emitting units, the present invention can be similarly applied to a light-emitting element in which three or more light-emitting units are stacked. By arranging a plurality of light-emitting units between a pair of electrodes in such a manner that the plurality of light-emitting units are partitioned with a charge generation layer, a light-emitting element having a long life and high luminance can be realized while maintaining a low current density. In addition, when the light-emitting element is applied to a lighting device, a voltage drop which would be caused by the resistance of an electrode material can be suppressed. Thus, uniform light emission over a large area is possible. In other words, a light-emitting device capable of low-voltage driving and low-power consumption can be realized.

When the light-emitting units are formed to have different emission colors from each other, light emission of a desired color can be obtained from the whole light-emitting element. For example, in the light-emitting element having two light-emitting units, when the emission color of the first light-emitting unit and the emission color of the second light-emitting unit are complementary colors, a light-emitting element which emits white light as a whole can be obtained. Note that "complementary colors" refer to colors which can produce an achromatic color when mixed. That is, when light emitted from substances which emit light of complementary colors are mixed, white emission can be obtained. The same can be applied to a light-emitting element which has three light-emitting units. For example, white emission can be obtained from the whole light-emitting element when the emission color of the first light-emitting unit is red, the emission color of the second light-emitting unit is green, and the emission color of the third light-emitting unit is blue.

Note that this embodiment mode can be combined with any of the other embodiment modes as appropriate.

Embodiment Mode 4

This embodiment mode will describe a light-emitting device having the light-emitting element of the present invention.

In this embodiment mode, a light-emitting device having a pixel portion which includes the light-emitting element of the present invention will be described with reference to FIGS. 6A and 6B. FIG. 6A is a top view of a light-emitting device, and FIG. 6B is a cross-sectional view taken along lines A-A' and B-B' of FIG. 6A. Reference numerals 601, 602, and 603 denote a driver circuit portion (a source driver circuit), a pixel portion, and a driver circuit portion (a gate driver circuit), respectively, which are indicated by dotted lines. In addition, reference numerals 604 and 605 denote a sealing substrate and a sealing material, respectively, and a portion surrounded by the sealing material 605 corresponds to a space 607.

A lead wiring 608 is a wiring for transmitting signals to the source driver circuit 601 and the gate driver circuit 603, and this wiring 608 receives video signals, clock signals, start signals, reset signals, or the like from an FPC (Flexible Printed Circuit) 609 that is an external input terminal. Although only the FPC is shown here, the FPC may be provided with a printed wiring board (PWB). The light-emitting device in this specification includes not only a light-emitting device itself but also a light-emitting device with an FPC or a PWB attached thereto.

Next, a cross-sectional structure will be described with reference to FIG. 6B. The driver circuit portion and the pixel portion are formed over a substrate 610. Here, the source driver circuit 601, which is the driver circuit portion, and one pixel in the pixel portion 602 are shown.

A CMOS circuit, which is a combination of an n-channel TFT 623 and a p-channel TFT 624, is formed for the source driver circuit 601. The driver circuit may be formed using various types of circuits, such as CMOS circuits, PMOS circuits, or NMOS circuits. Although a driver-integration type device, in which a driver circuit is formed over the same substrate as the pixel portion, is shown in this embodiment mode, a driver circuit is not necessarily formed over the same substrate as the pixel portion and can be formed outside the substrate.

The pixel portion 602 has a plurality of pixels, each of which includes a switching TFT 611, a current-controlling TFT 612, and a first electrode 613, which is electrically connected to a drain of the current-controlling TFT 612. Note that an insulator 614 is formed so as to cover an end portion of the first electrode 613. Here, a positive photosensitive acrylic resin film is used for the insulator 614.

The insulator 614 is formed so as to have a curved surface having curvature at an upper end portion or a lower end portion thereof in order to obtain favorable coverage. For example, in the case of using a positive photosensitive acrylic resin as a material for the insulator 614, the insulator 614 is preferably formed so as to have a curved surface with a curvature radius (0.2 to 3 μm) only at the upper end portion thereof. Either a negative photoresist which becomes insoluble in an etchant by light irradiation or a positive photoresist which becomes soluble in an etchant by light irradiation can be used for the insulator 614.

An EL layer 616 and a second electrode 617 are formed over the first electrode 613, so that a light-emitting element

618 of the present invention is formed. Specifically, as the light-emitting element 618, the light-emitting element shown in Embodiment Mode 1 or Embodiment Mode 3 may be used.

A wide variety types of materials, such as metals, alloys, electrically conductive compounds, or mixture of them can be used for a material for forming the first electrode 613. When the first electrode 613 is used as an anode, it is particularly preferable to select a material with a high work function (a work function of 4.0 eV or higher) among such metals, alloys, electrically conductive compounds, and mixture of them. For example, the first electrode 613 can be formed by using a single-layer film such as a film made of indium tin oxide including silicon, a film made of indium zinc oxide, a titanium nitride film, a chromium film, a tungsten film, a Zn film, or a Pt film; a stacked layer of a titanium nitride film and a film including aluminum as its main component; a three-layer structure of a titanium nitride film, a film including aluminum as its main component, and a titanium nitride film; or the like. When the first electrode 613 has a stacked structure, the electrode 613 has low resistance enough to serve as a wiring, giving a good ohmic contact. Further, the first electrode 613 can function as an anode.

In addition, the EL layer 616 is formed by various methods such as a vapor-deposition method using an evaporation mask, an inkjet method, and a spin coating method. The EL layer 616 includes the first layer and the second layer (light-emitting layer) shown in Embodiment Mode 1. As other materials for forming the EL layer 616, low molecular compounds or high molecular compounds (including oligomer and dendrimer) may also be used. In addition, not only organic compounds, but also inorganic compounds can be used for the material for forming the EL layer.

As a material for forming the second electrode 617, a wide variety of materials, such as metals, alloys, electrically conductive compounds, or mixture of them can be used. When the second electrode 617 is used as a cathode, it is particularly preferable to select a material with a low work function (a work function of 3.8 eV or lower) among such metals, alloys, electrically conductive compounds, and mixture of them. For example, elements belonging to Group 1 or 2 of the periodic table, i.e., alkali metals such a lithium (Li) and cesium (Cs) and alkaline earth metals such as magnesium (Mg), calcium (Ca), and strontium (Sr); alloys of them (e.g., MgAg and AlLi); and the like can be used. In the case where light generated in the EL layer 616 is transmitted through the second electrode 617, the second electrode 617 may also be formed using a stacked layer of a thin metal film having a small thickness and a transparent conductive film (e.g., indium tin oxide (ITO), indium tin oxide including silicon or silicon oxide, indium zinc oxide (IZO), or indium oxide including tungsten oxide and zinc oxide (IWZO)).

The sealing substrate 604 is attached to the element substrate 610 with the sealing material 605, and thereby the light-emitting element 618 is provided in the space 607 surrounded by the element substrate 610, the sealing substrate 604, and the sealing material 605. Note that the space 607 is filled with a filler, and the space 607 may be filled with an inert gas (e.g., nitrogen or argon) or the sealing material 605.

Note that an epoxy resin is preferably used for the sealing material 605. Such a material preferably allows as little moisture and oxygen as possible to penetrate. As a material for forming the sealing substrate 604, a glass substrate or a quartz substrate can be used as well as a plastic substrate made of FRP (Fiberglass-Reinforced Plastics), PVF (polyvinyl fluoride), polyester, acrylic, or the like.

By the above-described process, a light-emitting device having the light-emitting element of the present invention can be obtained. The thus obtained light-emitting device of the present invention has a long-lifetime light-emitting element; therefore, the device itself also has a long lifetime.

Figure 7A:
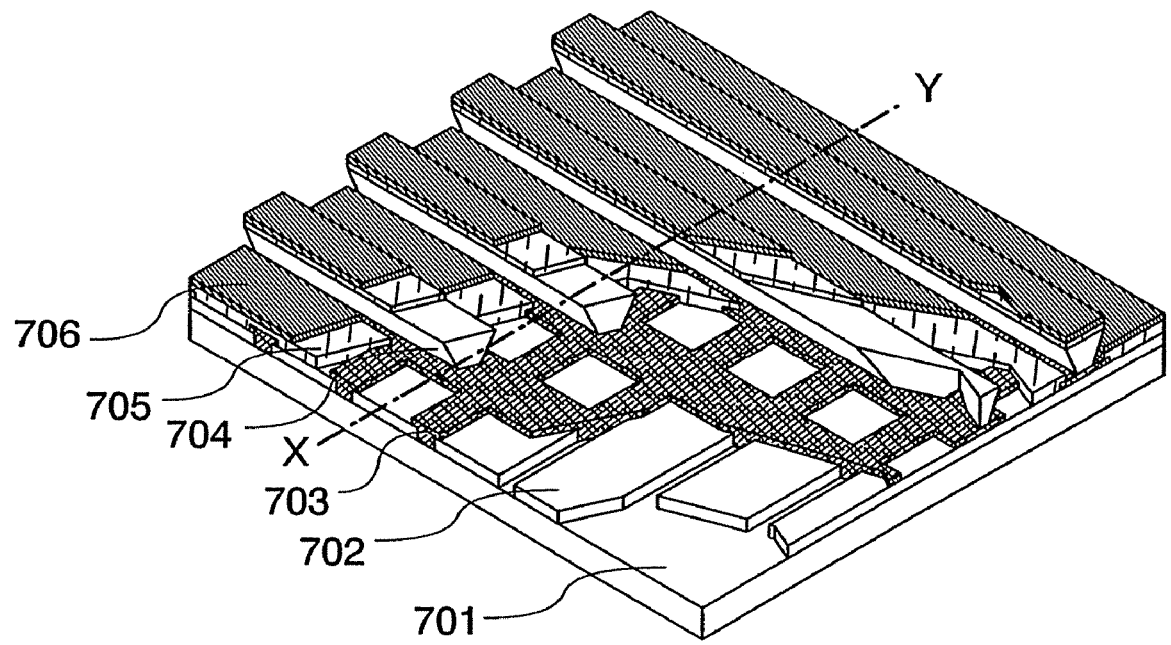
FIGS. 7A and 7B show a light-emitting device according to an aspect of the present invention.
Figure 7B:
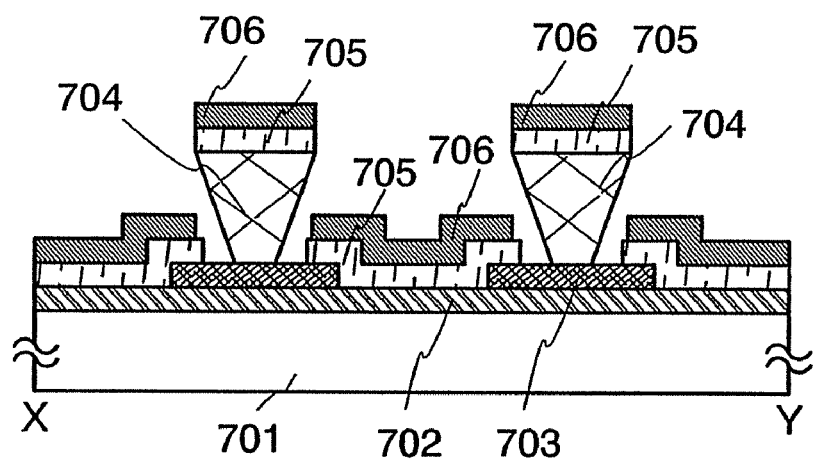

Although this embodiment mode illustrates an active matrix light-emitting device in which drive of a light-emitting element is controlled by a transistor, it is also possible to use a passive matrix light-emitting device in which a light-emitting element is driven without an element for driving the light-emitting element such as a transistor. FIGS. 7A and 7B show a perspective view and a cross-sectional view, respectively, of a passive matrix light-emitting device which is formed by applying the present invention. FIG. 7A is a cross-sectional view of the light-emitting device, and FIG. 7B is a cross-sectional view taken along a line X-Y of FIG. 7A. In FIGS. 7A and 7B, an EL layer 705 is provided between an electrode 702 and an electrode 706 over a substrate 701. An end portion of the electrode 702 is covered with an insulating layer 703. A partition layer 704 is provided over the insulating layer 703. A side wall of the partition layer 704 slopes so that a distance between one side wall and the other side wall becomes narrow toward a substrate surface. In other words, a cross section of the partition layer 704 in the direction of a short side is trapezoidal, and a bottom base (a side in the same direction as a plane direction of the insulating layer 703 and in contact with the insulating layer 703) is shorter than a top base (a side in the same direction as the plane direction of the insulating layer 703 and not in contact with the insulating layer 703). The partition layer 704 provided in this manner can prevent the light-emitting element from being defective due to static electricity or the like. In addition, a passive matrix light-emitting device can also be formed as a long-lifetime light-emitting device by applying the long-lifetime light-emitting element of the present invention.

Embodiment Mode 5

Embodiment Mode 5 will describe electronic devices of the present invention which includes the light-emitting device described in Embodiment Mode 4 as a component part. The electronic devices of the present invention include the light-emitting element described in any of Embodiment Modes 1 or 3, and thus has a display portion with a long lifetime. In addition, since the light-emitting element with high luminous efficiency are used, a display portion with reduced power consumption can be obtained.

Typical examples of electronic devices which are formed using the light-emitting device of the present invention include cameras such as video cameras and digital cameras, goggle displays, navigation systems, audio reproducing devices (e.g., car audio component stereos and audio component stereos), computers, game machines, portable information terminals (e.g., mobile computers, mobile phones, portable game machines, and electronic books), and image reproducing devices provided with a recording medium (specifically, a device capable of reproducing the content of a recording medium such as a digital versatile disc (DVD) and provided with a display device that can display the reproduced image), and the like. Specific examples of these electronic devices are shown in FIGS. 8A to 8D.

Figure 8A:
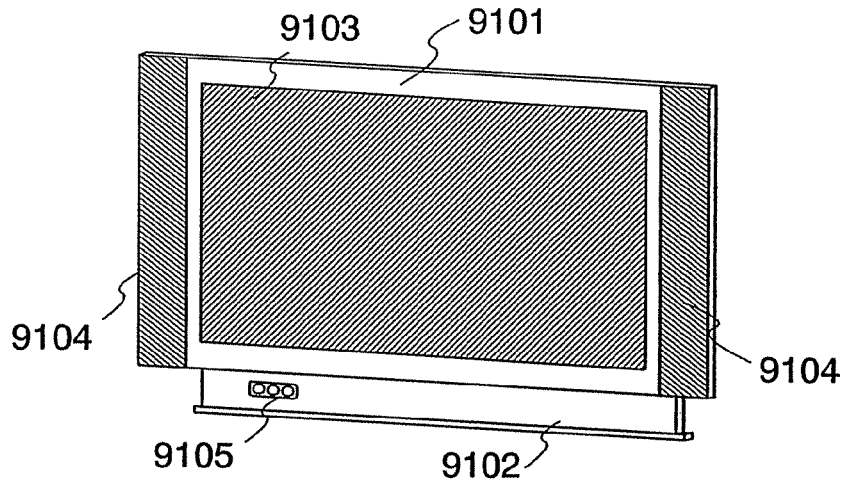
FIGS. 8A to 8D show electronic devices according to an aspect of the present invention.

FIG. 8A shows a television set in accordance with the present invention, which includes a housing 9101, a supporting base 9102, a display portion 9103, speaker portions 9104, video input terminals 9105, and the like. In the television set, the display portion 9103 has a matrix arrangement of light-emitting elements similar to the light-emitting element shown in Embodiment Modes 1 or 3. The light-emitting elements has a feature of having long lifetime. The display portion 9103 which includes the light-emitting element has the same feature. Therefore, this television set also has the feature of having long lifetime. In other words, a television set which is durable for use over a long period of time can be provided.

Figure 8B:
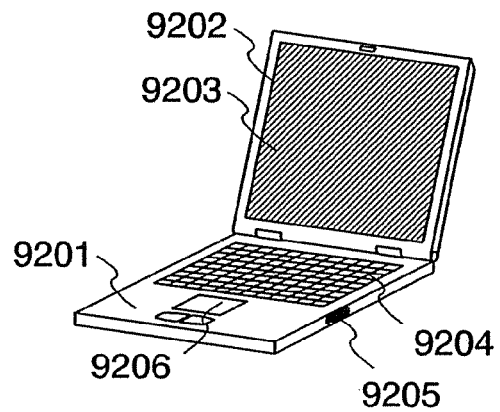

FIG. 8B shows a computer in accordance with the present invention, which includes a main body 9201, a housing 9202, a display portion 9203, a keyboard 9204, an external connection port 9205, a pointing device 9206, and the like. In the computer, the display portion 9203 has a matrix arrangement of light-emitting elements similar to the light-emitting element shown in Embodiment Modes 1 or 3. The light-emitting element has a feature of having long lifetime. The display portion 9203 which includes the light-emitting elements has the same feature. Therefore, this computer also has the feature of having long lifetime. In other words, a computer which is durable for use over a long period of time can be provided.

Figure 8C:
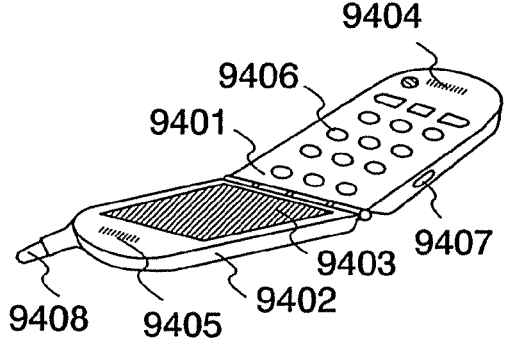

FIG. 8C shows a mobile phone in accordance with the present invention, which includes a main body 9401, a housing 9402, a display portion 9403, an audio input portion 9404, an audio output portion 9405, operation keys 9406, an external connection port 9407, an antenna 9408, and the like. In the mobile phone, the display portion 9403 has a matrix arrangement of light-emitting elements similar to the light-emitting element shown in Embodiment Modes 1 or 3. The light-emitting element has a feature of having long lifetime. The display portion 9403 which includes the light-emitting element has the same feature. Therefore, this mobile phone also has the feature of having long lifetime. In other words, a mobile phone which is durable for use over a long period of time can be provided.

Figure 8D:
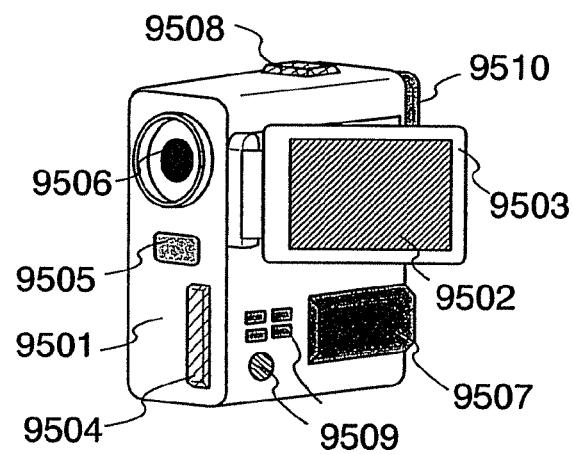

FIG. 8D shows a camera in accordance with the present invention, which includes a main body 9501, a display portion 9502, a housing 9503, an external connection port 9504, a remote control receiving portion 9505, an image receiving portion 9506, a battery 9507, an audio input portion 9508, operation keys 9509, an eye piece portion 9510, and the like. In the camera, the display portion 9502 has a matrix arrangement of light-emitting elements similar to the light-emitting element shown in Embodiment Modes 1 or 3. The light-emitting element has a feature of having long lifetime. The display portion 9502 which includes the light-emitting element has the same feature. Therefore, this camera also has the feature of having long lifetime. In other words, a camera which is durable for use over a long period of time can be provided.

As described above, the applicable range of the light-emitting device of the present invention is so wide that the light-emitting device can be applied to electronic devices in a wide variety of fields. By using the light-emitting device of the present invention, an electronic device having a long-lifetime display portion which is durable for use over a long period of time can be provided.

The light-emitting device of the present invention can also be used as a lighting device. An example of using the light-emitting element of the present invention for a lighting device will be described with reference to FIG. 9.

Figure 9:
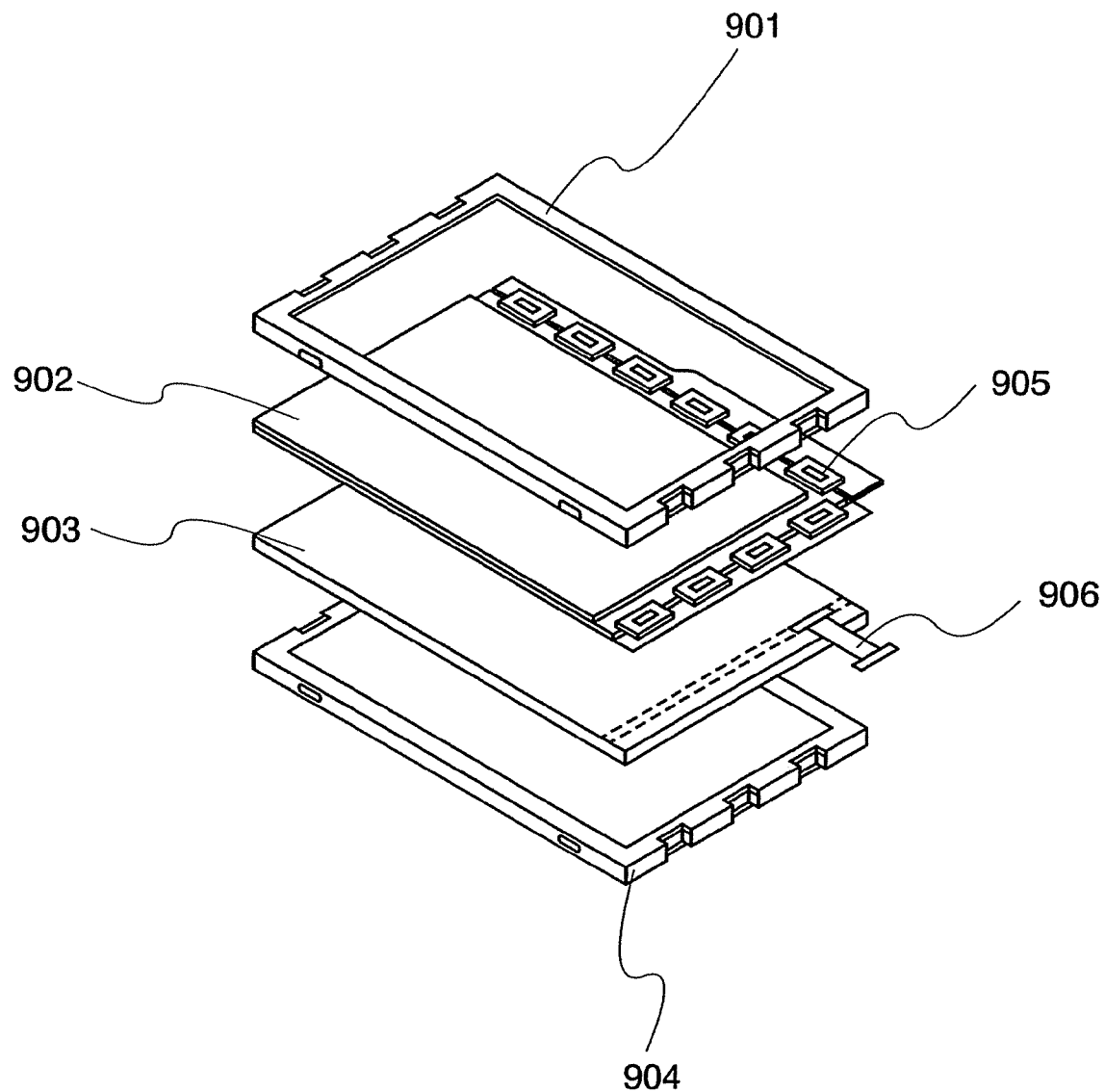
FIG. 9 shows an application example of a light-emitting device according to an aspect of the present invention.

FIG. 9 shows an example of a liquid crystal display device which uses the light-emitting device of the present invention as a backlight. The liquid crystal display device shown in FIG. 9 includes a housing 901, a liquid crystal layer 902, a backlight 903, and a housing 904, and the liquid crystal layer 902 is connected to a driver IC 905. The light-emitting device of the present invention is used for the backlight 903, and current is supplied through a terminal 906.

By using the light-emitting device of the present invention as the backlight of the liquid crystal display device, a backlight with long lifetime can be obtained. The light-emitting device of the present invention is a lighting device with plane light emission, and can have a large area. Therefore, the backlight can have a large area, and a liquid crystal display device having a large area can be obtained. Furthermore, the light-emitting device of the present invention has a thin shape and has low power consumption; therefore, a thin shape and low power consumption of a display device can also be achieved. In addition, since the light-emitting device of the present invention has long lifetime, a liquid crystal display device with long lifetime can be provided by incorporating the light-emitting device of the present invention.

Figure 10:
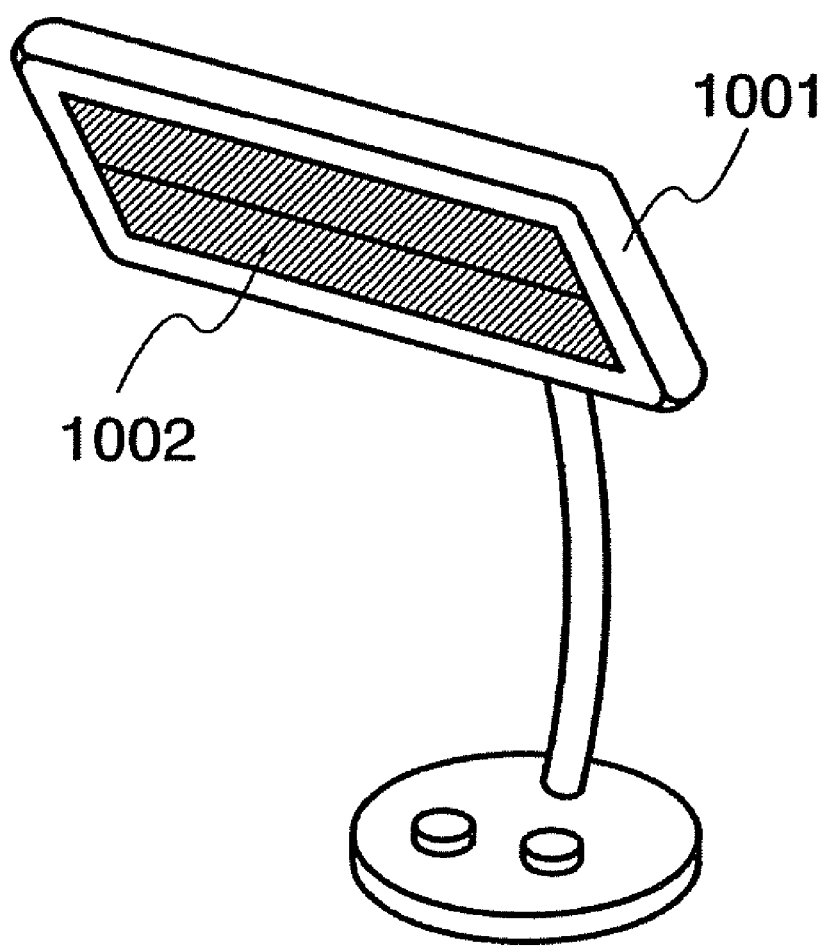
FIG. 10 shows an application example of a light-emitting device according to an aspect of the present invention.

FIG. 10 shows an example of using a light-emitting device of the present invention for a table lamp as a lighting device. The table lamp shown in FIG. 10 has a housing 1001 and a light source 1002, and the light-emitting device of the present invention is used as the light source 1002. The light-emitting device of the present invention has a long lifetime; therefore, the table lamp also has a long lifetime.

Figure 11:
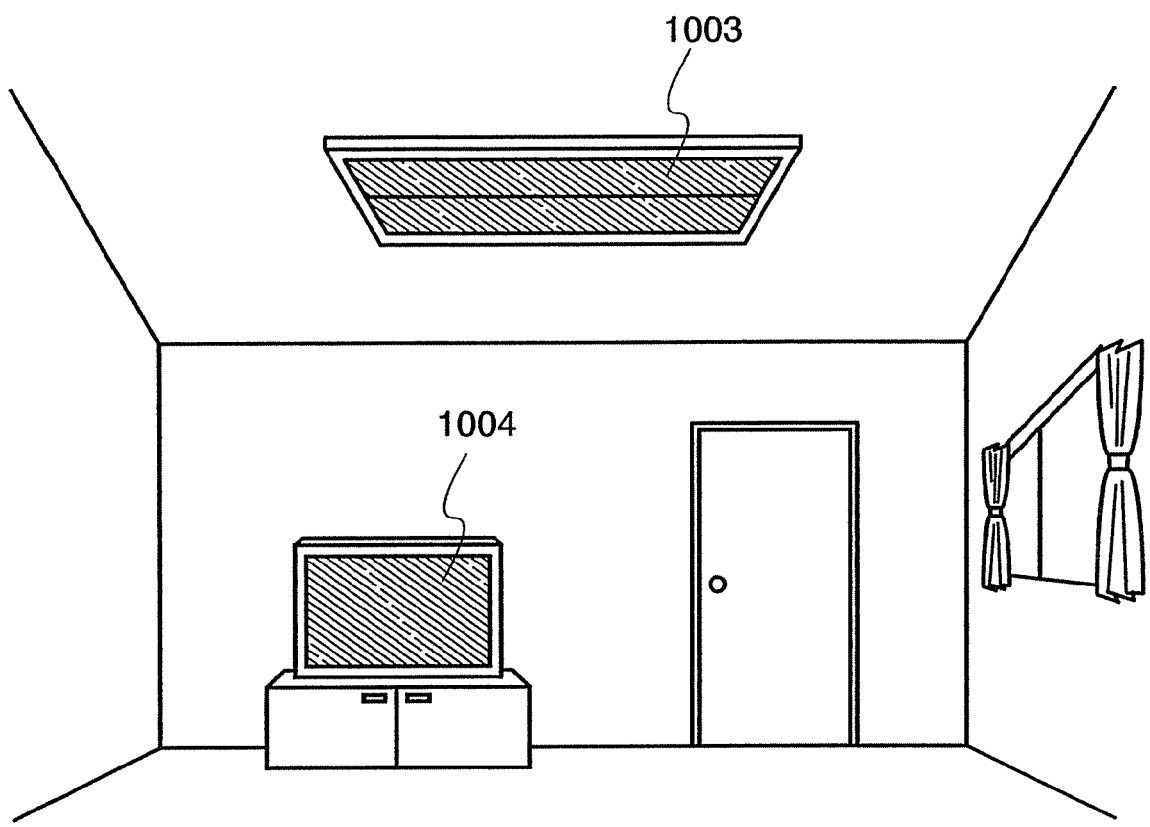
FIG. 11 shows an application example of a light-emitting device according to an aspect of the present invention.

FIG. 11 shows an example of using the light-emitting device of the present invention for an indoor lighting device 1003. Since the light-emitting device of the present invention can have a large area, the light-emitting device of the present invention can be used as a lighting device having a large emission area. Furthermore, since the light-emitting device of the present invention has long lifetime, a lighting device having a long lifetime can be obtained. When a television set 1004 in accordance with the present invention like the one illustrated in FIG. 8A is placed in a room in which the light-emitting device of the present invention is used as the indoor lighting device 1003, public broadcasting and movies can be watched. In such a case, since both of the devices have long lifetimes, frequency of replacement of the lighting device and the television set can be reduced, and damage on the environment can be reduced.

Example 1

Figure 12:
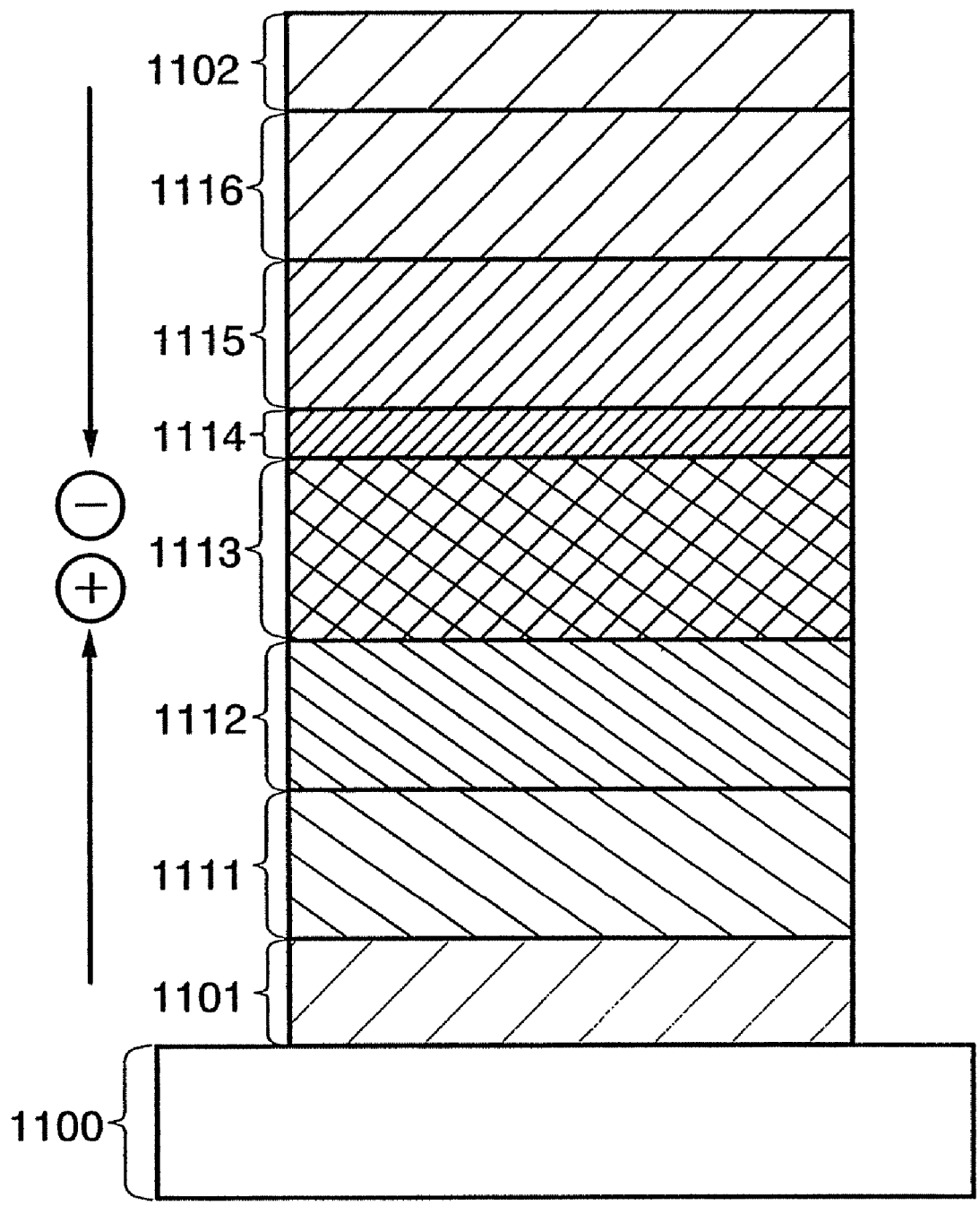
FIG. 12 shows a structure of a light-emitting element according to an aspect of the present invention.

Example 1 will describe a light-emitting element of the present invention with reference to FIG. 12. Structural formulae of materials used in this example are shown below.

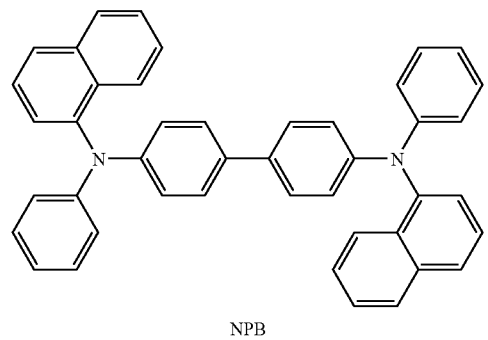

NPB

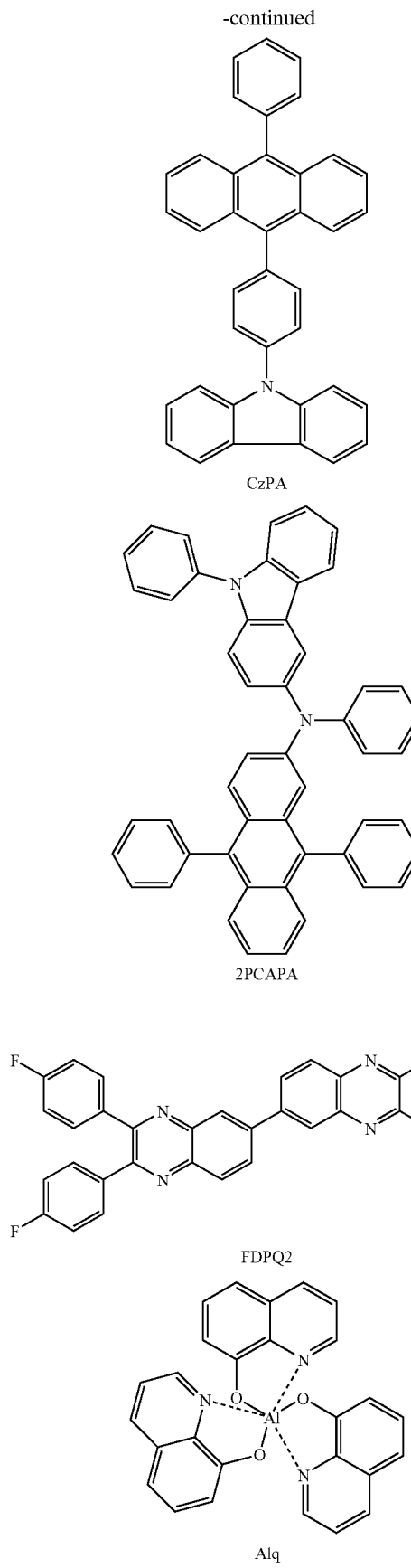

BPhen (Light-Emitting Element 1)

First, indium tin oxide including silicon oxide was deposited over a glass substrate 1100 by a sputtering method to form a first electrode 1101. Note that the thickness of the first electrode 1101 was 110 nm and the electrode area was 2 mm×2 mm.

Next, the substrate having the first electrode 1101 was fixed to a substrate holder provided in a vacuum evaporation apparatus in such a way that the surface of the first electrode faced downward, and then the pressure was reduced to about $10^{-4}$ Pa. Next, 4,4'-bis[N-(1-naphthyl)-N-phenylamino]biphenyl (abbreviation: NPB) and molybdenum(VI) oxide were co-deposited over the first electrode 1101, whereby a layer 1111 including a composite material of an organic compound and an inorganic compound was formed. The thickness of the layer 1111 was set to be 50 nm and the weight ratio of NPB to molybdenum(VI) oxide was set to be 4:1 (=NPB:molybdenum oxide). Note that the co-deposition method is an evaporation method in which evaporation is performed using a plurality of evaporation sources at the same time in one treatment chamber.

Next, a hole-transporting layer 1112 was formed by depositing NPB to a thickness of 10 nm by an evaporation method using resistance heating.

After that, a light-emitting layer 1113 was formed over the hole-transporting layer 1112. The light-emitting layer 1113 was formed by co-depositing 9-[4-(10-phenyl-9-anthryl)phenyl]-9H-carbazole (abbreviation: CzPA) and N-(9,10-diphenyl-2-anthryl)-N,9-diphenyl-9H-carbazol-3-amine (abbreviation: 2PCAPA) to a thickness of 30 nm, over the hole-transporting layer 1112. Here, the deposition rate was controlled so that the weight ratio of CzPA to 2PCAPA could be 1:0.05 (=CzPA:2PCAPA).

Further, a layer 1114 for controlling electron transfer was formed by co-depositing tris(8-quinolinolato)aluminum(III) (abbreviation: Alq) and 2,3,2',3'-tetrakis(4-fluorophenyl)-6,6'-biquinoxaline (abbreviation: FDPQ2) which is a second organic compound having an electron-trapping property, to a thickness of 10 nm over the light-emitting layer 1113. Here, the deposition rate was controlled so that the weight ratio of Alq to FDPQ2 could be 1:0.005 (=Alq:FDPQ2).

Next, an electron-transporting layer 1115 was formed by depositing bathophenanthroline (abbreviation: BPhen) to a thickness of 30 nm over the layer 1114 for controlling electron transfer by an evaporation method using resistance heating.

Then, an electron-injecting layer 1116 was formed by depositing lithium fluoride (LiF) to a thickness of 1 nm over the electron-transporting layer 1115.

Finally, a second electrode 1102 was formed by depositing aluminum to a thickness of 200 nm by an evaporation method using resistance heating. Thus, a light-emitting element 1 of the present invention was formed.

The thus obtained light-emitting element 1 of the present invention was put into a glove box under a nitrogen atmosphere so that the light-emitting element was sealed from atmospheric air. Then, the operating characteristics of the light-emitting element 1 were measured. Note that the measurement was conducted at room temperature (atmosphere kept at 25° C.).

Figure 13:
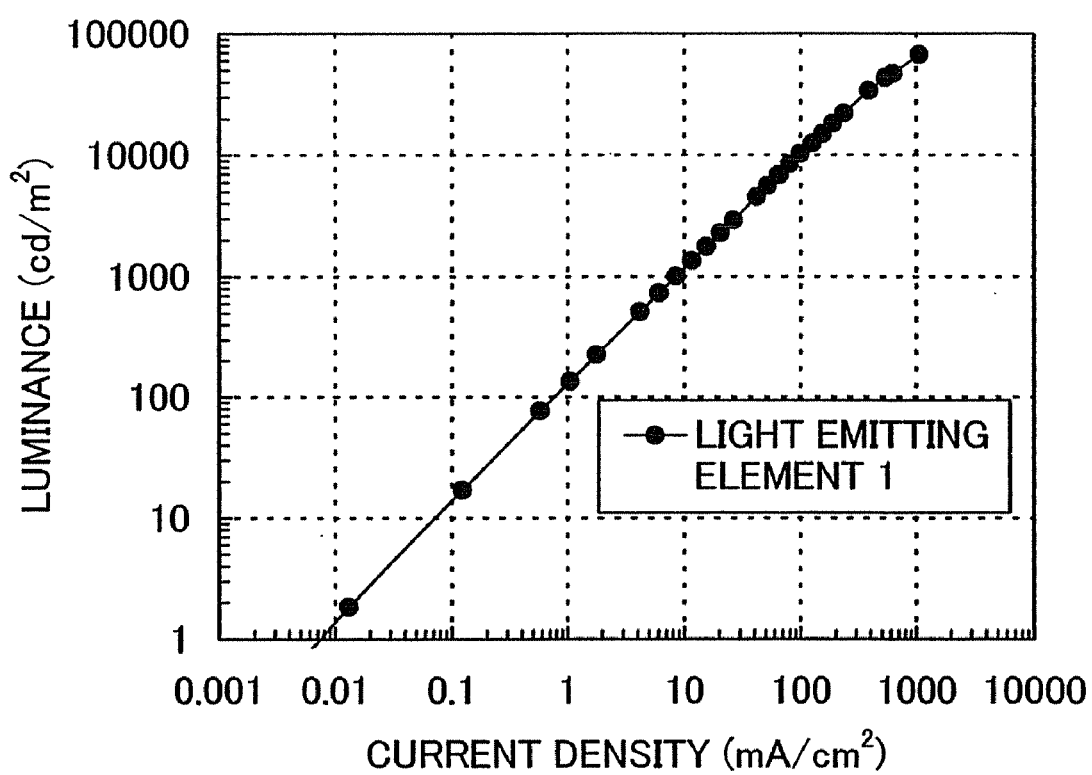
FIG. 13 is a graph showing current density vs. luminance characteristics of a light-emitting element 1 according to an aspect of the present invention.
Figure 14:
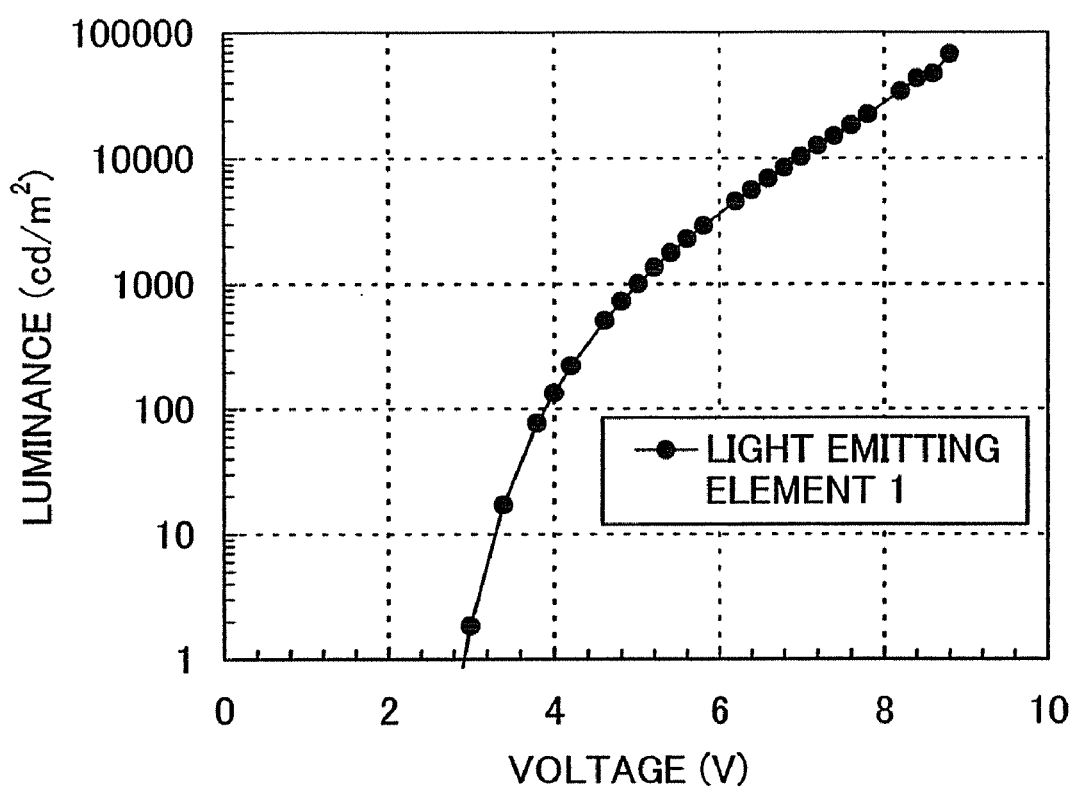
FIG. 14 is a graph showing voltage vs. luminance characteristics of the light-emitting element 1 according to an aspect of the present invention.
Figure 15:
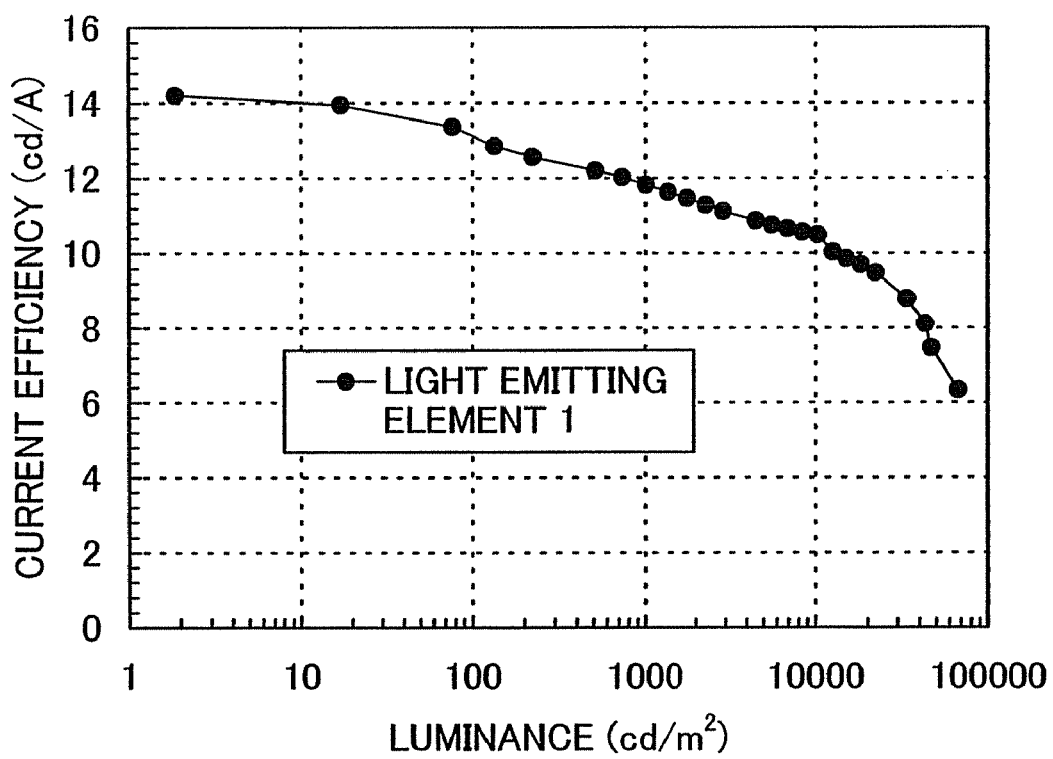
FIG. 15 is a graph showing luminance vs. current efficiency characteristics of the light-emitting element 1 according to an aspect of the present invention.
Figure 16:
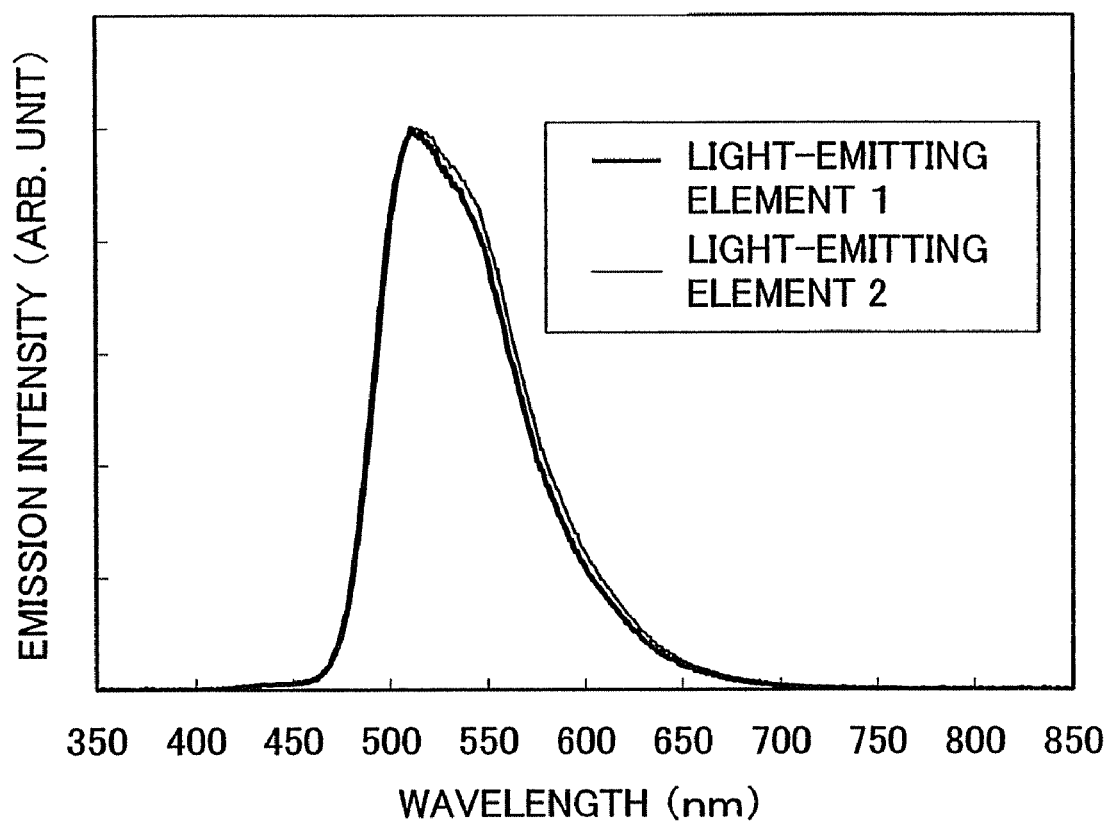
FIG. 16 shows emission spectra of the light-emitting element 1 of the present invention and a reference light-emitting element 2.

FIG. 13 shows the current density vs. luminance characteristics of the light-emitting element 1. FIG. 14 shows the voltage vs. luminance characteristics of the light-emitting element 1. FIG. 15 shows the luminance vs. current efficiency characteristics of the light-emitting element 1. FIG. 16 shows the emission spectrum of the light-emitting element 1 at a current supply of 1 mA. The emission color of the light-emitting element 1 was located at the CIE chromaticity coordinates of (x=0.29, y=0.60) at the luminance of 2910 cd/m$^2$, and green emission which derived from 2PCAPA was obtained. In addition, the current efficiency and driving voltage of the light-emitting element 1 at the luminance of 2910 cd/m$^2$ were 11.1 cd/A and 5.8 V, respectively.

Figure 17:
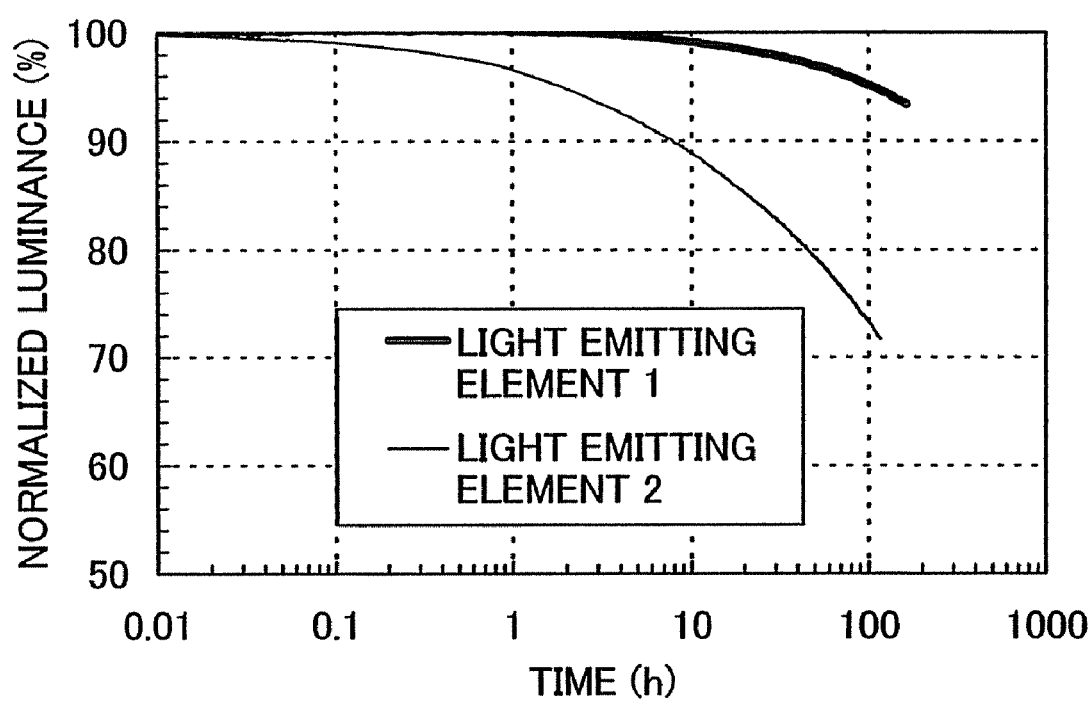
FIG. 17 shows a result of a continuous lighting test in which the light-emitting element 1 of the present invention and the reference light-emitting element 2 were continuously lit by constant current driving.

FIG. 17 shows the result of a continuous lighting test in which the light-emitting element 1 was continuously lit by constant current driving with the initial luminance set at 5000 cd/m$^2$ (the vertical axis indicates the relative luminance on the assumption that 5000 cd/m$^2$ is 100%). From the result shown in FIG. 17, the light-emitting element 1 exhibits 93% of the initial luminance even after 160 hours, and was proved to have long lifetime.

Comparative Example 1

Figure 18:
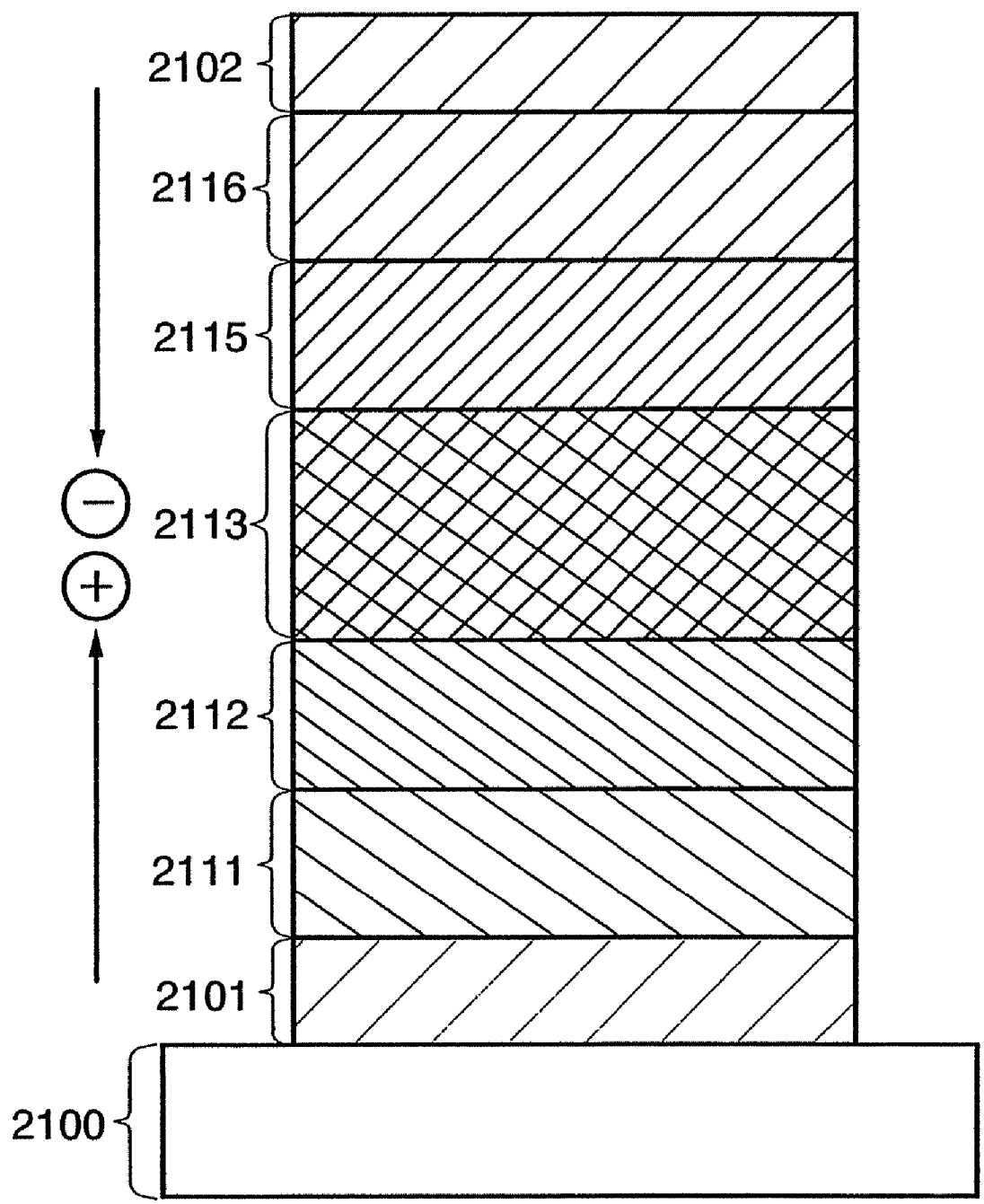
FIG. 18 shows a structure of the reference light-emitting element 2.

Next, for the sake of comparison, a reference light-emitting element 2 was formed, which was not provided with the layer 1114 for controlling electron transfer that was formed in the above-described light-emitting element 1. The reference light-emitting element 2 will now described with reference to FIG. 18.

First, indium tin oxide including silicon oxide was deposited over a glass substrate 2100 by a sputtering method to form a first electrode 2101. Note that the thickness of the first electrode 2101 was 110 nm and the electrode area was 2 mm×2 mm.

Next, the substrate having the first electrode was fixed to a substrate holder provided in a vacuum evaporation apparatus in such a way that the surface of the first electrode faced downward, and then the pressure was reduced to about 10$^{-4}$ Pa. Then, NPB and molybdenum(VI) oxide were co-deposited over the first electrode, whereby a layer 2111 including a composite material of an organic compound and an inorganic compound was formed. The thickness of the layer including a composite material was set to be 50 nm and the weight ratio of NPB to molybdenum(VI) oxide was set to be 4:1 (=NPB: molybdenum oxide). Note that the co-deposition method is an evaporation method in which evaporation is performed using a plurality of evaporation sources at the same time in one treatment chamber.

Next, a hole-transporting layer 2112 was formed by depositing NPB to a thickness of 10 nm by an evaporation method using resistance heating.

After that, a light-emitting layer 2113 was formed over the hole-transporting layer 2112. The light-emitting layer 2113 was formed by co-depositing 9-[4-(10-phenyl-9-anthryl)phenyl]-9H-carbazole (abbreviation: CzPA) and N-(9,10-diphenyl-2-anthryl)-N,9-diphenyl-9H-carbazol-3-amine (abbreviation: 2PCAPA) to a thickness of 40 nm, over the hole-transporting layer 2112. Here, the deposition rate was controlled so that the weight ratio of CzPA to 2PCAPA could be 1:0.05 (=CzPA:2PCAPA).

Next, an electron-transporting layer 2115 was formed by depositing bathophenanthroline (abbreviation: BPhen) to a thickness of 30 nm over the light-emitting layer 2113 by an evaporation method using resistance heating.

Then, an electron-injecting layer 2116 was formed by depositing lithium fluoride (LiF) to a thickness of 1 nm over the electron-transporting layer 2115.

Finally, a second electrode 2102 was formed by depositing aluminum to a thickness of 200 nm by an evaporation method using resistance heating. Thus, the reference light-emitting element 2 was formed.

The thus obtained reference light-emitting element 2 was put into a glove box under a nitrogen atmosphere so that the light-emitting element was sealed from atmospheric air. Then, the operating characteristics of the reference light-emitting element 2 were measured. Note that the measurement was conducted at room temperature (atmosphere kept at 25° C.).

The emission color of the reference light-emitting element 2 was located at the CIE chromaticity coordinates of (x=0.29, y=0.62) at the luminance of 3440 cd/m$^2$; and it exhibited green emission which derived from 2PCAPA similarly to the light-emitting element 1. FIG. 16 shows the emission spectrum of the reference light-emitting element 2 at a current supply of 1 mA, in addition the result of the light-emitting element 1 of the present invention. From the chromaticity coordinates and the emission spectra in FIG. 16, it was proved that the light-emitting element 1 of the present invention exhibited almost the same color as the reference light-emitting element 2, and mixed color due to FDPQ2 was not caused. Therefore, by applying the present invention, a light-emitting element having excellent color purity can be obtained.

Further, a continuous lighting test was conducted in which the reference light-emitting element 2 was continuously lit by constant current driving with the initial luminance set at 5000 cd/m$^2$. The result was shown in FIG. 17, together with the result of the light-emitting element 1 of the present invention (the vertical axis indicates the relative luminance on the assumption that 5000 cd/m$^2$ is 100%). From the results in FIG. 17, luminance of the reference light-emitting element 2 decreased to 72% of the initial luminance after 120 hours, and thus the lifetime of the reference light-emitting element 2 was proved to be shorter than that of the light-emitting element 1. Therefore, a long-lifetime light-emitting element can be obtained by applying the present invention.

Example 2

Example 2 will specifically describe a light-emitting element of the present invention with reference to FIG. 12. A structural formula of a material used in this example is shown below. Note that the organic compounds described in Example 1 are omitted here.

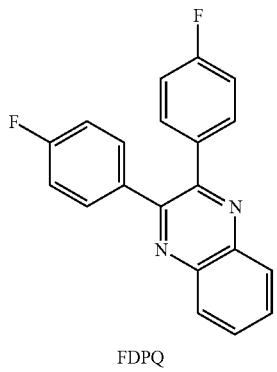

FDPQ (Light-Emitting Element 3)

First, indium tin oxide including silicon oxide was deposited over a glass substrate 1100 by a sputtering method to form a first electrode. Note that the thickness of the first electrode 1101 was 110 nm and the electrode area was 2 mm×2 mm.

Next, the substrate having the first electrode was fixed to a substrate holder provided in a vacuum evaporation apparatus in such a way that the surface of the first electrode faced downward, and then the pressure was reduced to about $10^{-4}$ Pa. Then, NPB and molybdenum(VI) oxide were co-deposited over the first electrode 1101, whereby a layer 1111 including a composite material of an organic compound and an inorganic compound was formed. The thickness of the layer including a composite material was set to be 50 nm and the weight ratio of NPB to molybdenum(VI) oxide was set to be 4:1 (=NPB:molybdenum oxide). Note that the co-deposition method is an evaporation method in which evaporation is performed using a plurality of evaporation sources at the same time in one treatment chamber.

Next, a hole-transporting layer 1112 was formed by depositing NPB to a thickness of 10 nm by an evaporation method using resistance heating.

Next, a light-emitting layer 1113 was formed over the hole-transporting layer 1112. The light-emitting layer 1113 was formed by co-depositing CzPA and 2PCAPA to a thickness of 30 nm over the hole-transporting layer 1112. Here, the deposition rate was controlled so that the weight ratio of CzPA to 2PCAPA could be 1:0.05 (=CzPA:2PCAPA).

Further, a layer 1114 for controlling electron transfer was formed by co-depositing Alq and 2,3-bis(4-fluorophenyl)quinoxaline (abbreviation: FDPQ), which is a second organic compound having an electron-trapping property, to a thickness of 10 nm over the light-emitting layer 1113. Here, the deposition rate was controlled so that the weight ratio of Alq to FDPQ could be 1:0.05 (=Alq:FDPQ).

After that, an electron-transporting layer 1115 was formed by depositing BPhen to a thickness of 30 nm over the layer 1114 for controlling electron transfer by an evaporation method using resistance heating.

Then, an electron-injecting layer 1116 was formed by depositing lithium fluoride (LiF) to a thickness of 1 nm over the electron-transporting layer 1115.

Finally, a second electrode 1102 was formed by depositing aluminum to a thickness of 200 nm by an evaporation method using resistance heating. Thus, a light-emitting element 3 of the present invention was formed.

The thus obtained light-emitting element 3 of the present invention was put into a glove box under a nitrogen atmosphere so that the light-emitting element was sealed from atmospheric air. Then, the operating characteristics of the light-emitting element 3 were measured. Note that the measurement was conducted at room temperature (atmosphere kept at 25° C.).

Figure 19:
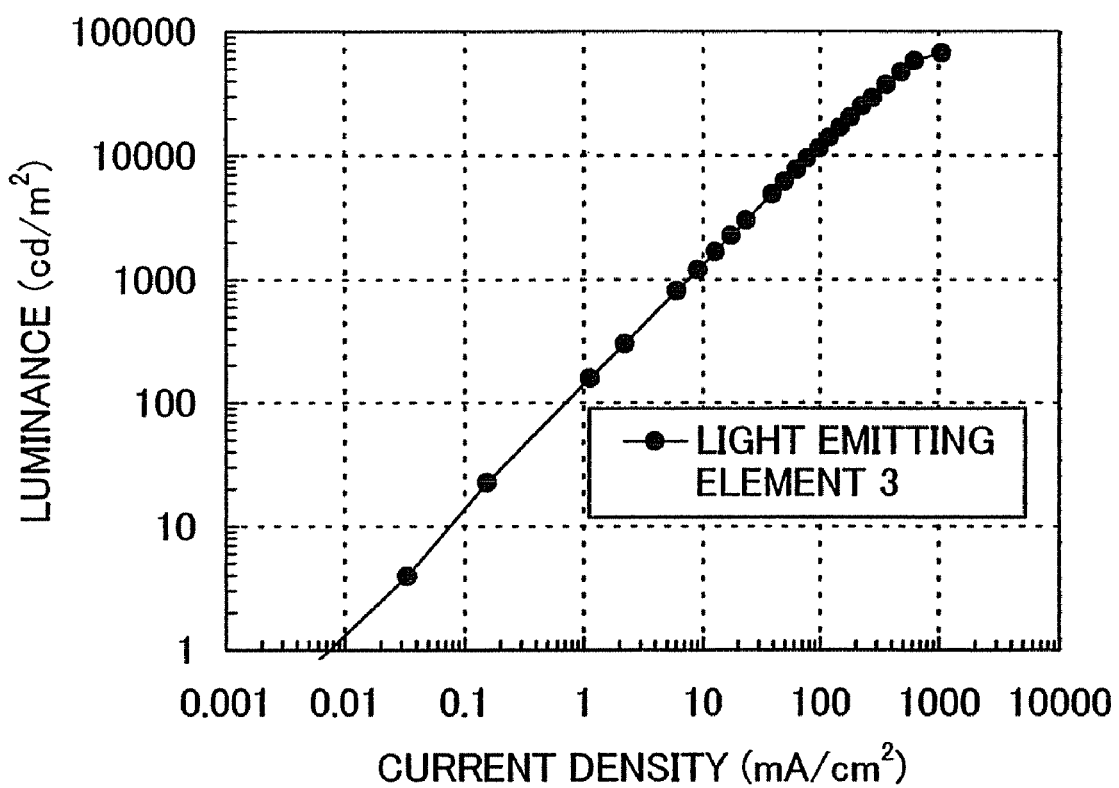
FIG. 19 is a graph showing current density vs. luminance characteristics of a light-emitting element 3 according to an aspect of the present invention.
Figure 20:
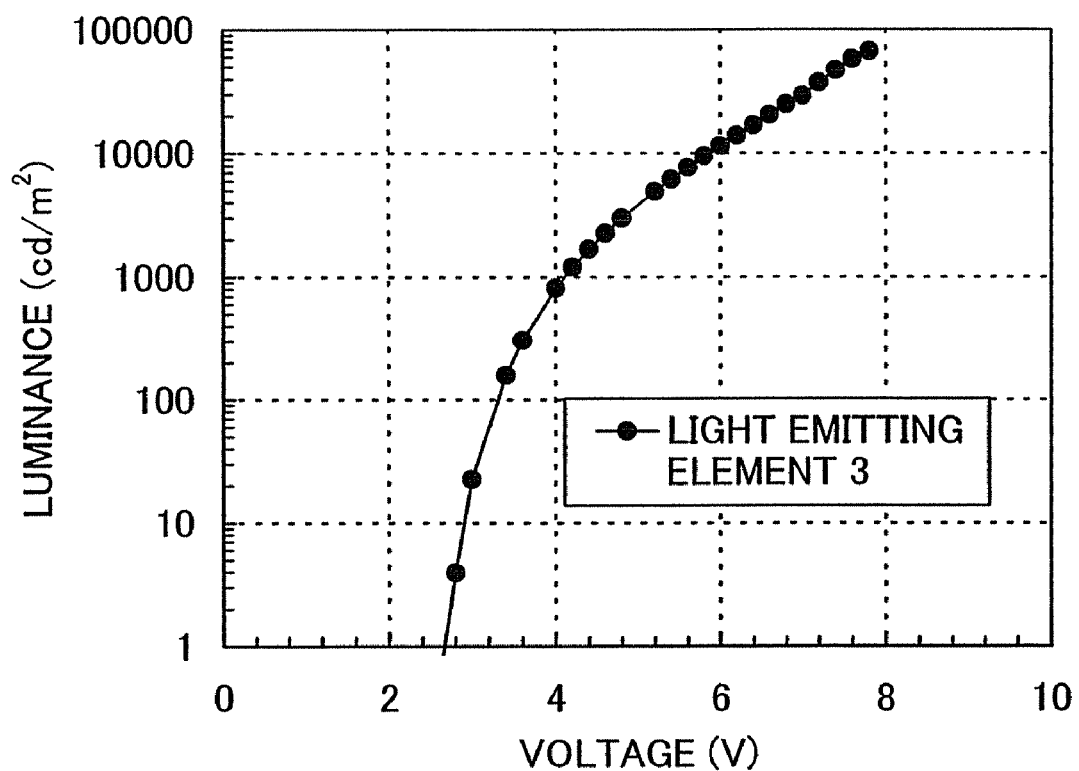
FIG. 20 is a graph showing voltage vs. luminance characteristics of the light-emitting element 3 according to an aspect of the present invention.
Figure 21:
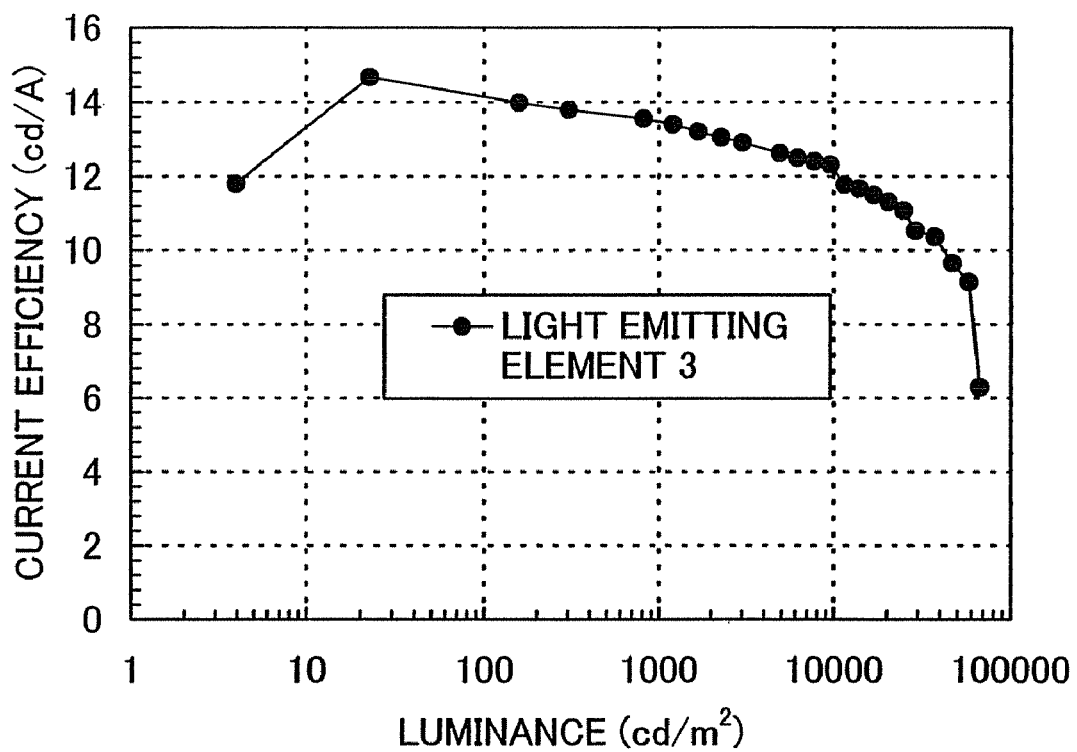
FIG. 21 is a graph showing luminance vs. current efficiency characteristics of the light-emitting element 3 according to an aspect of the present invention.
Figure 22:
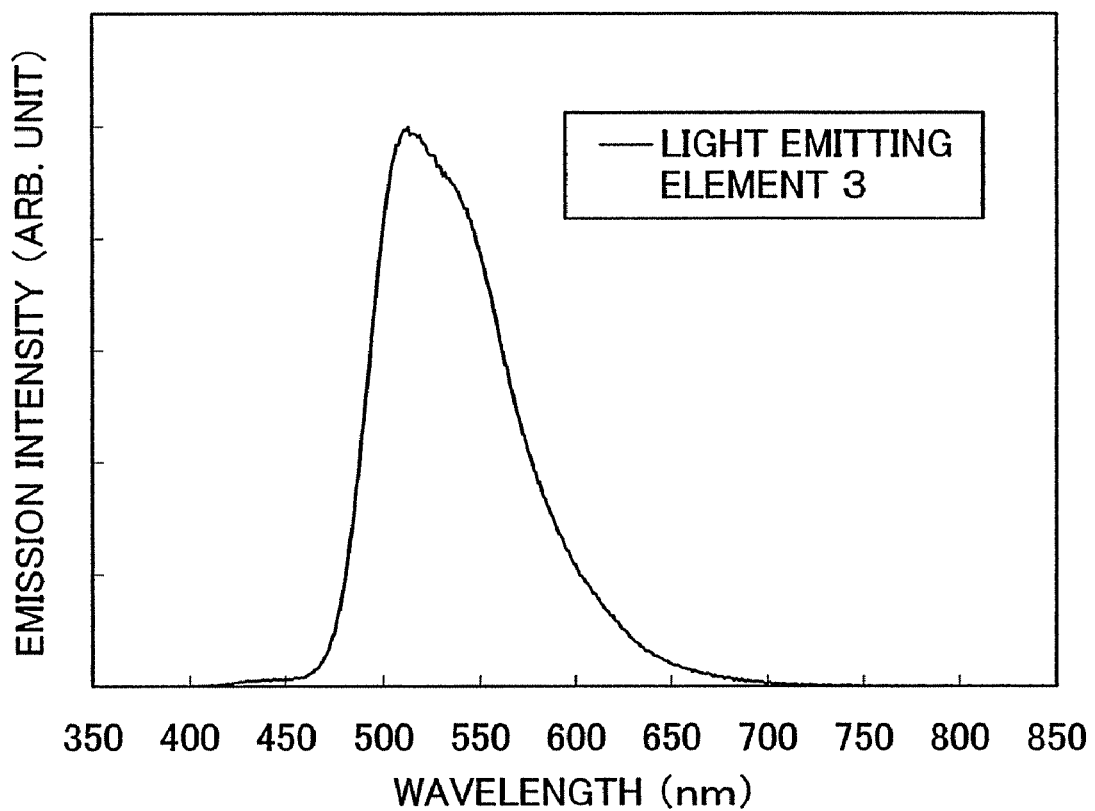
FIG. 22 shows an emission spectrum of the light-emitting element 3 of the present invention.

FIG. 19 shows the current density vs. luminance characteristics of the light-emitting element 3. FIG. 20 shows the voltage vs. luminance characteristics of the light-emitting element 3. FIG. 21 shows the luminance vs. current efficiency characteristics of the light-emitting element 3. FIG. 22 shows the emission spectrum of the light-emitting element 3 at a current supply of 1 mA. The emission color of the light-emitting element 3 was located at the CIE chromaticity coordinates of (x=0.29, y=0.61) at the luminance of 3010 cd/m$^2$, and green emission which derived from 2PCAPA was obtained, similar to the light-emitting element and the reference light-emitting element 2 of Example 1. Thus, similar to the light-emitting element 1, the light-emitting element 3 has excellent color purity. In addition, the current efficiency and driving voltage of the light-emitting element 3 at the luminance of 3010 cd/m$^2$ were 12.9 cd/A and 4.8 V, respectively.

Figure 23:
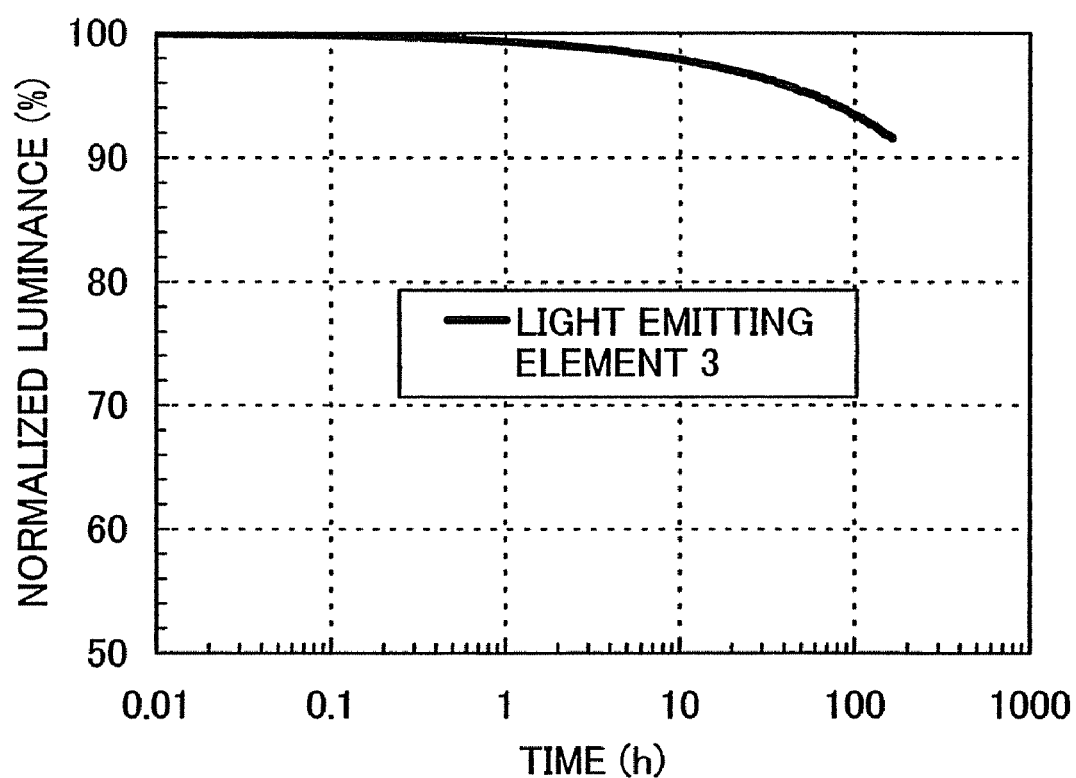
FIG. 23 shows a result of a continuous lighting test in which the light-emitting element 3 of the present invention was continuously lit by constant current driving.

FIG. 23 shows the result of a continuous lighting test in which the light-emitting element 3 was continuously lit by constant current driving with the initial luminance set at 5000 cd/m$^2$ (the vertical axis indicates the relative luminance on the assumption that 5000 cd/m$^2$ is 100%). From the results in FIG. 23, the light-emitting element 3 exhibits 92% of the initial luminance even after 160 hours, and was proved to have long lifetime, similar to the light-emitting element 1. Therefore, a long-lifetime light-emitting element can be obtained by applying the present invention.

Example 3

Example 3 will specifically describe a synthesis example of a quinoxaline derivative of the present invention, 2,3,2',3'-tetrakis(4-fluorophenyl)-6,6'-biquinoxaline (abbreviation: FDPQ2) represented by the structural formula (101), which was used in Example 1. Note that FDPQ2 was used as the second organic compound having an electron-trapping property in the layer 1114 for controlling electron transfer in the light-emitting element 1 in Example 1 (see FIG. 12).

(101)

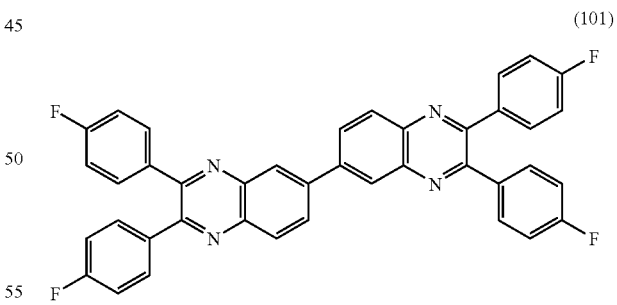

<Synthesis Example of FDPQ2>

First, 2.2 g (10 mmol) of 3,3'-diaminobenzidine, 5.2 g (20 mmol) of 4,4'-difluorobenzyl, and 100 mL of chloroform were put into a 500 mL three-neck flask. This solution was refluxed at 80° C. for about 12 hours, and a light-yellow solid was precipitated. This solid was collected by suction filtration. On the other hand, a filtrate was washed with water and hydrochloric acid (1.0 mol/L), then an organic layer was washed with a saturated sodium bicarbonate water solution and was dried with magnesium sulfate. This mixture was filtrated naturally to remove magnesium sulfate, and the filtrate was condensed to give a light yellow solid. This solid and the light-yellow solid collected immediately after the reaction were put together and subjected to recrystallization by ethanol, to give 6.0 g of an objective substance, 2,3,2',3'-tetrakis (4-fluorophenyl)-6,6'-biquinoxaline (abbreviation: FDPQ2) which was a light-yellow powdered solid in 94% yield. Then, 2.4 g of the obtained light-yellow powdered solid was purified by a train sublimation method. The condition for sublimation purification was that the pressure was 7.8 Pa, the argon gas flow rate was 3.0 mL/min, and heating temperature was 300° C. After the sublimation purification, 2.2 g of FDPQ2, light-yellow powdered solid was obtained in 94% yield. A synthesis scheme of FDPQ2 was shown below.

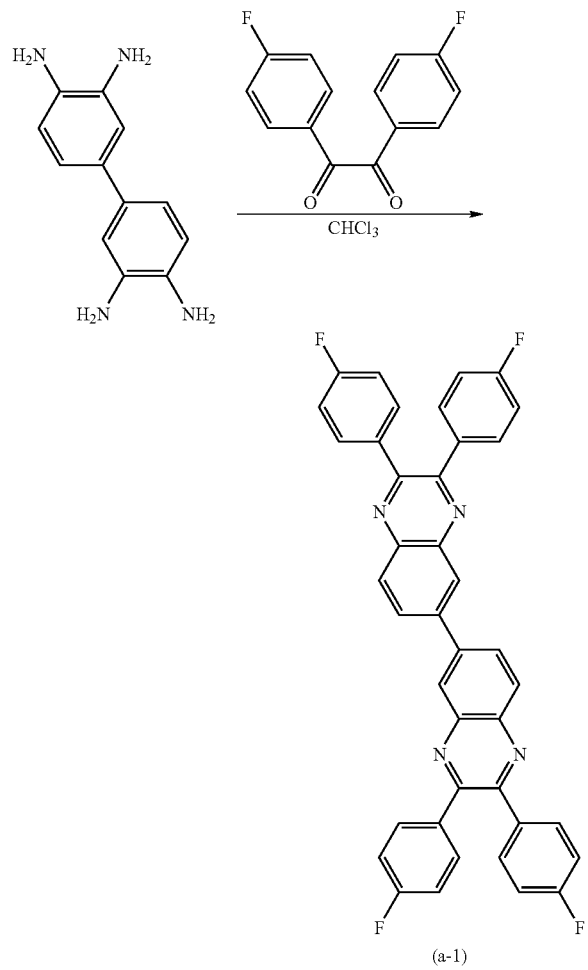

Figure 24:
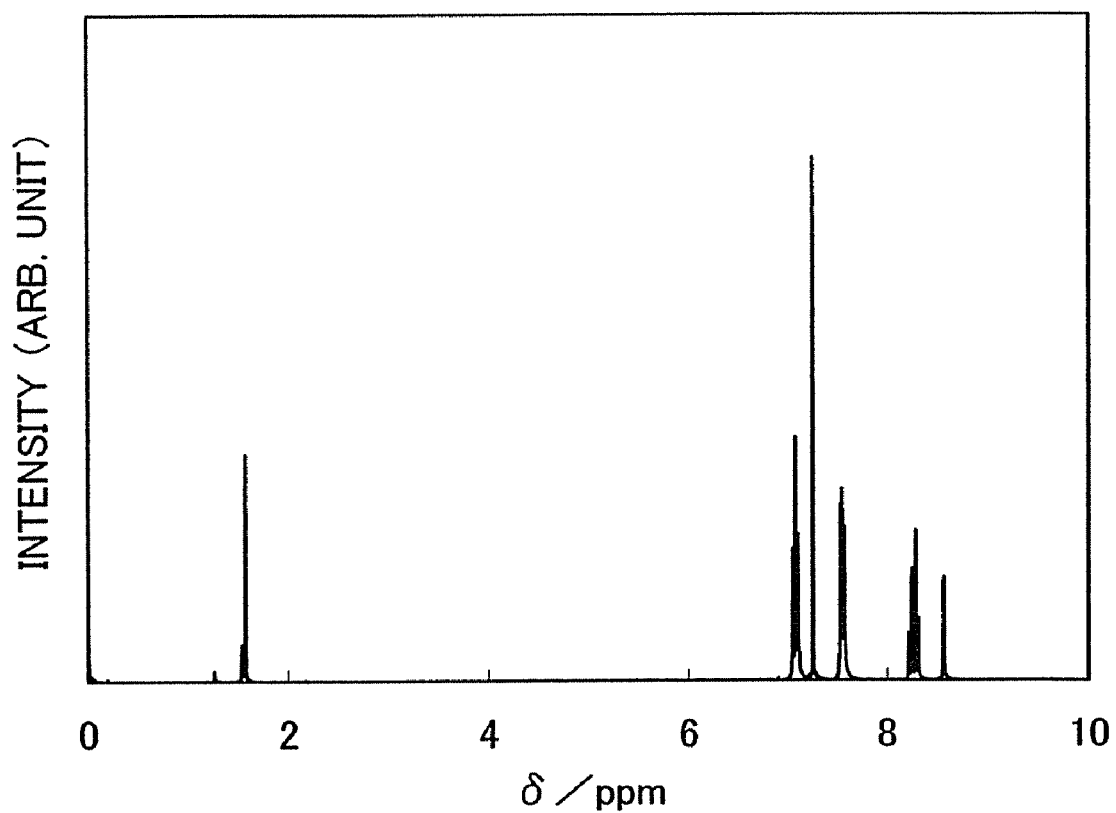
FIG. 24 is a $^1$H NMR chart of a quinoxaline derivative, FDPQ2, according to an aspect of the present invention.

A $^1$H-NMR (nuclear magnetic resonance spectroscopy) analysis result of the light-yellow powdered solid that was obtained by the above synthesis method is shown. FIG. 24 is a $^1$H-NMR chart diagram. This analysis result elucidates the quinoxaline derivative of the present invention, represented by the above structural formula (101), 2,3,2',3'-tetrakis(4-fluorophenyl)-6,6'-biquinoxaline (abbreviation: FDPQ2) was obtained in this synthesis example.

$^1$H-NMR (CDCl$_3$, 300 MHz): δ=7.05-7.12 (m, 8H), 7.54 (d, J=5.4 Hz, 4H), 7.57 (d, J=5.4 Hz, 4H), 8.24 (dd, J$_1$=1.8 Hz, J$_2$=8.8 Hz, 2H), 8.30 (d, J=8.3 Hz, 2H)

Figure 25:
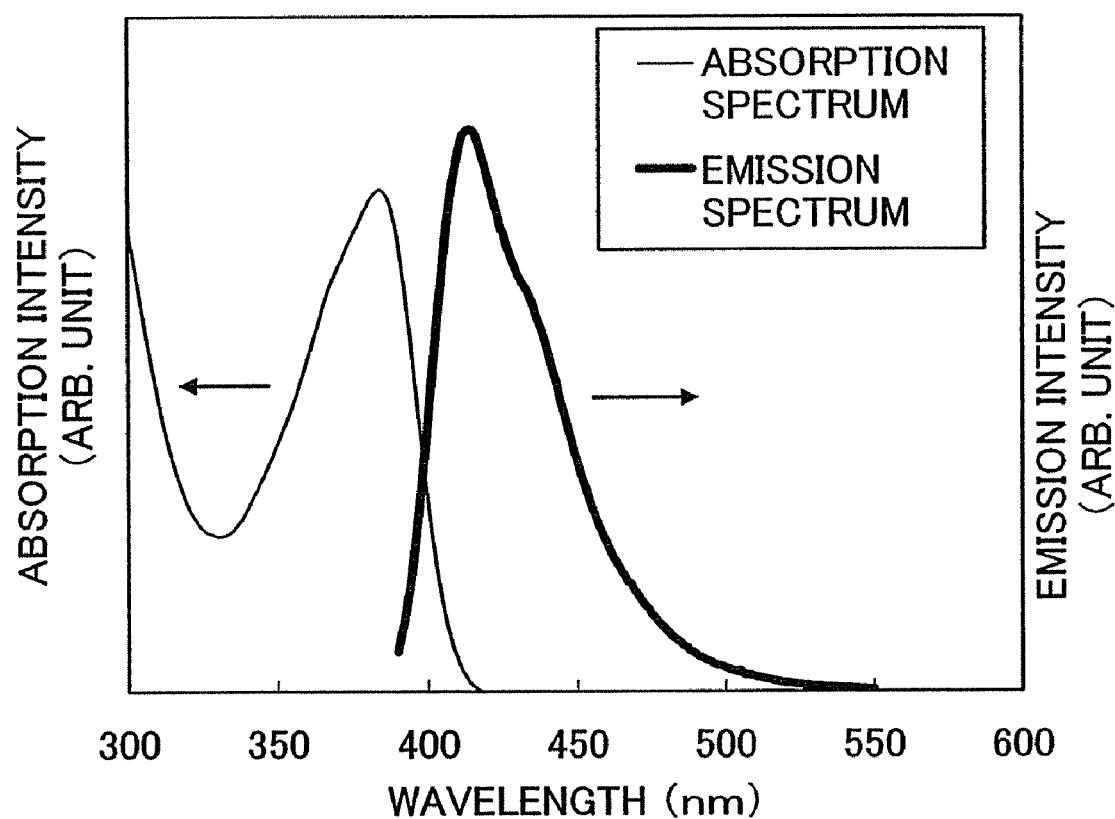
FIG. 25 is a graph showing an absorption spectrum and an emission spectrum of a quinoxaline derivative, FDPQ2 in a toluene solution, according to an aspect of the present invention.
Figure 26:
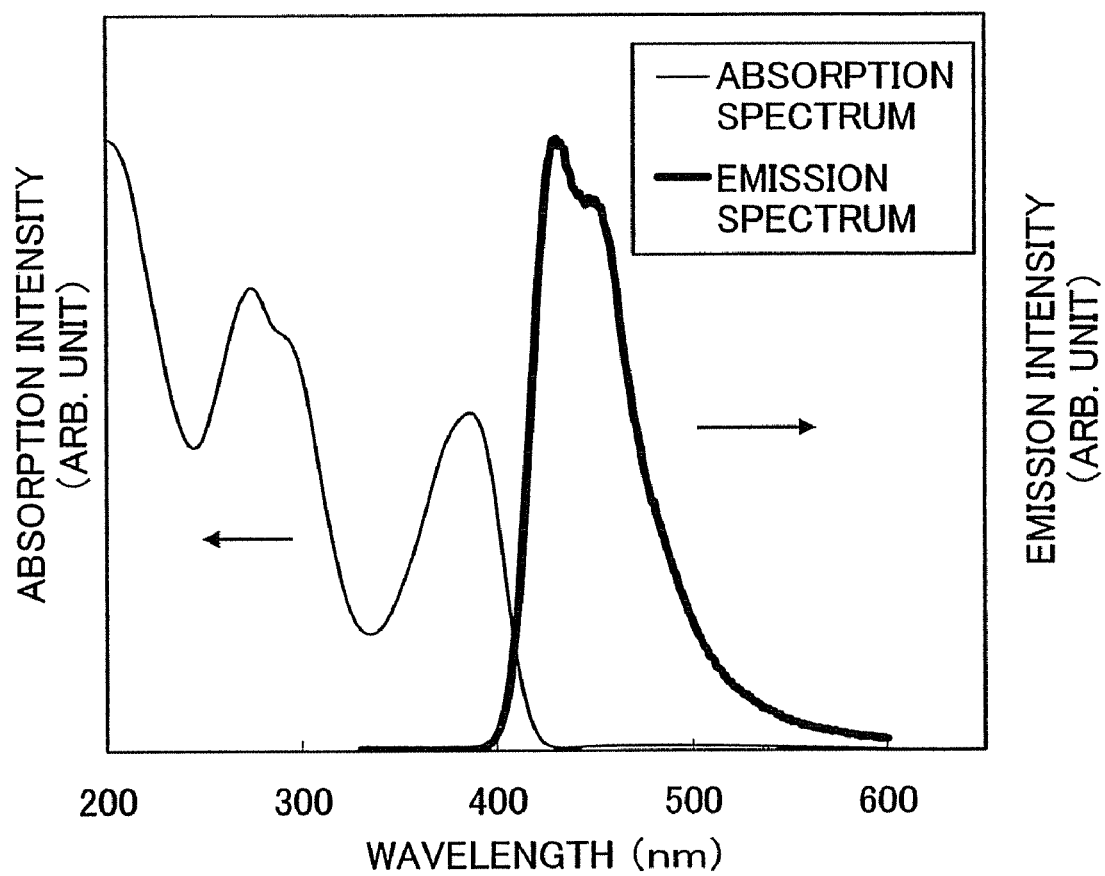
FIG. 26 is a graph showing an absorption spectrum and an emission spectrum of a quinoxaline derivative, FDPQ2 as a deposited film, according to an aspect of the present invention.

FIG. 25 shows an absorption spectrum and an emission spectrum of FDPQ2 in a toluene solution. FIG. 26 shows an absorption spectrum and an emission spectrum of FDPQ2 as a deposited film. In FIGS. 25 and 26, the horizontal axes represent wavelength (nm) and the vertical axes represent absorption intensity and emission intensity. The absorption spectra were measured using an ultraviolet-visible spectrophotometer (type V550, manufactured by Japan Spectroscopy Corporation) and the measurement was conducted at room temperature. The emission spectra were measured using a spectrofluorometer (FS920, by Hamamatsu Photonics K.K.) and the measurement was conducted at room temperature. The excitation wavelengths when the emission spectra were measured were 384 nm for the toluene solution and 313 nm for the deposited film.

Example 4

In Example 4, an energy gap, an emission wavelength and an electron-trapping property of FDPQ2 that was used as the second organic compound having an electron-trapping property in the layer 1114 for controlling electron transfer in the light-emitting element 1 of Example 1 were evaluated.

<Energy Gap of FDPQ2>

The energy gap of FDPQ2 was evaluated. Data of the absorption spectrum in FIG. 26 was converted to tauc plots assuming direct transition to estimate an energy gap in the solid state of FDPQ2. As a result, the energy gap of FDPQ2 was proved to 3.0 eV.

Figure 27:
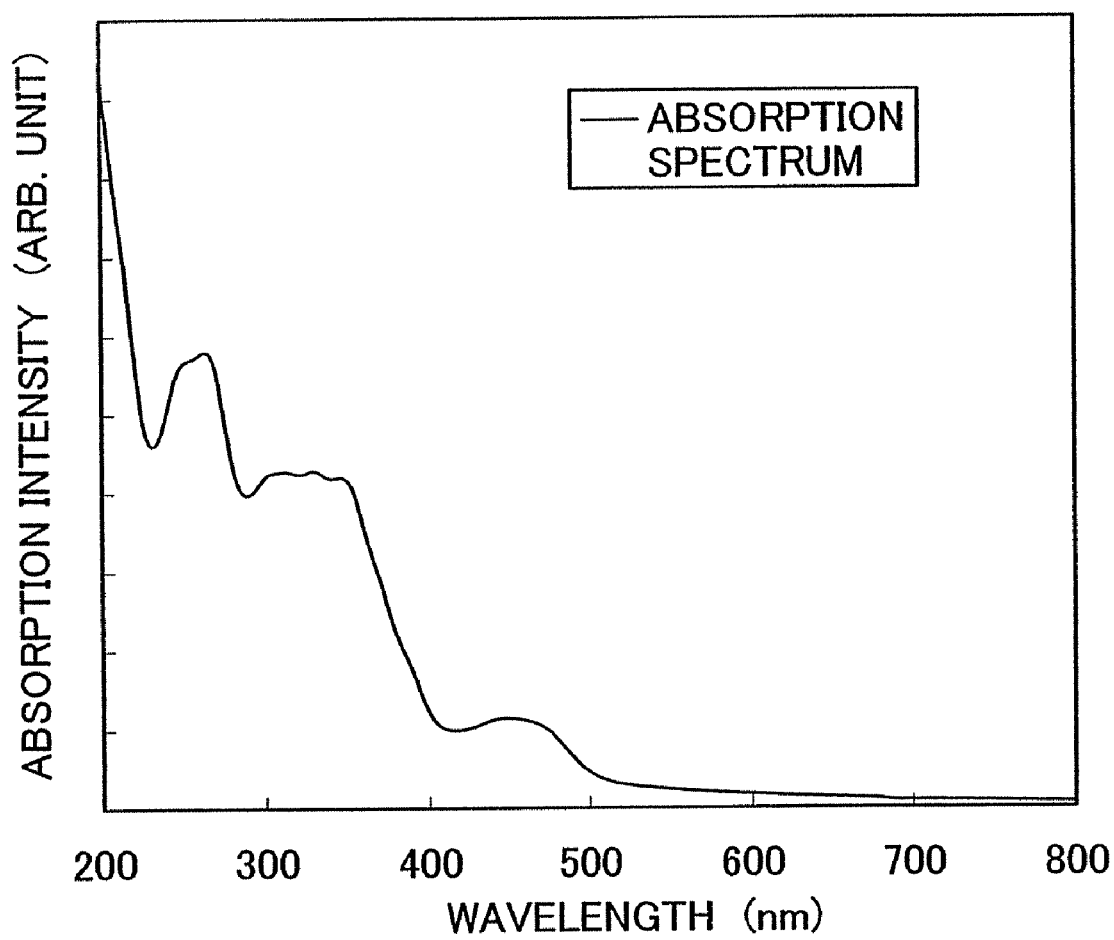
FIG. 27 is a graph showing an absorption spectrum of 2PCAPA that is a light-emitting substance.

On the other hand, FIG. 27 shows an absorption spectrum of 2PCAPA as a deposited film, which was used as a light-emitting substance in the light-emitting element 1 of Example 1. Data of the absorption spectrum in FIG. 27 was converted to tauc plots assuming direct transition to estimate an energy gap in the solid state of 2PCAPA. As a result, the energy gap of 2PCAPA was proved to 2.5 eV.

Accordingly, it is found that the energy gap of FDPQ2 used as the second organic compound having an electron-trapping property is larger than the energy gap of the light-emitting substance. In addition, the energy gap of FDPQ2 is 3.0 eV or larger and FDPQ2 is preferably used for the present invention.

<Emission Wavelength of FDPQ2>

According to FIG. 25 and FIG. 26, the peaks of the emission wavelength of FDPQ2 were 415 nm in the toluene solution and 430 nm in the deposited film, and thus it is said that FDPQ2 has a peak (greater than or equal to 350 nm and less than or equal to 450 nm) of the emission wavelength that is preferable in the present invention, <Electron-Trapping Property of FDPQ2>

The electron-trapping property of FDPQ2 was evaluated. Reduction characteristics of Alq that is the first organic compound having an electron-transporting property used in Example 1 and FDPQ2 that is the second organic compound having an electron-trapping property were measured by cyclic voltammetry (CV) measurement, and from the measurement, LUMO levels of Alq and FDPQ2 were obtained. An electrochemical analyzer (ALS model 600A or 600C manufactured by BAS Inc.) was used for the measurement.

As for a solution used for the CV measurement, dehydrated dimethylformamide (DMF, product of Sigma-Aldrich Inc., 99.8%, catalog No. 22705-6) was used as a solvent, and Tetra-n-butylammonium perchlorate (n-Bu$_4$NClO$_4$, product of Tokyo Chemical Industry Co., Ltd., catalog No. T0836), which was a supporting electrolyte, was dissolved in the solvent such that the concentration of tetra-n-butylammonium perchlorate was 100 mmol/L. Further, the object to be measured was also dissolved in the solvent such that the concentration thereof was 1 mmol/L. In addition, a platinum electrode (a PTE platinum electrode, product of BAS Inc.) was used as a working electrode; a platinum electrode (a VC-3 Pt counter electrode (5 cm), product of BAS Inc.) was used as an auxiliary electrode; and an Ag/Ag$^+$ electrode (an RE5 nonaqueous solvent reference electrode, product of BAS Inc.) was used as a reference electrode. Note that the measurement was conducted at room temperature (20 to 25° C.).

[Calculation of the Potential Energy of the Reference Electrode with respect to the Vacuum Level]

First, potential energy (eV) of the reference electrode (Ag/Ag$^+$ electrode) used in Example 4 with respect to the vacuum level was calculated. That is, the Fermi level of the Ag/Ag$^+$ electrode was calculated. It is known that the oxidation-reduction potential of ferrocene in methanol is +0.610 V [vs. SHE] with respect to a standard hydrogen electrode (Reference: Christian R. Goldsmith et al., J. Am. Chem. Soc., Vol. 124, No. 1, pp. 83-96, 2002). On the other hand, when the oxidation-reduction potential of ferrocene in methanol was calculated using the reference electrode used in Example 4, the result was +0.20 V [vs. Ag/Ag$^+$]. Therefore, it was found that the potential energy of the reference electrode used in Example 4 was lower than that of the standard hydrogen electrode by 0.41 [eV]. Note that the concentration of ferrocene was 1 mmol/L.

Here, it is also known that the potential energy of the standard hydrogen electrode with respect to the vacuum level is −4.44 eV (Reference: Toshihiro Ohnishi and Tamami Koyama, High molecular EL material, Kyoritsu Shuppan, pp. 64-67). Accordingly, the potential energy of the reference electrode used in Example 4 with respect to the vacuum level could be calculated as follows: −4.44−0.41=−4.85 [eV].

(CV Measurement Example of FDPQ2)

Figure 28:
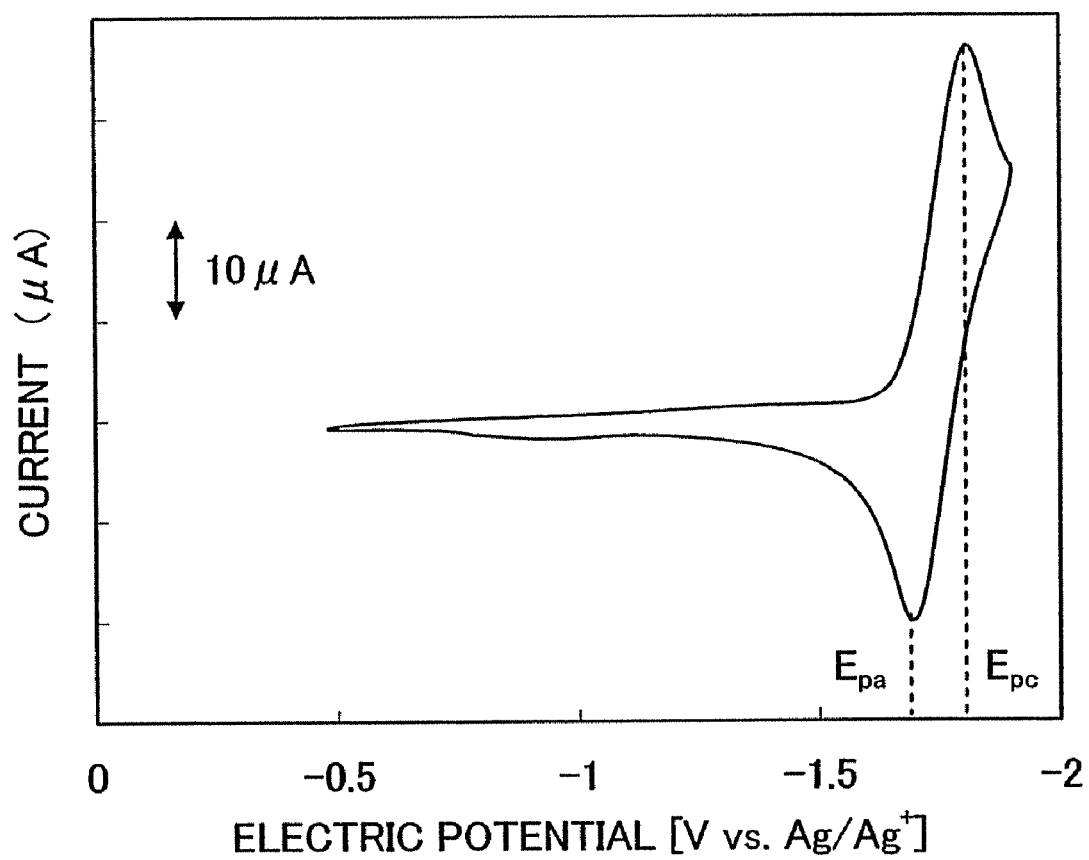
FIG. 28 is a graph showing reduction characteristics of a quinoxaline derivative, FDPQ2 according to the present invention.

The reduction characteristics of FDPQ2 were observed by cyclic voltammetry (CV) measurement. The scan rate was set at 0.1 V/sec. FIG. 28 shows the measurement result. Note that the measurement of the reduction characteristics was conducted by the steps of: scanning the potential of the working electrode with respect to the reference electrode in ranges of (1) −0.48 V to −1.90 V, and then (2) −1.90 V to −0.48 V. Note that the concentration of FDPQ2 was 10 mmol/L.

As shown in FIG. 28, it can be seen that a reduction peak potential $E_{pc}$ is −1.81 V and an oxidation peak potential $E_{pa}$ is −1.69 V. Therefore, a half-wave potential (an intermediate potential between $E_{pc}$ and $E_{pa}$) can be determined to be −1.75 V. This elucidates that FDPQ2 can be reduced by an electrical energy of −1.75 V [vs. Ag/Ag$^+$], and this energy corresponds to the LUMO level. Here, the potential energy of the reference electrode used in Example 3 with respect to the vacuum level is −4.85 [eV] as described above. Therefore, the LUMO level of FDPQ2 was calculated as follows: −4.85−(−1.75)=−3.10 [eV].

(CV Measurement Example of Alq)

Figure 29:
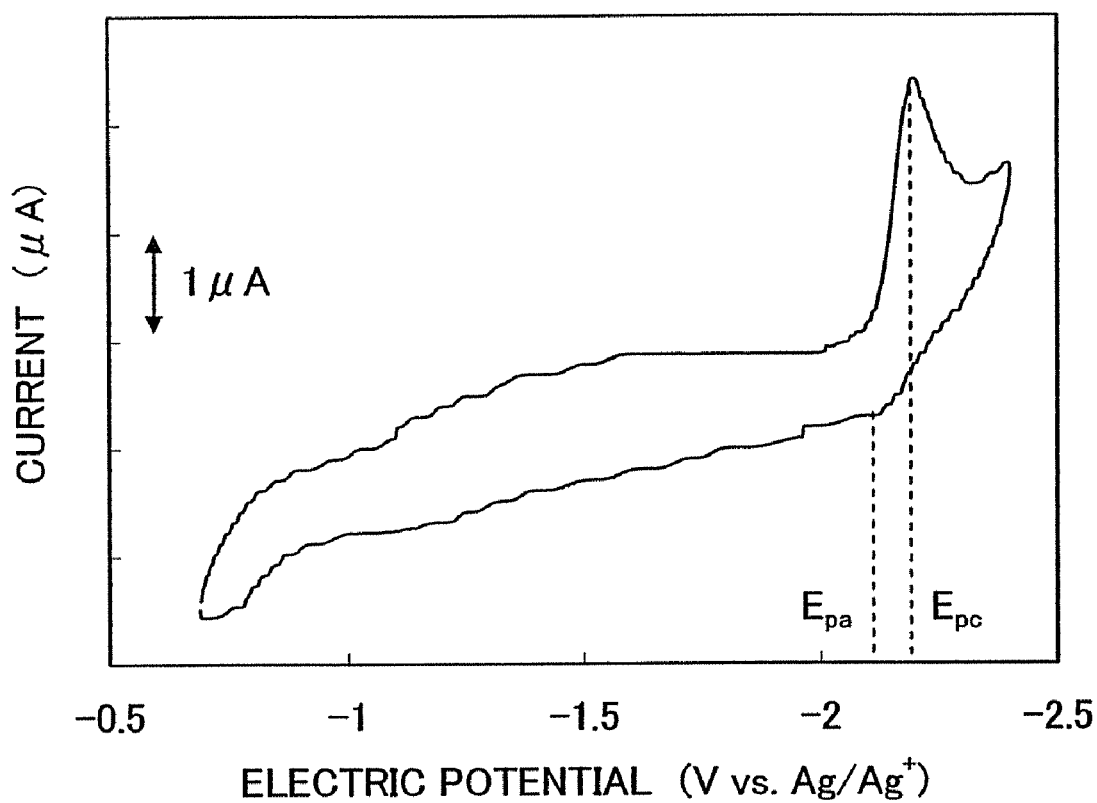
FIG. 29 is a graph showing reduction characteristics of Alq.

The reduction characteristics of Alq were observed by cyclic voltammetry (CV) measurement. The scan rate was set at 0.1 V/sec. FIG. 29 shows the measurement result. Note that the measurement of the reduction characteristics was conducted by the steps of: scanning the potential of the working electrode with respect to the reference electrode in ranges of (1) −0.69 V to −2.40 V, and then (2) −2.40 V to −0.69 V. The concentration of Alq was 1 mmol/L.

As shown in FIG. 29, it can be seen that a reduction peak potential $E_{pc}$ is −2.20 V and an oxidation peak potential $E_{pa}$ is −2.12 V. Therefore, a half-wave potential (an intermediate potential between $E_{pc}$ and $E_{pa}$) can be determined to be −2.16 V. This shows that Alq can be reduced by an electrical energy of −2.16 V [vs. Ag/Ag$^+$], and this energy corresponds to the LUMO level. Here, the potential energy of the reference electrode used in Example 3 with respect to the vacuum level is −4.85 [eV] as described above. Therefore, the LUMO level of Alq can be determined to be −4.85−(−2.16) −2.69 [eV].

The above-obtained LUMO levels of FDPQ2 and Alq were compared, and thus it was found that the LUMO level of the FPDQ2 was lower than that of Alq by 0.41 [eV]. This means that FDPQ2 serve as a trap for electrons as a result of addition of FDPQ2 to Alq. Thus, in the layer 1114 for controlling electron transfer in the light-emitting element 1 of Example 1, FDPQ2 serve as a trap for electrons. The depth of the trap is 0.3 eV or higher.

Example 5

In Example 5, an energy gap, an emission wavelength and an electron-trapping property of FDPQ that was used as the second organic compound having an electron-trapping property in the layer 1114 for controlling electron transfer in the light-emitting element 3 of Example 2 were evaluated.

<Energy Gap of FDPQ>

Figure 30:
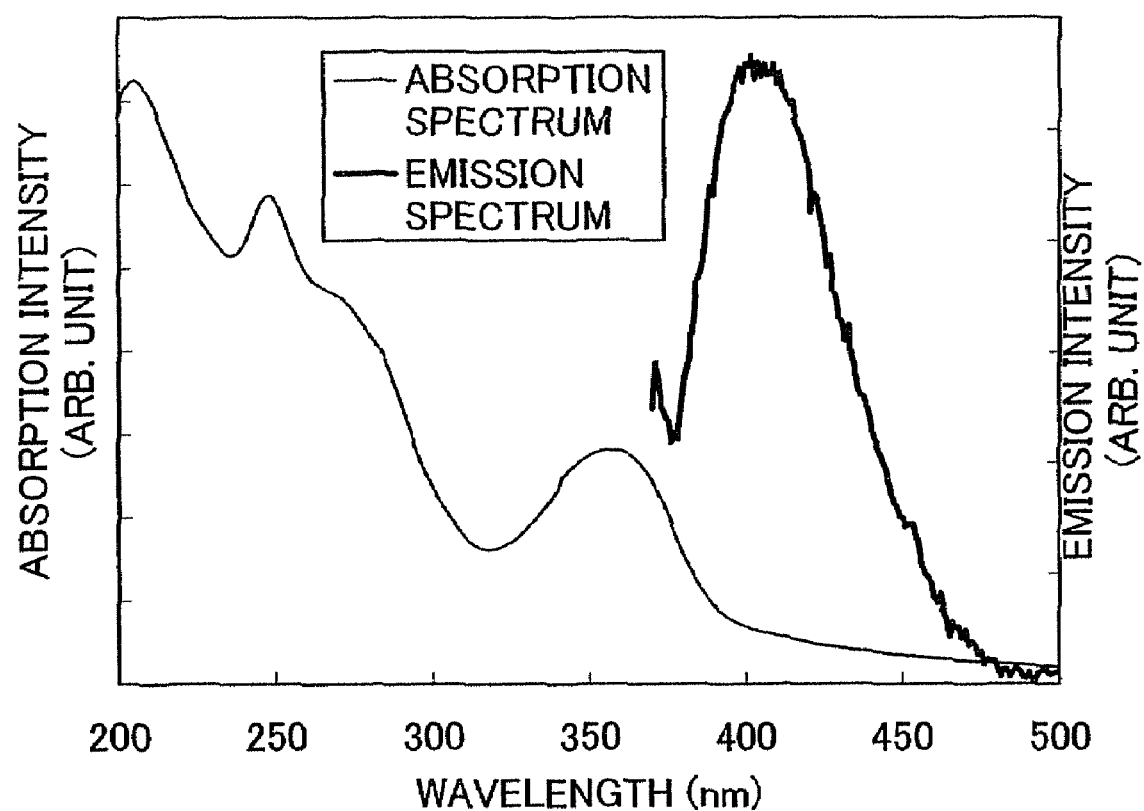
FIG. 30 is a graph showing an absorption spectrum and an emission spectrum of a quinoxaline derivative, FDPQ as a deposited film.

The energy gap of FDPQ was evaluated. FIG. 30 shows an absorption spectrum of a deposited film of FDPQ. Data of the absorption spectrum in FIG. 30 is converted to tauc plots assuming direct transition to estimate an energy gap in the solid state of FDPQ. As a result, the energy gap of FDPQ was proved to be 3.2 eV.

On the other hand, the energy gap of 2PCAPA, which was used as the light-emitting substance in the light-emitting element 3 of Example 2, was 2.5 eV as described in Example 4. Accordingly, it is found that the energy gap of FDPQ used as the second organic compound having an electron-trapping property is larger than the energy gap of the light-emitting substance. In addition, the energy gap of FDPQ is 3.0 eV or larger and FDPQ is preferably used for the present invention.

<Emission Wavelength of FDPQ>

FIG. 30 shows an emission spectrum of a deposited film of FDPQ. Note that the excitation wavelength was set 357 nm. According to FIG. 30, the peak of the emission wavelength was 406 nm as the deposited film and thus, FDPQ has a peak (greater than or equal to 350 nm and less than or equal to 450 nm) of the emission wavelength that is preferable in the present invention.

<Electron-Trapping Property of FDPQ>

The electron-trapping property of FDPQ was evaluated. Reduction characteristics of Alq that is the first organic compound having an electron-transporting property used in Example 2 and FDPQ that was the second organic compound having an electron-trapping property were measured by cyclic voltammetry (CV) measurement, and from the measurement, LUMO levels of Alq and FDPQ were obtained. The measurement was conducted in the same manner as that in Example 4.

(CV Measurement Example of FDPQ)

Figure 31:
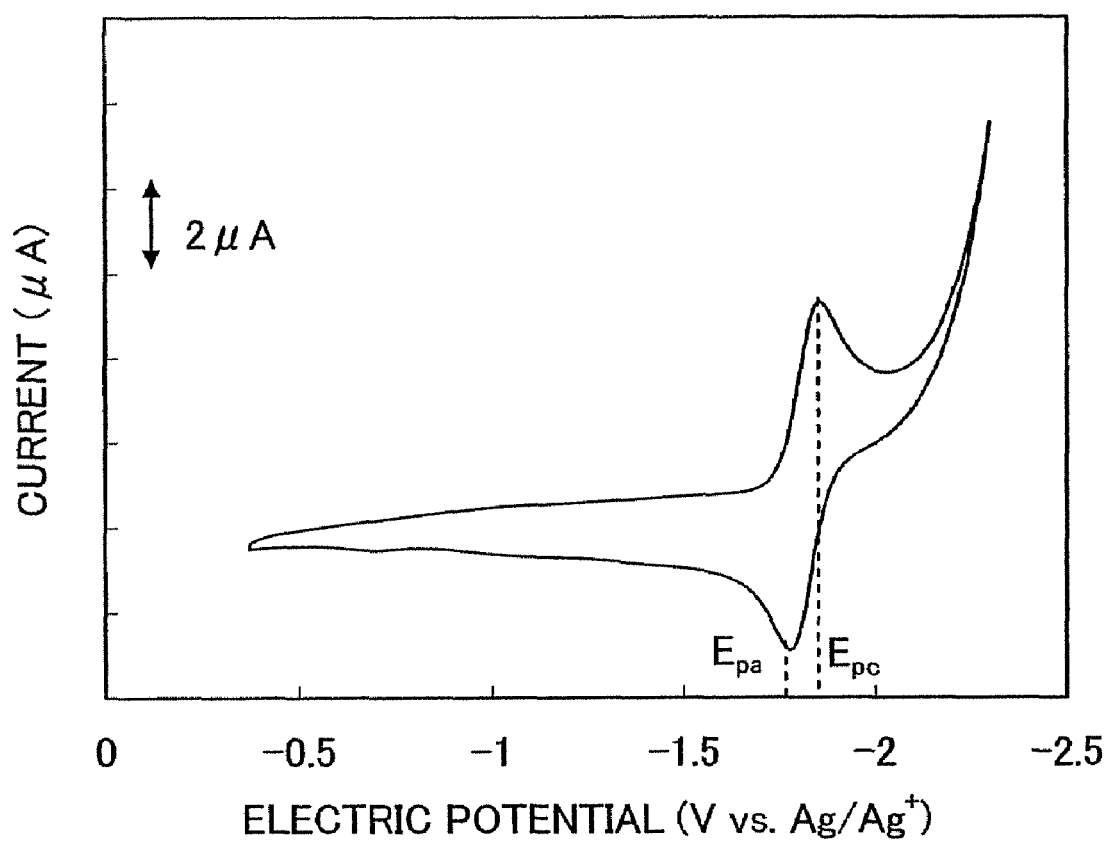
FIG. 31 is a graph showing reduction characteristics of a quinoxaline derivative, FDPQ.

The reduction characteristics of FDPQ were observed by cyclic voltammetry (CV) measurement. The scan rate was set at 0.1 V/sec. FIG. 31 shows the measurement result. Note that the measurement of the reduction characteristics was conducted by the steps of: scanning the potential of the working electrode with respect to the reference electrode from −0.37 V to −2.30 V, and then from −2.30 V to −0.37 V. The concentration of FDPQ was 10 mmol/L.

As shown in FIG. 31, it can be seen that a reduction peak potential $E_{pc}$ is −1.86 V and an oxidation peak potential $E_{pa}$ is −1.78 V. Therefore, a half-wave potential (an intermediate potential between $E_{pc}$ and $E_{pa}$) can be determined to be −1.82 V. This shows that FDPQ can be reduced by an electrical energy of −1.82 V [vs. Ag/Ag$^+$], and this energy corresponds to the LUMO level. Here, the potential energy of the reference electrode with respect to the vacuum level is −4.85 [eV] as described above. Therefore, the LUMO level of FDPQ was calculated as follows: −4.85−(−1.82)=−3.03 [eV].

In addition, the LUMO level of Alq was −2.69 eV as described in Example 4. The LUMO levels obtained above of FDPQ and Alq were compared, and thus it was found that the LUMO level of the FPDQ was lower than that of Alq by 0.34 [eV]. This means that FDPQ serve as a trap for electrons as a result of addition of FDPQ to Alq. Thus, in the layer 1114 for controlling electron transfer in the light-emitting element 1 of Example 1, FDPQ serve as a trap for electrons. The depth of the trap is 0.3 eV or larger.

Example 6

Example 6 will specifically describe light-emitting elements (light-emitting element 4 and light-emitting element 5) of the present invention with reference to FIG. 12. A chemical formula of a material used in Example 6 is shown below. Note that organic compounds described in Example 1 are omitted.

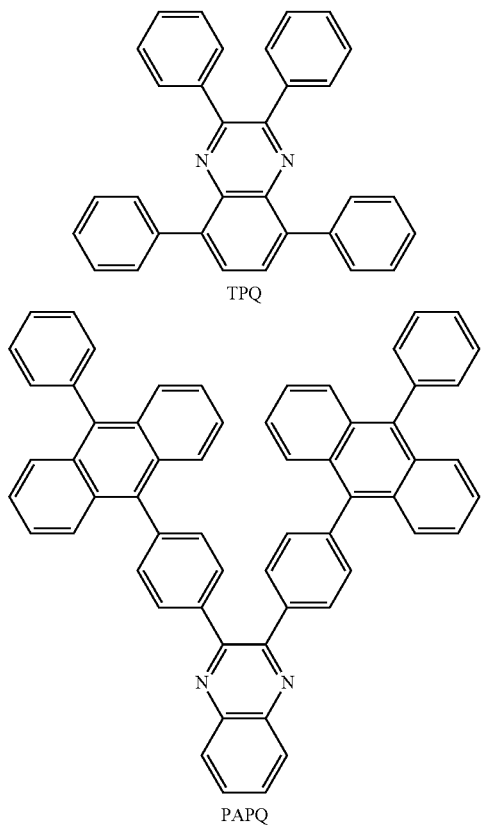

TPQ

PAPQ (Light-Emitting Element 4 and Light-Emitting Element 5)

First, ITO including silicon oxide was deposited over a glass substrate 1100 by a sputtering method, and thereby a first electrode 1101 was formed. Note that the thickness of the first electrode 1101 was 110 nm and the electrode area was 2 mm×2 mm.

Next, the substrate over which the first electrode was formed was fixed to a substrate holder provided in a vacuum evaporation apparatus, such that a surface over which the first electrode was formed faced down. Then, after reducing the pressure of the vacuum evaporation apparatus to about 10$^{-4}$ Pa, a layer 1111 including a composite material, which was formed of an organic compound and an inorganic compound, was formed over the first electrode 1101 by co-evaporating NPB and molybdenum(VI) oxide. The film thickness of the layer 1111 was to be 50 nm, and the ratio of NPB and molybdenum(VI) oxide was adjusted to be 4:1 (=NPB:molybdenum oxide) in weight ratio. Note that the co-evaporation method is an evaporation method in which evaporation is carried out from a plurality of evaporation sources at the same time in one treatment chamber.

Subsequently, a film of NPB was formed at a thickness of 10 nm by an evaporation method using the resistance heating system, thereby forming a hole-transporting layer 1112.

Then, a light-emitting layer 1113 was formed over the hole-transporting layer 1112. By co-evaporating CzPA and 2PCAPA, the light-emitting layer 1113 with a thickness of 30 nm was formed over the hole-transporting layer 1112. The evaporation rate was adjusted such that the weight ratio of CzPA and 2PCAPA was adjusted to 1:0.05 (=CzPA: 2PCAPA).

Further, a layer 1114 for controlling electron transfer with a thickness of 10 nm was formed over the light-emitting layer 1113. In the case of the light-emitting element 4, Alq that is the first organic compound having an electron-transporting property and 2,3,5,8-tetraphenyl quinoxaline (abbreviation: TPQ) that is the second organic compound having an electron-trapping property were co-evaporated to form the layer 1114 for controlling electron transfer. In the case of the light-emitting element 5, Alq that was the first organic compound having an electron-transporting property and 2,3-bis[4-(10-phenyl-9-antryl)phenyl]quinoxaline (abbreviation: PAPQ) that was the second organic compound having an electron-trapping property were co-evaporated to form the layer 1114 for controlling electron transfer. At this time, the evaporation rate was adjusted such that the weight ratio of Alq and TPQ in the light-emitting element 4 was 1:0.05 (=Alq:TPQ). It was found that energy gaps of TPQ (abbreviation) used in the light-emitting element 4 and PAPQ (abbreviation) used in the light-emitting element 5 were measured in the same manner as those in Examples 4 and 5. The energy gaps of TPQ and PAPQ were proved to be 3.1 [eV] and 2.9 [eV] respectively. TPQ and PAPQ are both quinoxaline derivatives and are organic compounds having an electron-trapping property.

Then, a 30-nm thick Alq was deposited over the layer 1114 for controlling electron transfer by an evaporation method using resistance heating to form an electron-transporting layer 1115.

Furthermore, a film of lithium fluoride (LiF) having a thickness of 1 nm was formed over the electron-transporting layer 1115 to form an electron-injecting layer 1116.

Lastly, a film of aluminum with a film thickness of 200 nm was deposited by the evaporation method using resistance heating to form a second electrode 1102 was formed. Accordingly, light-emitting elements 4 and 5 were fabricated.

The thus obtained light-emitting elements 4 and 5 were sealed in a glove box with a nitrogen atmosphere so as not to expose the light-emitting elements to the air, and then operation characteristics of the light-emitting elements were measured. Note that the measurement was performed at room temperature (an atmosphere kept at 25° C.).

Figure 32:
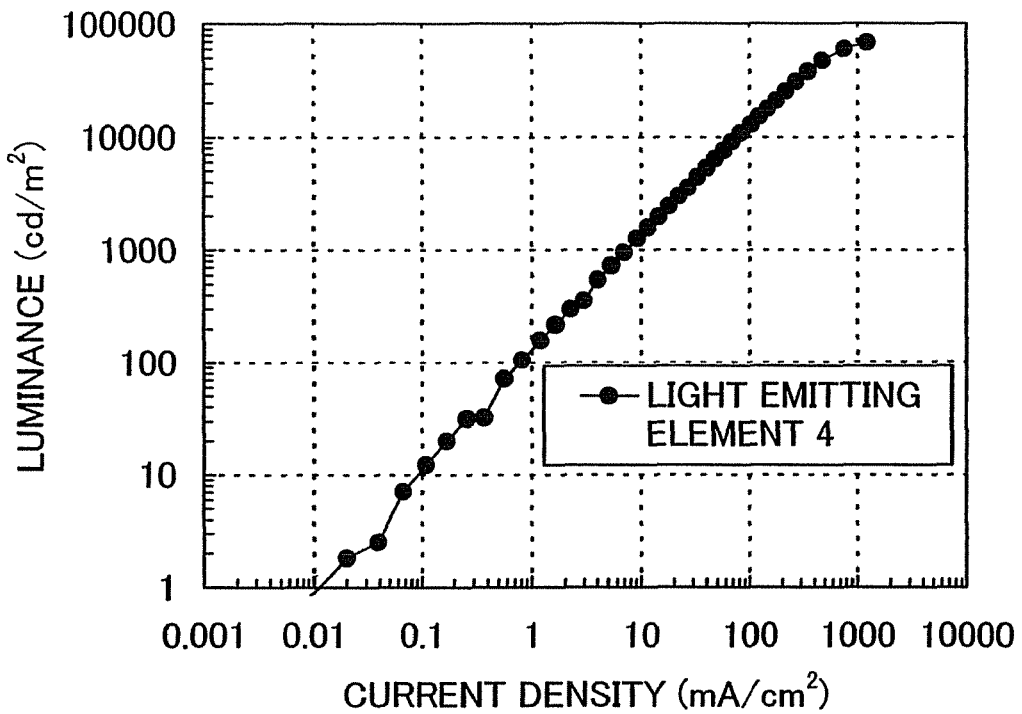
FIG. 32 is a graph showing current density vs. luminance characteristics of a light-emitting element 4 according to an aspect of the present invention.
Figure 33:
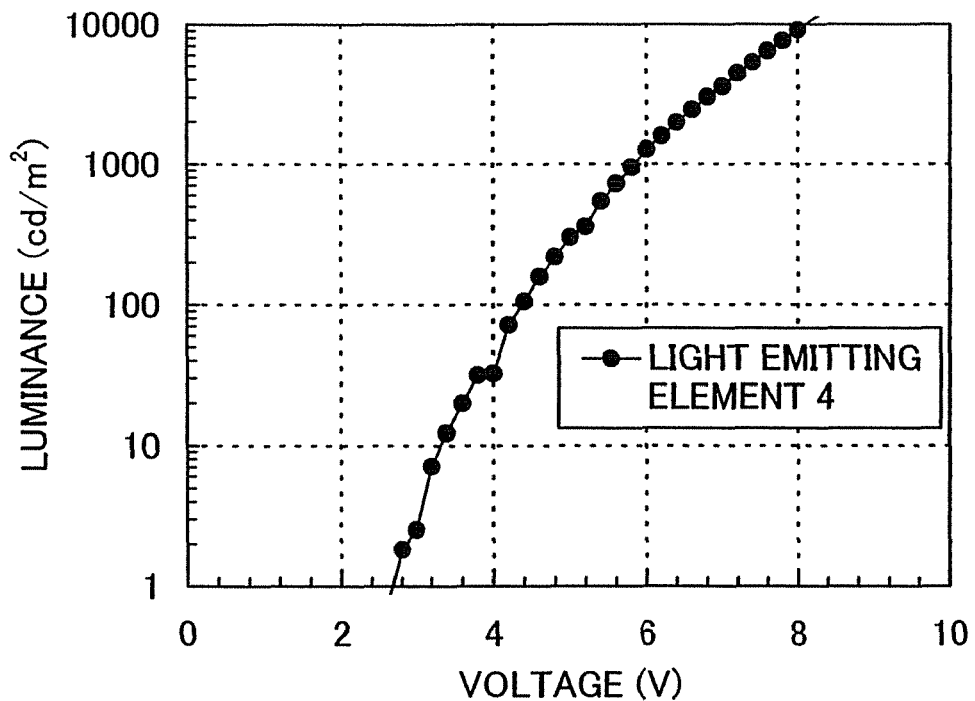
FIG. 33 is a graph showing voltage vs. luminance characteristics of the light-emitting element 4 according to an aspect of the present invention.
Figure 34:
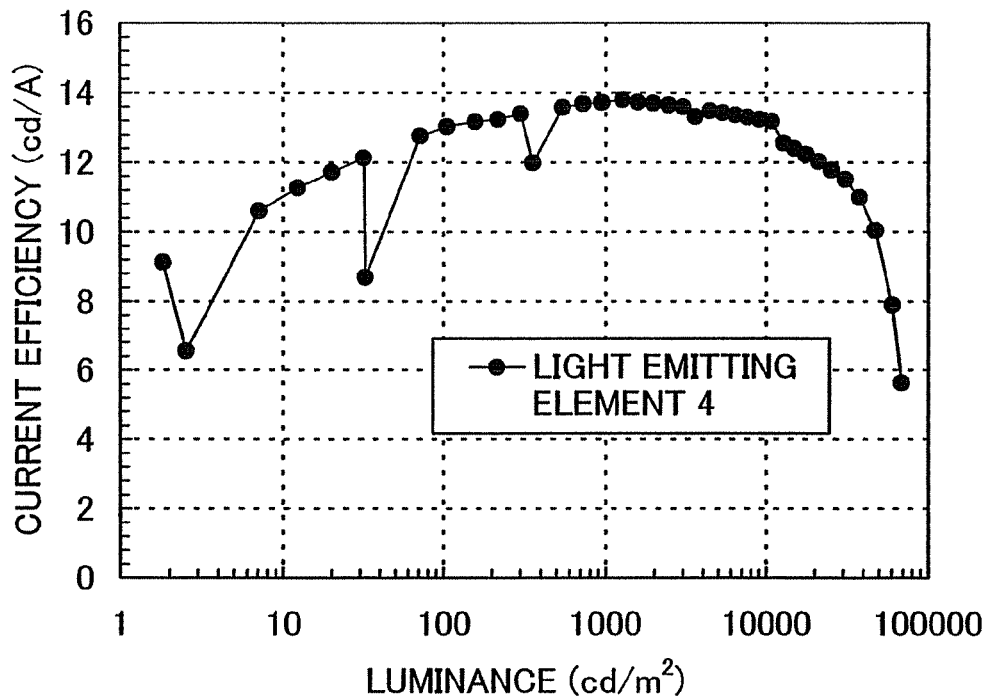
FIG. 34 is a graph showing luminance vs. current efficiency characteristics of the light-emitting element 4 according to an aspect of the present invention.
Figure 35:
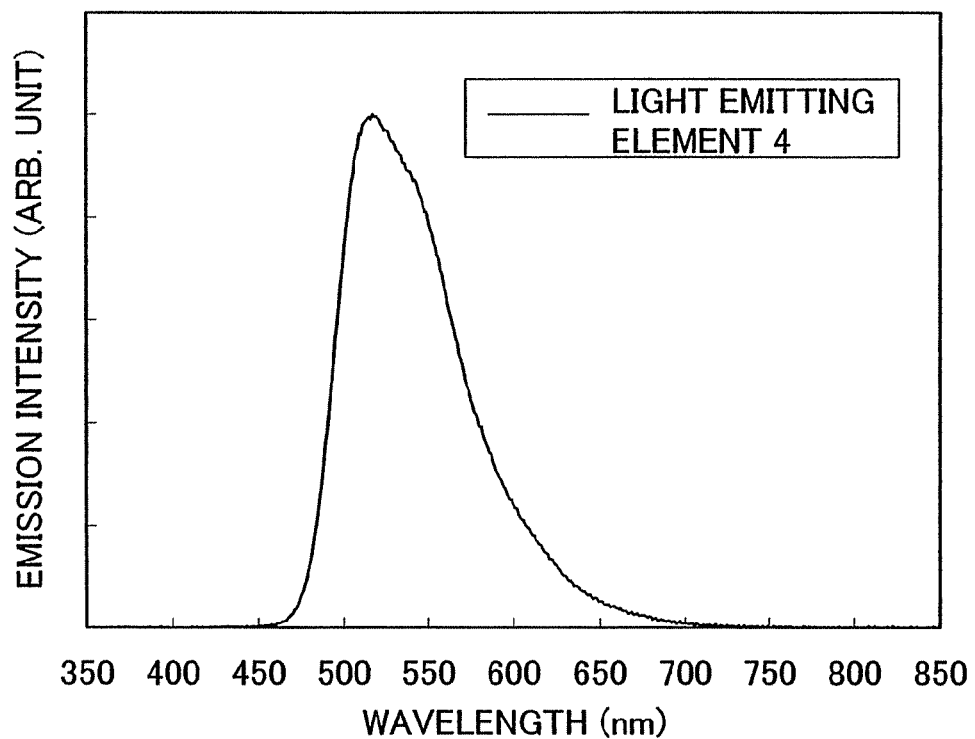
FIG. 35 shows an emission spectrum of the light-emitting element 4 according to an aspect of the present invention.

FIG. 32 shows current density-luminance characteristics of the light-emitting element 4, and FIG. 33 shows voltage-luminance characteristics thereof. FIG. 34 shows luminance-current efficiency characteristics of the light-emitting element. FIG. 35 shows emission spectrum at a current supply of 1 mA of the light-emitting element 4. CIE chromaticity coordinates of the light-emitting element 4 was (x, y)=(0.30, 0.62) at a luminance of 3000 cd/m$^2$. The light-emitting element 4 exhibits green emission derived from 2PCAPA, similar to the light-emitting element 1 of Example 1 and the comparative light-emitting element 2 and the light-emitting element 3 of Example 2. Thus, the light-emitting element 4 has excellent color purity, similar to the light-emitting elements 1 and 3. The current efficiency and driving voltage at a luminance of 3000 cd/m$^2$ were 13.6 cd/A and 6.8 V respectively.

Figure 36:
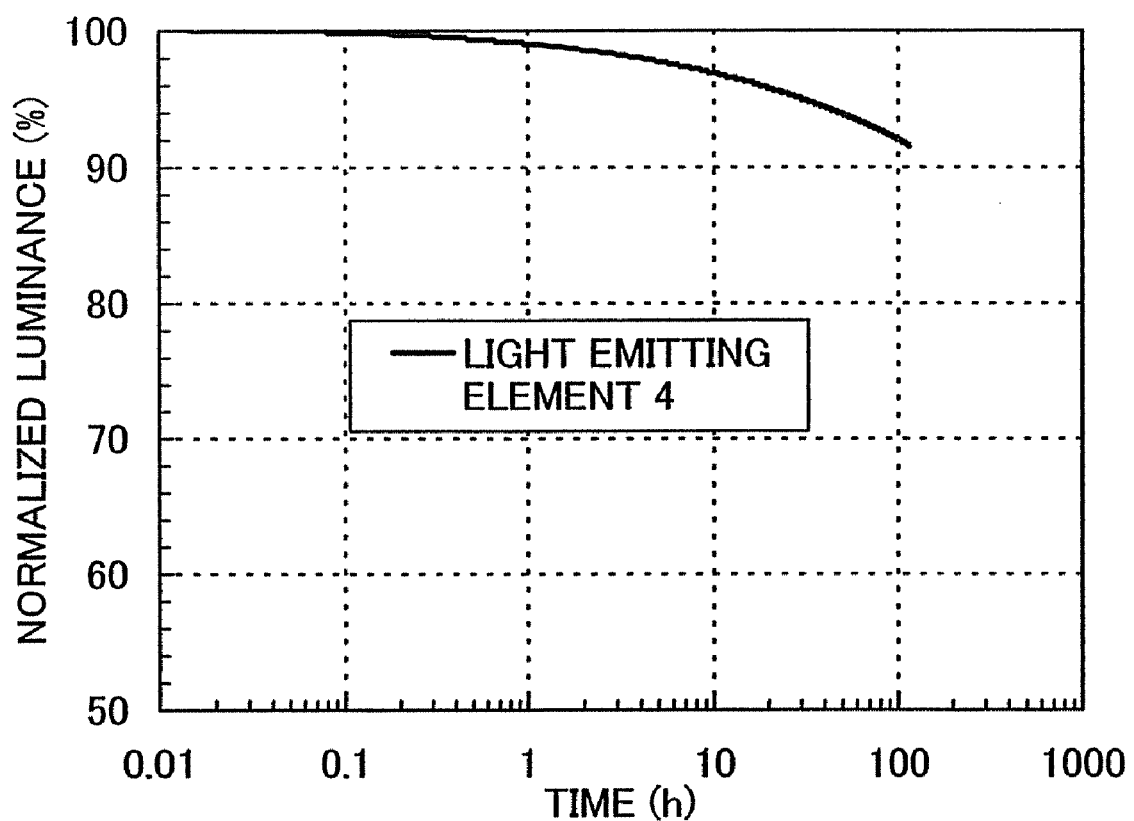
FIG. 36 shows a result of a continuous lighting test in which the light-emitting element 4 of the present invention was continuously lit by constant current driving.

FIG. 36 shows the result of a continuous lighting test in which the light-emitting element 4 was continuously lit by constant current driving with the initial luminance set at 5000 cd/m$^2$ (the vertical axis indicates the relative luminance on the assumption that 5000 cd/m$^2$ is 100%). From the result of FIG. 36, the light-emitting element 4 exhibits 92% of the initial luminance even after 100 hours, which leads to that the light-emitting element 4 has long lifetime, similar to the light-emitting elements 1 and 3. Thus, a light-emitting element having long lifetime can be fabricated in accordance with the present invention.

Figure 37:
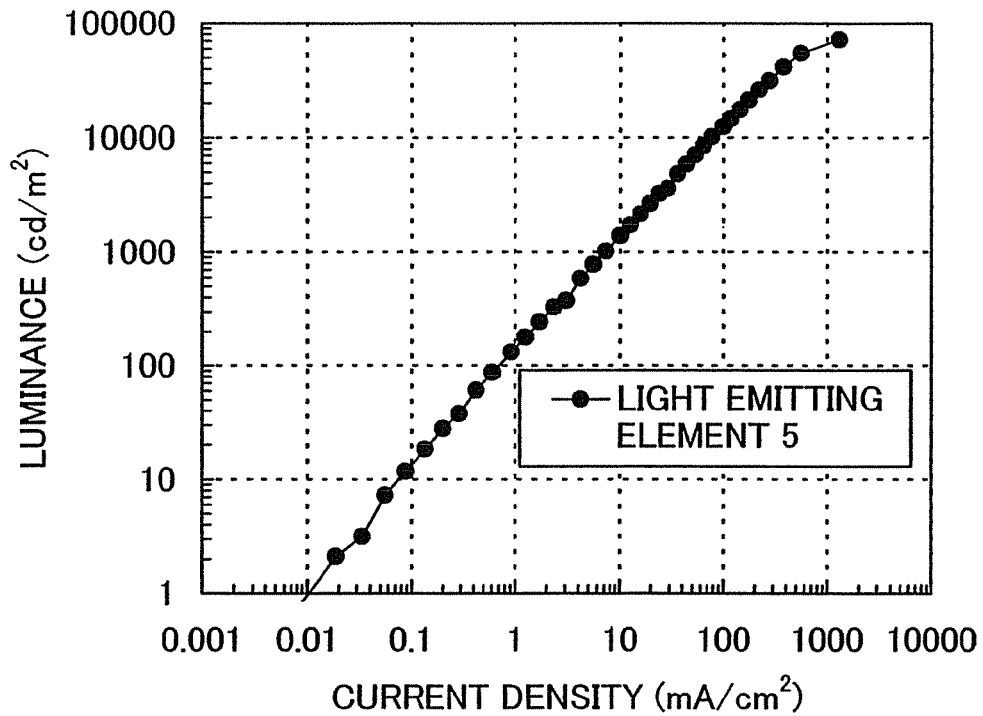
FIG. 37 is a graph showing current density vs. luminance characteristics of a light-emitting element 5 according to an aspect of the present invention.
Figure 38:
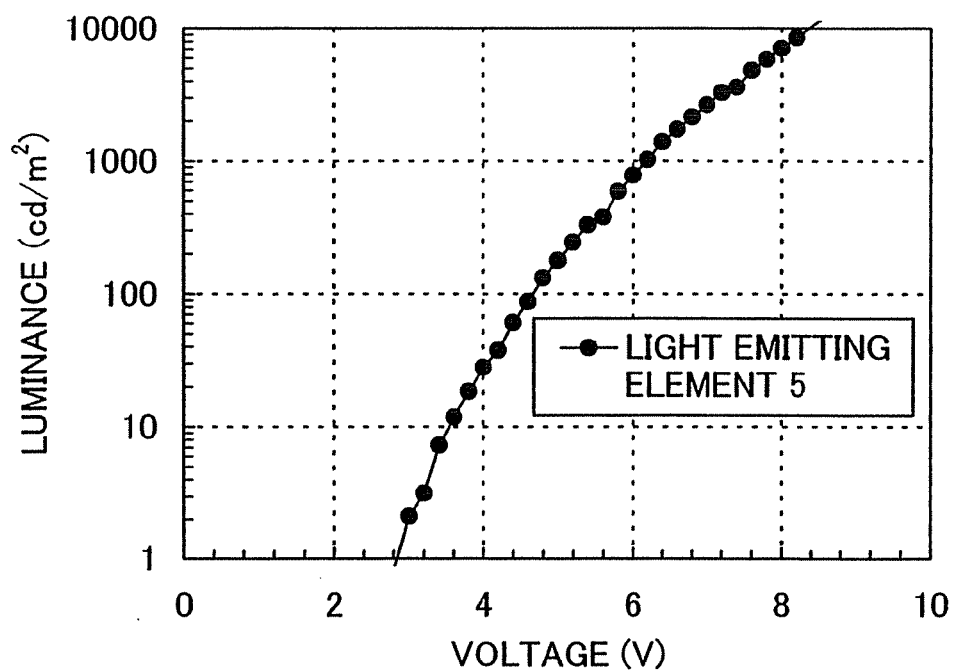
FIG. 38 is a graph showing voltage vs. luminance characteristics of the light-emitting element 5 according to an aspect of the present invention.
Figure 39:
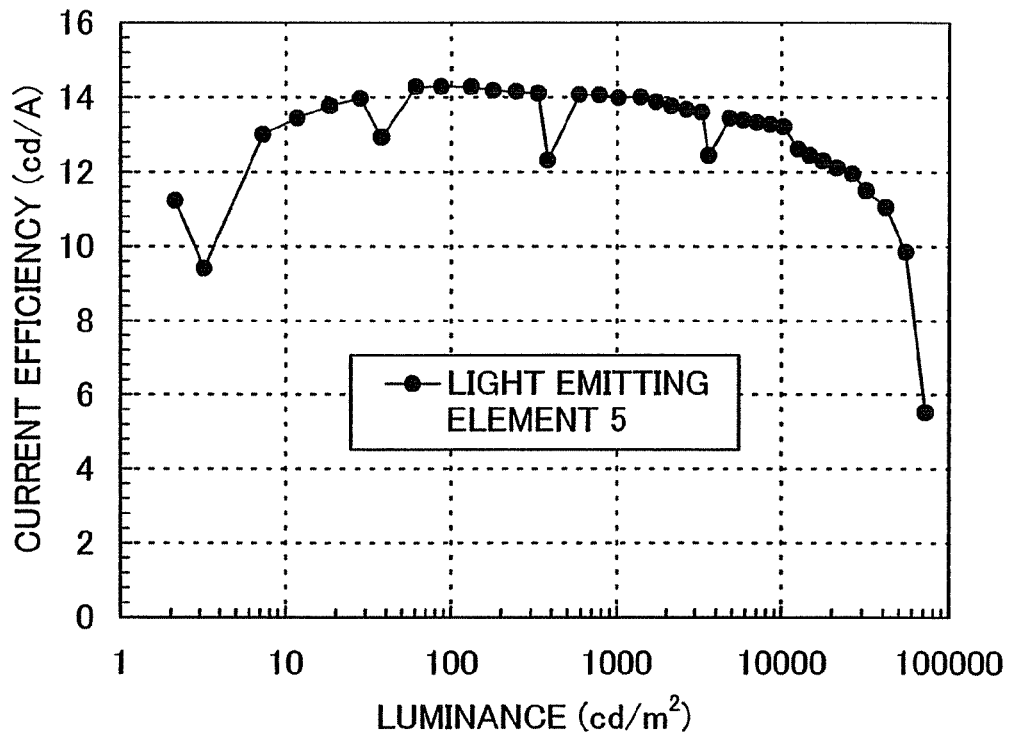
FIG. 39 is a graph showing luminance vs. current efficiency characteristics of the light-emitting element 5 according to an aspect of the present invention.
Figure 40:
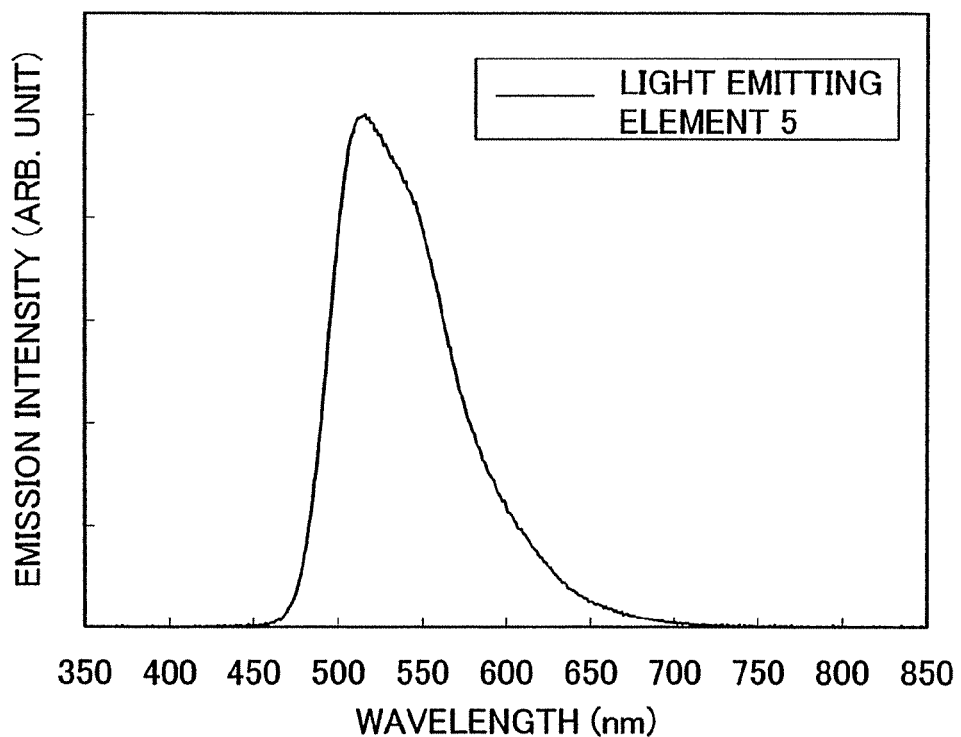
FIG. 40 shows an emission spectrum of the light-emitting element 5 according to an aspect of the present invention.

FIG. 37 shows current density-luminance characteristics of the light-emitting element 5, and FIG. 38 shows voltage-luminance characteristics thereof. FIG. 39 shows luminance-current efficiency characteristics of the light-emitting element 5. FIG. 40 shows emission spectra at a current supply of 1 mA of the light-emitting element. Note that CIE chromaticity coordinates of the light-emitting element 5 was (x, y)=(0.30, 0.62) at a luminance of 3280 cd/m$^2$, and green emission from the light-emitting element 5 was observed, which was derived from 2PCAPA, similar to the light-emitting element 1 and the reference light-emitting element 2 in Example 1 and the light-emitting element 3 in Example 2. Thus, the light-emitting element 5 has excellent color purity, similar to the light-emitting element 1 and the light-emitting element 3. The current efficiency and driving voltage at a luminance of 3280 cd/m$^2$ were 13.6 cd/A and 7.2 V respectively.

Figure 41:
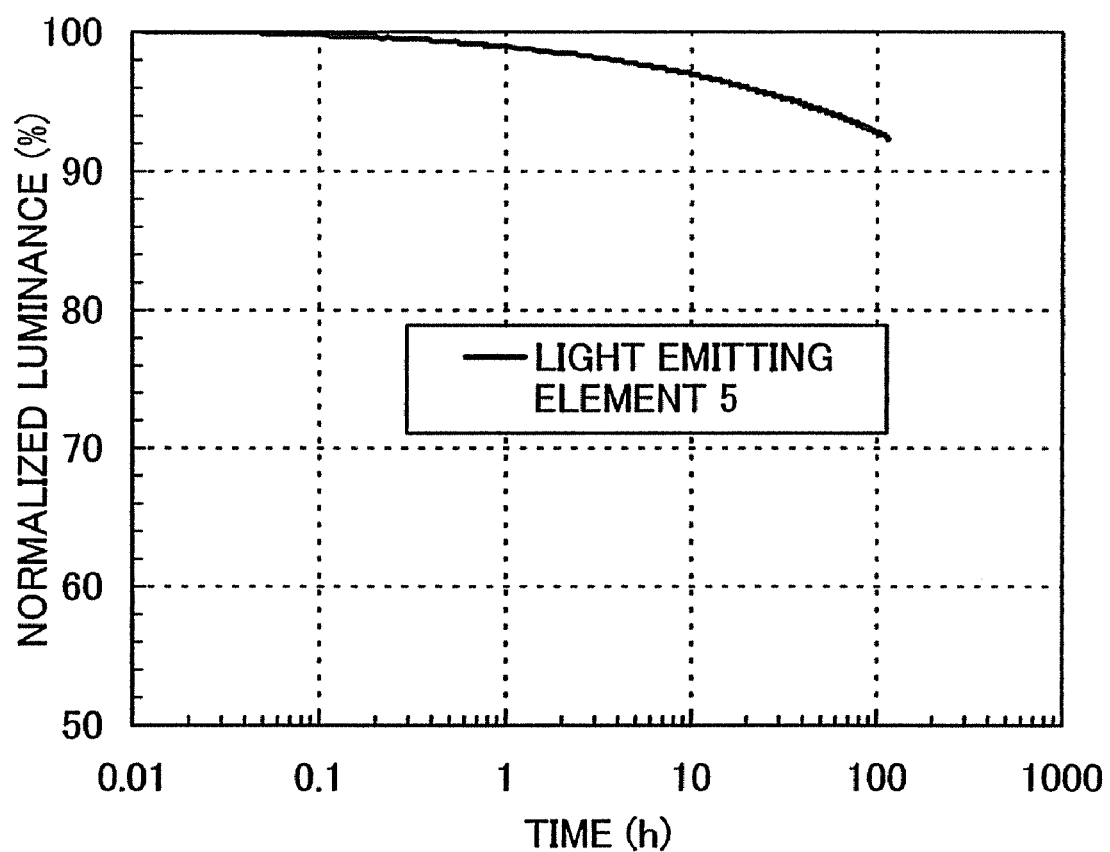
FIG. 41 shows a result of a continuous lighting test in which the light-emitting element 5 of the present invention was continuously lit by constant current driving.

FIG. 41 shows the result of a continuous lighting test in which the light-emitting element 5 was continuously lit by constant current driving with the initial luminance set at 5000 cd/m$^2$ (the vertical axis indicates the relative luminance on the assumption that 5000 cd/m$^2$ is 100%). From the result of FIG. 41, the light-emitting element 5 exhibits 93% of the initial luminance even after 100 hours, which leads to that the light-emitting element 5 has long lifetime, similar to the light-emitting elements 1 and 3. Thus, a light-emitting element having long lifetime can be fabricated in accordance with the present invention.

This application is based on Japanese Patent Application serial No. 2007-040379 filed with Japan Patent Office on Feb. 21, 2007, the entire contents of which are hereby incorporated by reference.

REFERENCE NUMERALS

101: first electrode, 102: second electrode, 112: hole-transporting layer, 113: second layer, 114: first layer, 115: electron-transporting layer, 131: organic compound, 132: light-emitting substance, 141: organic compound, 142: organic compound, 200: substrate, 201: first electrode, 202: second electrode, 203: EL layer, 211: hole-injecting layer, 212: hole-transporting layer, 213: second layer, 214: first layer, 215: electron-transporting layer, 216: electron-injecting layer, 217: layer including substance having high electron-transporting property, 501: first electrode, 502: second electrode, 511: first light-emitting unit, 512: second light-emitting unit, 513: charge generation layer, 601: source driver circuit, 602: pixel portion, 603: gate driver circuit, 604: sealing substrate, 605: sealing material, 607: space, 608: wiring, 609: FPC (flexible printed circuit), 610: element substrate, 611: switching TFT, 612: current-controlling TFT, 613: first electrode, 614: insulator, 616: EL layer, 617: second electrode, 618: light-emitting element, 623: n-channel TFT, 624: p-channel TFT, 701: substrate, 702: electrode, 703: insulating layer, 704: partition layer, 705: EL layer, 706: electrode, 901: housing, 902: liquid crystal layer, 903: backlight, 904: housing, 905: driver IC, 906: terminal, 1001: housing, 1002: light source, 1003: lighting device, 1004: television set, 1100: glass substrate, 1101: first electrode, 1102: second electrode, 1111: layer including composite material, 1112: hole-transporting layer, 1113: light-emitting layer, 1114: layer for controlling electron transfer, 1115: electron-transporting layer, 1116: electron-injecting layer, 2100: glass substrate, 2101: first electrode, 2102: second electrode, 2111: layer including composite material, 2112: hole-transporting layer, 2113: light-emitting layer, 2115: electron-transporting layer, 2116: electron-injecting layer, 9101: housing, 9102: support base, 9103: display portion, 9104: speaker portion, 9105: video input terminal, 9201: main body, 9202: housing, 9203: display portion, 9204: keyboard, 9205: external connection port, 9206: pointing device, 9401: main body, 9402: housing, 9403: display portion, 9404: audio input portion, 9405: audio output portion, 9406: operation key, 9407: external connection port, 9408: antenna, 9501: main body, 9502: display portion, 9503: housing, 9504: external connection port, 9505: remote control receiving portion, 9506: image receiving portion, 9507: battery, 9508: audio input portion, 9509: operation key, 9510: eye piece portion.

The invention claimed is:

1. A light-emitting element comprising:
    an electron transporting layer and a hole transporting layer between a first electrode and a second electrode; and
    a first layer and a second layer between the electron transporting layer and the hole transporting layer, wherein:
    the first layer includes a first organic compound and a second organic compound;
    the first layer is formed between the second layer and the electron transporting layer;
    the first layer includes the first organic compound more than the second organic compound;
    the first organic compound has an electron-transporting property;
    the second organic compound has an electron-trapping property;
    the second layer includes a light-emitting substance;
    an energy gap of the second organic compound is larger than an energy gap of the light-emitting substance; and
    a potential of the first electrode is configured to be higher than a potential of the second electrode to obtain a light emission from the light emitting element.

2. A light-emitting element comprising:
    an electron transporting layer and a hole transporting layer between a first electrode and a second electrode; and
    a first layer and a second layer between the electron transporting layer and the hole transporting layer, wherein:
    the first layer includes a first organic compound and a second organic compound;
    the first layer is formed between the second layer and the electron transporting layer;

the first layer includes the first organic compound more than the second organic compound;

the first organic compound has an electron-transporting property;

a lowest unoccupied molecular orbital of the second organic compound is lower than a lowest unoccupied molecular orbital of the first organic compound by 0.3 eV or more;

the second layer includes a light-emitting substance;

an energy gap of the second organic compound is larger than an energy gap of the light-emitting substance; and a potential of the first electrode is configured to be higher than a potential of the second electrode to obtain a light emission from the light emitting element.

3. The light-emitting element according to claim 1 or 2, wherein the energy gap of the second organic compound is 3.0 eV or larger.

4. The light-emitting element according to claim 1 or 2, wherein a peak of an emission wavelength of the second organic compound is greater than or equal to 350 nm and less than or equal to 450 nm.

5. The light-emitting element according to claim 1 or 2, wherein the energy gap of the second organic compound is 3.0 eV or larger and a peak of an emission wavelength of the second organic compound is greater than or equal to 350 nm and less than or equal to 450 nm.

6. The light-emitting element according to claim 1 or 2, wherein the second layer has an electron-transporting property.

7. The light-emitting element according to claim 1 or 2, wherein:

the second layer includes the light-emitting substance and a third organic compound;

the third organic compound is included more than the light-emitting substance; and the third organic compound has an electron-transporting property.

8. The light-emitting element according to claim 7, wherein the third organic compound is an anthracene derivative.

9. The light-emitting element according to claim 1 or 2, wherein the first layer and the second layer are formed so as to be in contact with each other.

10. The light-emitting element according to claim 1 or 2, wherein a thickness of the first layer is greater than or equal to 5 nm and less than or equal to 20 nm.

11. The light-emitting element according to claim 1 or 2, wherein the first organic compound is a metal complex.

12. The light-emitting element according to claim 1 or 2, wherein the second organic compound is a quinoxaline derivative.

13. The light-emitting element according to claim 1 or 2, wherein the second organic compound is 2,3-diphenylquinoxaline derivative.

14. The light-emitting element according to claim 1 or 2, wherein the second organic compound is 2,3,2',3'-tetraphenyl-6,6'-biquinoxaline derivative.

15. The light-emitting element according to claim 1 or 2, wherein the second organic compound is a quinoxaline derivative represented by a general formula (1),

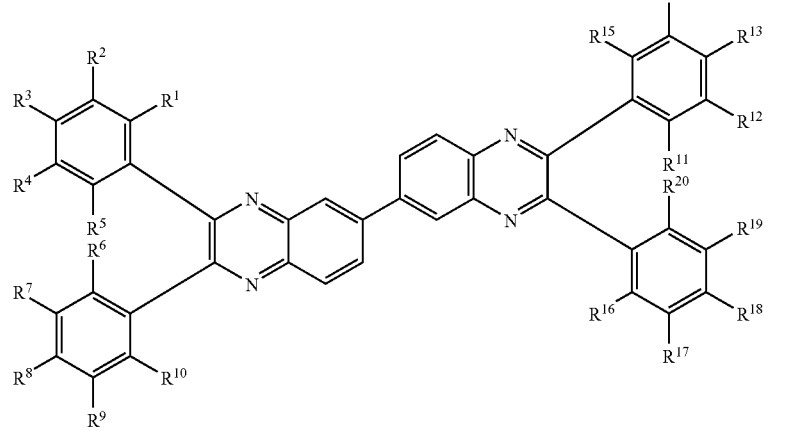

(1)

wherein at least one of $R^1$ to $R^{20}$ is any of a fluoro group, a cyano group, a trifluoromethyl group, a nitro group, an acyl group and an acyloxy group, and the others are hydrogen.

16. The light-emitting element according to claim 1 or 2, wherein the second organic compound is a quinoxaline derivative represented by a general formula (2),

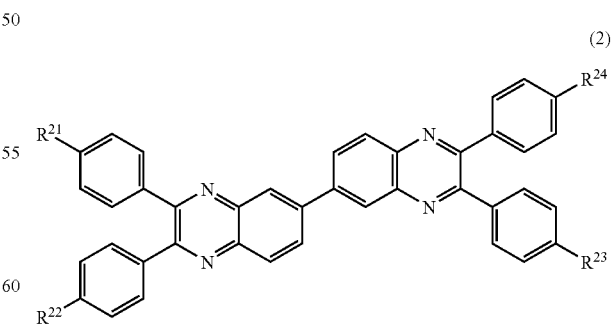

(2)

wherein at least one of $R^{21}$ to $R^{24}$ is any of a fluoro group, a cyano group, a trifluoromethyl group, a nitro group, an acyl group and an acyloxy group, and the others are hydrogen.

17. The light-emitting element according to claim 1 or 2, wherein the second organic compound is a quinoxaline derivative represented by the general formula (2),

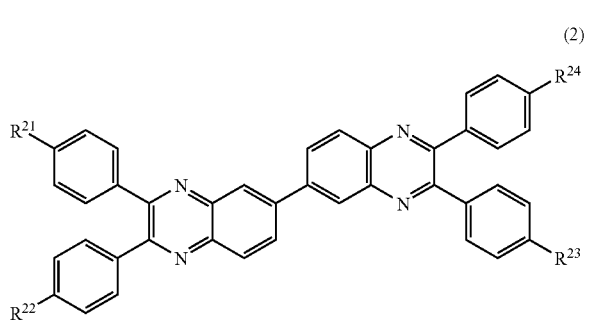

(2)

18. The light-emitting element according to claim 1 or 2, wherein the first electrode is an anode, and the second electrode is a cathode.

19. The light-emitting element according to claim 1 or 2, wherein the light-emitting element is incorporated in one selected from the group consisting of a television set, a computer, a mobile phone, a camera, a backlight, a table lamp, and an indoor lighting device.

20. A quinoxaline derivative represented by a general formula (1), wherein $R^{21}$ to $R^{24}$ are independently any one of a fluoro group, a cyano group, a trifluoromethyl group, a nitro group, an acyl group and an acyloxy group.

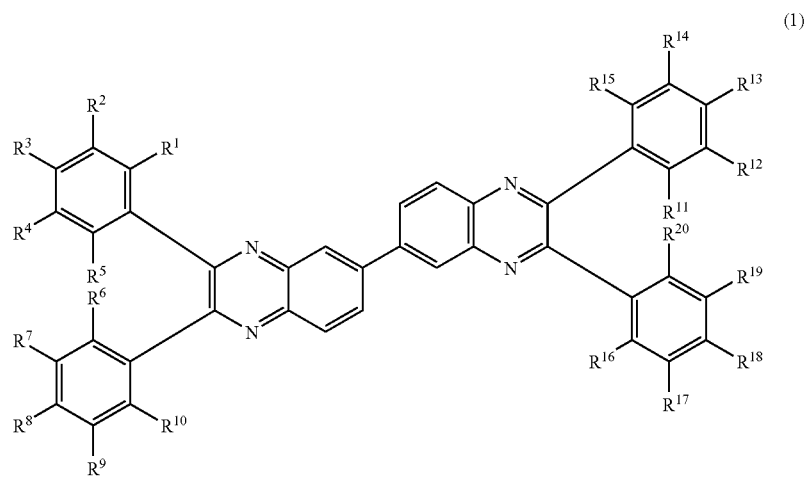

(1)

wherein at least one of $R^1$ to $R^{20}$ is any of a fluoro group, a cyano group, a trifluoromethyl group, a nitro group, an acyl group and an acyloxy group, and the others are hydrogen.

* * * * *